(12) United States Patent
Gallagher et al.

(10) Patent No.: US 8,282,964 B2
(45) Date of Patent: Oct. 9, 2012

(54) EX-VIVO TREATMENT OF PERIPHERAL PLASMACYTOID DENDRITIC CELLS WITH IFN-LAMBDA

(75) Inventors: Grant Gallagher, Milltown, NJ (US); Nicholas Megjugorac, Lopatcong, NJ (US); Grant E. Gallagher, Hamilton, NJ (US)

(73) Assignee: Medical Diagnostic Laboratories, LLC, Hamilton, NJ (US)

( * ) Notice: Subject to any disclaimer, the term of this patent is extended or adjusted under 35 U.S.C. 154(b) by 366 days.

(21) Appl. No.: 12/592,635

(22) Filed: Nov. 30, 2009

(65) Prior Publication Data

US 2011/0268707 A1    Nov. 3, 2011

Related U.S. Application Data

(63) Continuation-in-part of application No. 12/290,052, filed on Oct. 27, 2008.

(60) Provisional application No. 61/215,421, filed on May 5, 2009.

(51) Int. Cl.
*A61K 35/14* (2006.01)
*A61K 38/21* (2006.01)

(52) U.S. Cl. ............ 424/534; 424/85.4; 424/93.71

(58) Field of Classification Search .......... None
See application file for complete search history.

(56) References Cited

FOREIGN PATENT DOCUMENTS

WO    WO 2007/029041 A2    3/2007

OTHER PUBLICATIONS

Yamada., J. Inflammation Research 3: 33-44, 2010.*
Kerri A. Mowen, Laurie H. Glimcher, Signaling Pathways in Th2 Development, Immunogical Reviews, 2004, vol. 202, pp. 203-222.
Sophie Hue et al., Interleukin-23 Drives Innate and T cell-mediated Intestinal Inflammation, JEM, 2006, vol. 203, pp. 2473-2483.
Charles O. Elson et al., Monoclonal Anti-interleukin 23 Reverses Active Colitis in a T Cell-mediated Model in Mice, Gastroenterology, 2007, vol. 132, pp. 2359-2370.
Lauren Cohn et al., Asthma: Mechanisms of Disease Persistance, Annu. Rev. Immunol., 2004, vol. 22, pp. 789-815.
Juha Punnonen et al., Proc. Natl. Acad. Sci. USA, 1993, vol. 90, pp. 3730-3734.
Mike A. Berry et al., J Allergy Clin Immunol, 2004, vol. 114, pp. 1106-1109.
Marc Humbert et al., J Allergy Clin Immunol, 1997, vol. 99, pp. 657-665.
Joerg Mattes et al., IL-13 Induces Airways Hypersensitivity Independently of the IL-4R (alpha) Chain in the Allergic Lung, J. Immunol., 2001, vol. 167, pp. 1683-1692.
Stacey L. Fanning et al., J. Immunol., 2006, vol. 177, pp. 5829-5839.
Paul M. O'Byrne, Cytokines or Their Antagonists for the Treatment of Asthma, Chest, 2006, vol. 130, pp. 244-250.
Sergei V. Kotenko et al., Nature Immunology, 2003, vol. 4, pp. 69-77.
Ralph M. Steinman, Margaret D. Witmer, Proc. Natl. Acad. Sci. USA, 1978, vol. 75, pp. 5132-5136.
Antoni Kozlowski, J. Milton Harris, Journal of Controlled Release, 2001, vol. 72, pp. 217-224.

* cited by examiner

*Primary Examiner* — Gyan Chandra
(74) *Attorney, Agent, or Firm* — Siu K. Lo

(57) ABSTRACT

The present invention provides an ex vivo method of treating plasmacytoid dendritic cells (pDC) in Th2- or Th17-associated diseases by modulating the cytokine expression or secretion using interferon lambda (IFN-λ). For the Th-2 or Th17-associated diseases, pDC cells from a patient having the disease are exposed ex vivo with IFN-λ in an effective amount to inhibit cytokine releases. The IFN-λ exposed pDC are administered back into the patient. The present invention also provides a method of ex vivo IFN-λ treatment of pDC, in conjunction with co-administration of a composition comprising IFN-λ.

18 Claims, 33 Drawing Sheets

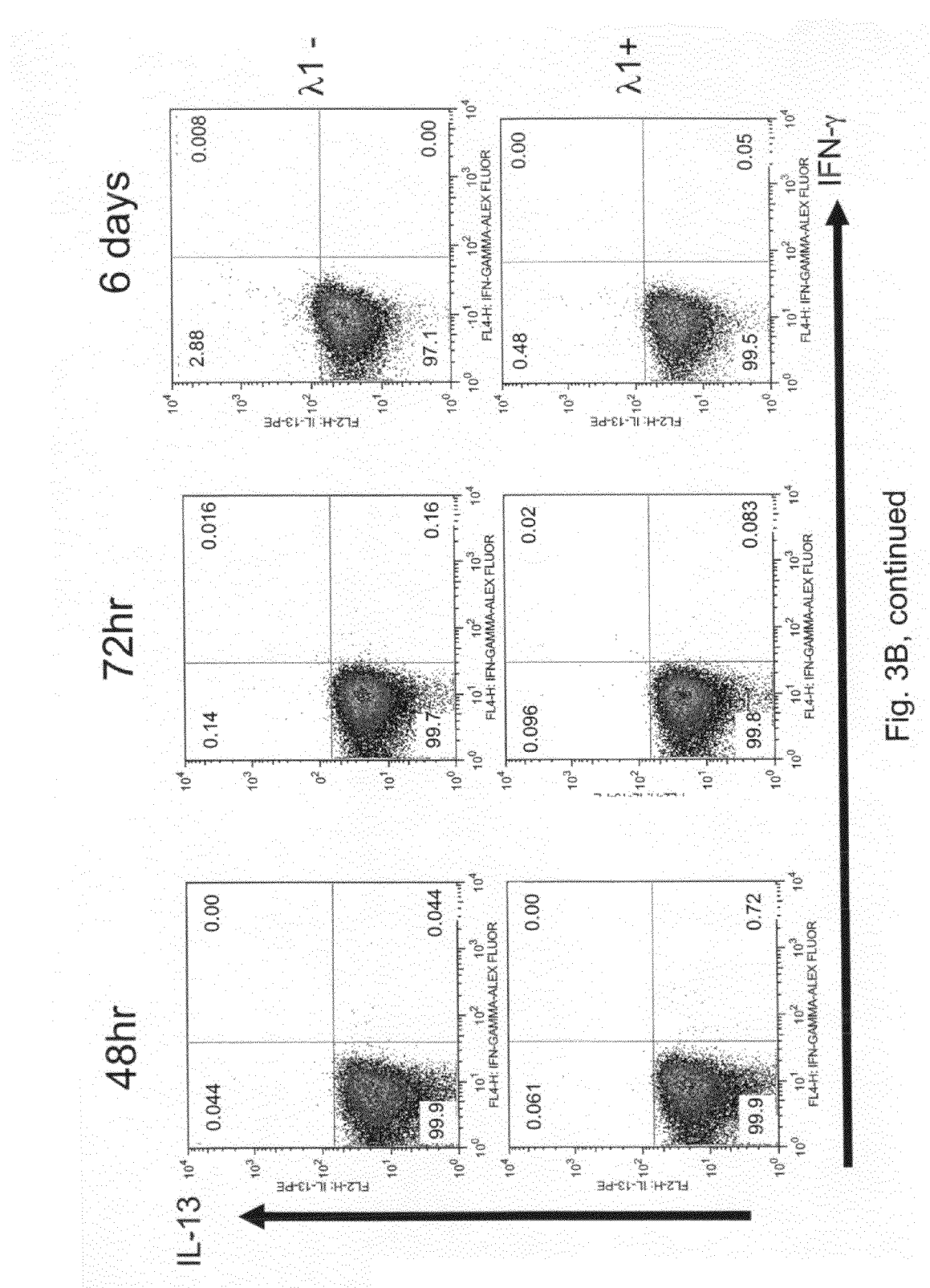
Fig. 3B, continued

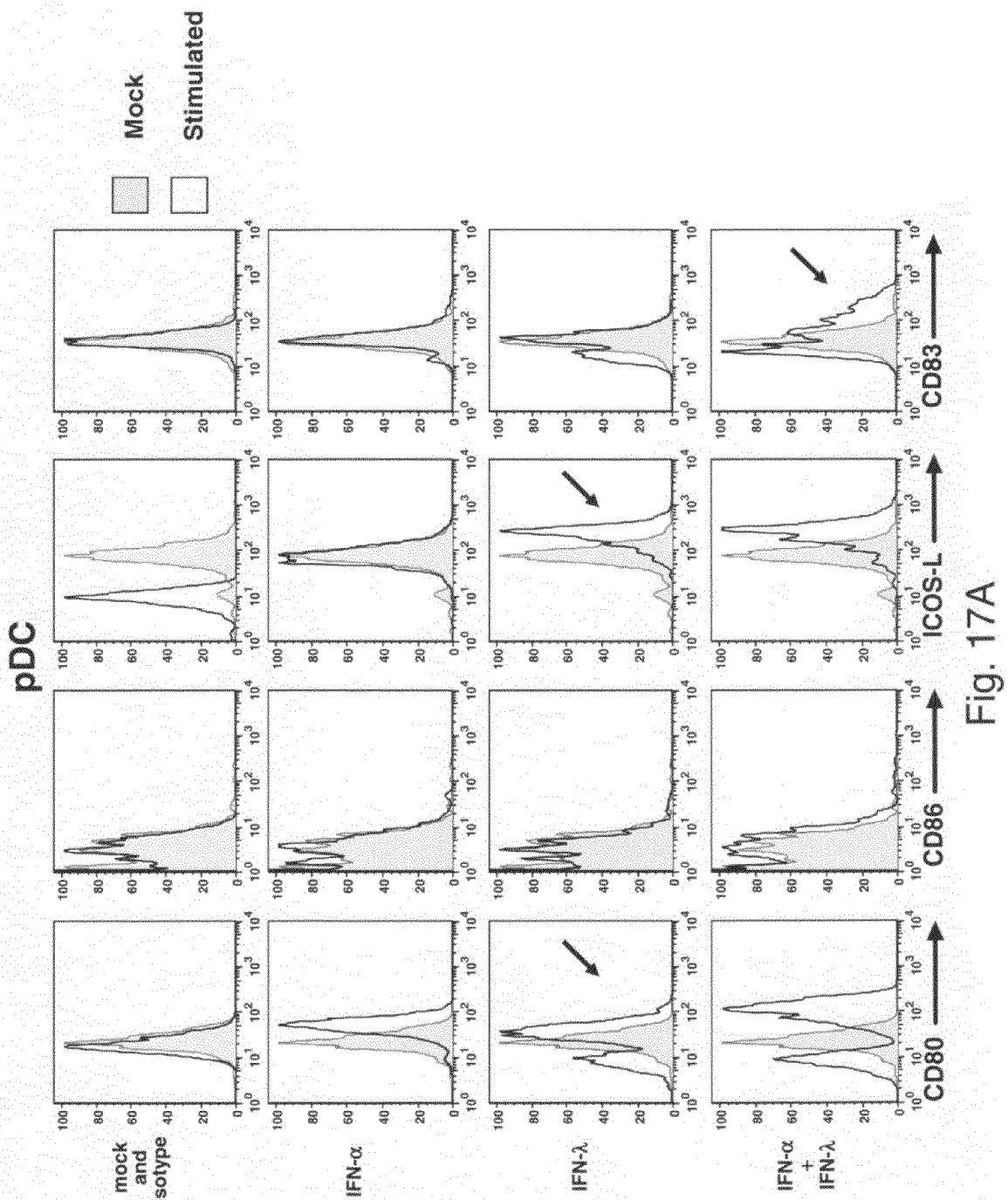

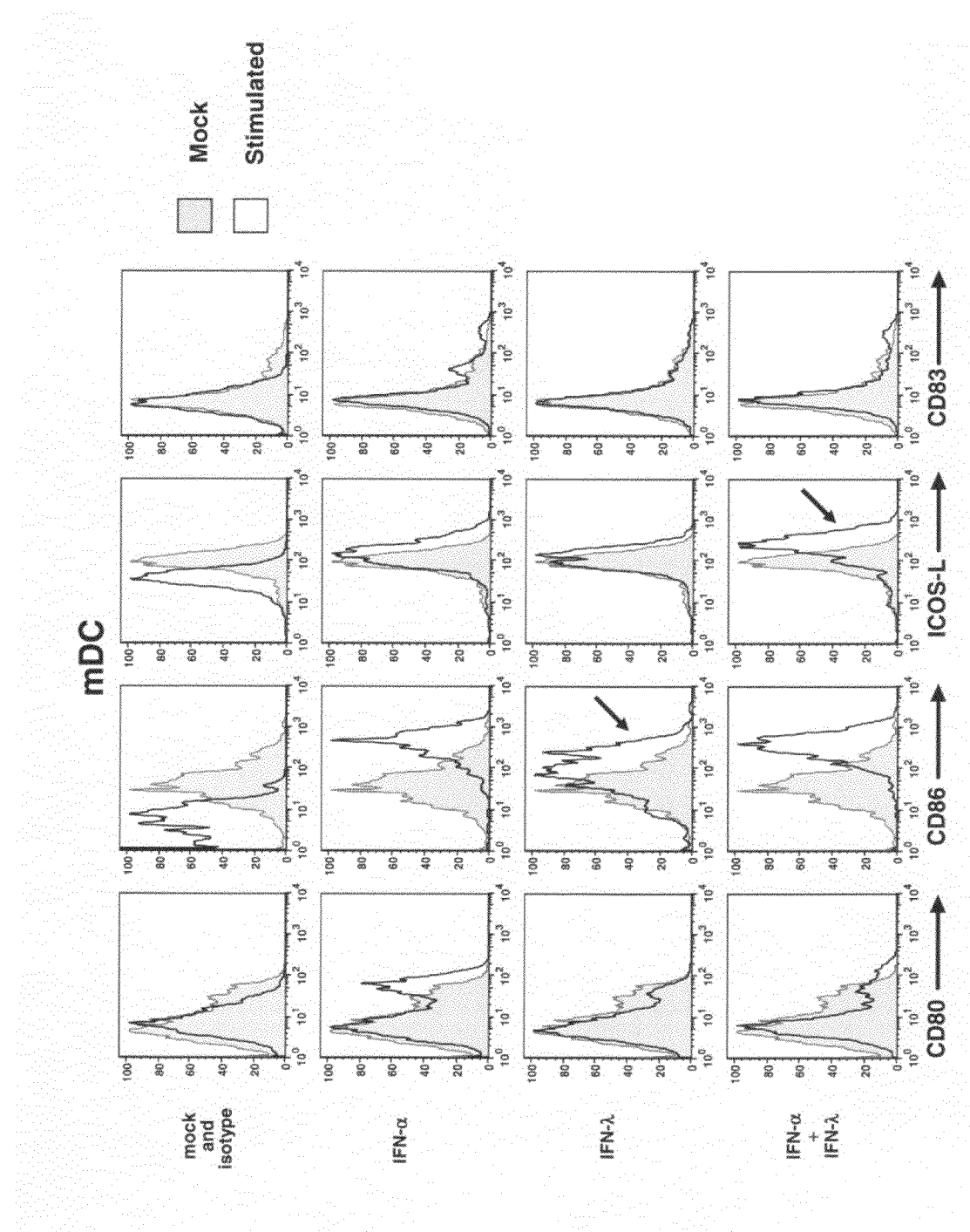

SEQUENCE LISTING

```
<160> NUMBER OF SEQ ID NOS: 17

<210> SEQ ID NO 1
<211> LENGTH: 200
<212> TYPE: PRT
<213> ORGANISM: Homo sapiens
<300> PUBLICATION INFORMATION:
<308> DATABASE ACCESSION NUMBER: GenBank Accession No:  Q8IU54

<400> SEQUENCE: 1

Met Ala Ala Ala Trp Thr Val Val Leu Val Thr Leu Val Leu Gly Leu
 1               5                  10                  15

Ala Val Ala Gly Pro Val Pro Thr Ser Lys Pro Thr Thr Thr Gly Lys
            20                  25                  30

Gly Cys His Ile Gly Arg Phe Lys Ser Leu Ser Pro Gln Glu Leu Ala
        35                  40                  45

Ser Phe Lys Lys Ala Arg Asp Ala Leu Glu Glu Ser Leu Lys Leu Lys
    50                  55                  60

Asn Trp Ser Cys Ser Ser Pro Val Phe Pro Gly Asn Trp Asp Leu Arg
65                  70                  75                  80
```

```
Leu Leu Gln Val Arg Glu Arg Pro Val Ala Leu Ala Glu Leu Ala
                 85                  90                  95

Leu Thr Leu Lys Val Leu Glu Ala Ala Gly Pro Ala Leu Glu Asp
            100                 105                 110

Val Leu Asp Gln Pro Leu His Thr Leu His His Ile Leu Ser Gln Leu
        115                 120                 125

Gln Ala Cys Ile Gln Pro Gln Pro Thr Ala Gly Pro Arg Pro Arg Gly
        130                 135                 140

Arg Leu His His Trp Leu His Arg Leu Gln Glu Ala Pro Lys Lys Glu
145                 150                 155                 160

Ser Ala Gly Cys Leu Glu Ala Ser Val Thr Phe Asn Leu Phe Arg Leu
                165                 170                 175

Leu Thr Arg Asp Leu Lys Tyr Val Ala Asp Gly Asn Leu Cys Leu Arg
            180                 185                 190

Thr Ser Thr His Pro Glu Ser Thr
            195                 200

<210> SEQ ID NO 2
<211> LENGTH: 200
<212> TYPE: PRT
<213> ORGANISM: Homo sapiens
<300> PUBLICATION INFORMATION:
<308> DATABASE ACCESSION NUMBER: GenBank Accession No:  Q8IZJ0

<400> SEQUENCE: 2

Met Lys Leu Asp Met Thr Gly Asp Cys Thr Pro Val Leu Val Leu Met
 1               5                  10                  15

Ala Ala Val Leu Thr Val Thr Gly Ala Val Pro Val Ala Arg Leu His
             20                  25                  30

Gly Ala Leu Pro Asp Ala Arg Gly Cys His Ile Ala Gln Phe Lys Ser
         35                  40                  45

Leu Ser Pro Gln Glu Leu Gln Ala Phe Lys Arg Ala Lys Asp Ala Leu
     50                  55                  60

Glu Glu Ser Leu Leu Leu Lys Asp Cys Arg Cys His Ser Arg Leu Phe
65                  70                  75                  80

Pro Arg Thr Trp Asp Leu Arg Gln Leu Gln Val Arg Glu Arg Pro Met
                 85                  90                  95

Ala Leu Glu Ala Glu Leu Ala Leu Thr Leu Lys Val Leu Glu Ala Thr
            100                 105                 110

Ala Asp Thr Asp Pro Ala Leu Val Asp Val Leu Asp Gln Pro Leu His
        115                 120                 125

Thr Leu His His Ile Leu Ser Gln Phe Arg Ala Cys Ile Gln Pro Gln
        130                 135                 140

Pro Thr Ala Gly Pro Arg Thr Arg Gly Arg Leu His His Trp Leu Tyr
145                 150                 155                 160

Arg Leu Gln Glu Ala Pro Lys Lys Glu Ser Pro Gly Cys Leu Glu Ala
                165                 170                 175

Ser Val Thr Phe Asn Leu Phe Arg Leu Leu Thr Arg Asp Leu Asn Cys
            180                 185                 190

Val Ala Ser Gly Asp Leu Cys Val
        195                 200

<210> SEQ ID NO 3
<211> LENGTH: 200
<212> TYPE: PRT
<213> ORGANISM: Homo sapiens
<300> PUBLICATION INFORMATION:
<308> DATABASE ACCESSION NUMBER: GenBank Accession No:  Q8IZI9
```

<400> SEQUENCE: 3

| Met | Lys | Leu | Asp | Met | Thr | Gly | Asp | Cys | Met | Pro | Val | Leu | Val | Leu | Met |
|---|---|---|---|---|---|---|---|---|---|---|---|---|---|---|---|
| 1 | | | | 5 | | | | | 10 | | | | | 15 | |

| Ala | Ala | Val | Leu | Thr | Val | Thr | Gly | Ala | Val | Pro | Val | Ala | Arg | Leu | Arg |
| | | | 20 | | | | | 25 | | | | | 30 | | |

| Gly | Ala | Leu | Pro | Asp | Ala | Arg | Gly | Cys | His | Ile | Ala | Gln | Phe | Lys | Ser |
| | | | 35 | | | | | 40 | | | | | 45 | | |

| Leu | Ser | Pro | Gln | Glu | Leu | Gln | Ala | Phe | Lys | Arg | Ala | Lys | Asp | Ala | Leu |
| | 50 | | | | | 55 | | | | | 60 | | | | |

| Glu | Glu | Ser | Leu | Leu | Leu | Lys | Asp | Cys | Lys | Cys | Arg | Ser | Arg | Leu | Phe |
| 65 | | | | | 70 | | | | | 75 | | | | | 80 |

| Pro | Arg | Thr | Trp | Asp | Leu | Arg | Gln | Leu | Gln | Val | Arg | Glu | Arg | Pro | Val |
| | | | | 85 | | | | | 90 | | | | | 95 | |

| Ala | Leu | Glu | Ala | Glu | Leu | Ala | Leu | Thr | Leu | Lys | Val | Leu | Glu | Ala | Thr |
| | | | | 100 | | | | | 105 | | | | | 110 | |

| Ala | Asp | Thr | Asp | Pro | Ala | Leu | Gly | Asp | Val | Leu | Asp | Gln | Pro | Leu | His |
| | | | 115 | | | | | 120 | | | | | 125 | | |

| Thr | Leu | His | His | Ile | Leu | Ser | Gln | Leu | Arg | Ala | Cys | Ile | Gln | Pro | Gln |
| | 130 | | | | | 135 | | | | | 140 | | | | |

| Pro | Thr | Ala | Gly | Pro | Arg | Thr | Arg | Gly | Arg | Leu | His | His | Trp | Leu | His |
| 145 | | | | | 150 | | | | | 155 | | | | | 160 |

| Arg | Leu | Gln | Glu | Ala | Pro | Lys | Lys | Glu | Ser | Pro | Gly | Cys | Leu | Glu | Ala |
| | | | | 165 | | | | | 170 | | | | | 175 | |

| Ser | Val | Thr | Phe | Asn | Leu | Phe | Arg | Leu | Leu | Thr | Arg | Asp | Leu | Asn | Cys |
| | | | 180 | | | | | 185 | | | | | 190 | | |

| Val | Ala | Ser | Gly | Asp | Leu | Cys | Val |
| | | 195 | | | | | 200 |

<210> SEQ ID NO 4
<211> LENGTH: 21
<212> TYPE: DNA
<213> ORGANISM: Artificial
<220> FEATURE:
<223> OTHER INFORMATION: Primer

<400> SEQUENCE: 4
ccagccagtc cagatcactc t                                         21

<210> SEQ ID NO 5
<211> LENGTH: 22
<212> TYPE: DNA
<213> ORGANISM: Artificial
<220> FEATURE:
<223> OTHER INFORMATION: Primer

<400> SEQUENCE: 5
acagcagtat cagaagcgat gg                                        22

<210> SEQ ID NO 6
<211> LENGTH: 16
<212> TYPE: DNA
<213> ORGANISM: Artificial
<220> FEATURE:
<223> OTHER INFORMATION: Primer

<400> SEQUENCE: 6
accacctgtt gtggtc                                               16

<210> SEQ ID NO 7

```
<211> LENGTH: 16
<212> TYPE: DNA
<213> ORGANISM: Artificial
<220> FEATURE:
<223> OTHER INFORMATION: Primer

<400> SEQUENCE: 7
cctttccaca ctgcac                                                    16

<210> SEQ ID NO 8
<211> LENGTH: 16
<212> TYPE: DNA
<213> ORGANISM: Artificial
<220> FEATURE:
<223> OTHER INFORMATION: Primer

<400> SEQUENCE: 8
tcaaggcaac cacgtc                                                    16

<210> SEQ ID NO 9
<211> LENGTH: 16
<212> TYPE: DNA
<213> ORGANISM: Artificial
<220> FEATURE:
<223> OTHER INFORMATION: Primer

<400> SEQUENCE: 9
gatggacgtc ttggag                                                    16

<210> SEQ ID NO 10
<211> LENGTH: 20
<212> TYPE: DNA
<213> ORGANISM: Artificial
<220> FEATURE:
<223> OTHER INFORMATION: Primer

<400> SEQUENCE: 10
ctgaaccatc caggccaaat                                                20

<210> SEQ ID NO 11
<211> LENGTH: 18
<212> TYPE: DNA
<213> ORGANISM: Artificial
<220> FEATURE:
<223> OTHER INFORMATION: Primer

<400> SEQUENCE: 11
gccgtgtggc aatccaat                                                  18

<210> SEQ ID NO 12
<211> LENGTH: 24
<212> TYPE: DNA
<213> ORGANISM: Artificial
<220> FEATURE:
<223> OTHER INFORMATION: Primer

<400> SEQUENCE: 12
ctgggaagac ctcattggtg tcac                                           24

<210> SEQ ID NO 13
<211> LENGTH: 24
<212> TYPE: DNA
<213> ORGANISM: Artificial
<220> FEATURE:
<223> OTHER INFORMATION: Primer

<400> SEQUENCE: 13
```

-continued

```
cggttatgga tgttcaggtt gacc                                          24

<210> SEQ ID NO 14
<211> LENGTH: 23
<212> TYPE: DNA
<213> ORGANISM: Artificial
<220> FEATURE:
<223> OTHER INFORMATION: Primer

<400> SEQUENCE: 14
cctccccctg gaattacact gtc                                           23

<210> SEQ ID NO 15
<211> LENGTH: 21
<212> TYPE: DNA
<213> ORGANISM: Artificial
<220> FEATURE:
<223> OTHER INFORMATION: Primer

<400> SEQUENCE: 15
cagggtctct tgctggatgg g                                             21

<210> SEQ ID NO 16
<211> LENGTH: 18
<212> TYPE: DNA
<213> ORGANISM: Artificial
<220> FEATURE:
<223> OTHER INFORMATION: Primer

<400> SEQUENCE: 16
tgcaccacca cctgctta                                                 18

<210> SEQ ID NO 17
<211> LENGTH: 19
<212> TYPE: DNA
<213> ORGANISM: Artificial
<220> FEATURE:
<223> OTHER INFORMATION: Primer

<400> SEQUENCE: 17
ggatgcaggg atgatgttc                                                19
```

EX-VIVO TREATMENT OF PERIPHERAL PLASMACYTOID DENDRITIC CELLS WITH IFN-LAMBDA

CROSS REFERENCE TO RELATED APPLICATIONS

The present application claims the benefit of priority to U.S. Provisional Application No. 61/215,421 filed May 5, 2009, and is a continuation-in-part application (CIP) of the U.S. Utility application Ser. No. 12/290,052 filed Oct. 27, 2008, which claims the benefit of priority to U.S. Provisional Application No. 60/983,168 filed Oct. 27, 2007, the entire disclosure of each of these applications is hereby incorporated by reference in its entirety.

FIELD OF THE INVENTION

The present invention generally relates to a method of ex vivo treatment of an immune cell by interferon lambda (IFN-λ). Specifically, the present invention provides a method of isolating peripheral blood leukocytes from a human subject, and further isolating plasmacytoid dendritic cells (pDC), and exposing the isolated pDC to IFN-λ at a concentration sufficient to reduce the pDC-support T-cell production of specific cytokines (i.e., IFN-γ, IL-13, IL-10 and IL-17), and administering the IFN-λ treated pDC into the human subject. The ex vivo treatment of pDC by IFN-λ reduces Th2 and Th17 responses, probably via its hitherto unexpected ability to modulate co-stimulatory molecules as well as homing molecules present in pDC. The ex vivo treatment may be combined with an administration of IFN-λ. The present invention is applicable to patients having Th2- and Th17-associated diseases such as asthma, inflammatory bowel diseases including Crohn's disease.

BACKGROUND OF THE INVENTION

Inflammatory bowel disease (IBD) is a chronic intestinal inflammatory disorder that affects >1.4 million people in the United States. Symptoms of IBD include abdominal pain, weight loss, fever, and diarrhea, resulting a significant mortality and morbidity. IBD includes Crohn's disease and ulcerative colitis. There is presently no cure for IBD. Treatment involves administration of sulfa drugs, corticosteroids, immuno-suppressives and anti-tumor necrosis factor agents. Patients often develop non-responsiveness to these drug treatments, and over time surgery represents the only option. Inflamed sections of the gut (e.g., colon) are resected, and connected to adjacent sections (e.g., ileoanal anastomosis). However, surgery does not guarantee successful treatment.

The underlying immunologic basis for IBD is complex and is not completely understood. IBD is a persistent inflammation in the gut that is driven by immune cells (e.g., T-cells), which are capable of sustaining a chronic production of inflammatory cytokines. In Crohn's disease, one of the major T-cell subtypes that contributes to disease is the Th17 cell, so named because of the production of the IL-17 cytokine family (e.g., IL-17A, IL-17F, IL-21, IL-22). The IL-17 cytokines may act in concert with other cytokines (e.g., IL-1, IL-13, IL-10, etc) to yield persistent and invasive inflammatory lesions. The chronic inflammation that drives IBD is significantly different from other types of inflammation (e.g., TNF and IL-1), including that which occurs in Irritable Bowel Syndrome (IBS), a less serious intestinal inflammatory disorder.

During IBD, immune cells such as dendritic cells (DC) and T-cells tend to influx into the inflamed tissues. Notably, IBD patients with active IBD have a lower circulating dendritic cells (DC) in the peripheral blood. (Baumgart D. C. et al., Gut 54(2):228-36, 2005). It is speculated that circulating DC migrates out from the blood compartment into the intestinal compartment. Once gaining access to an inflamed gut site, DC may activate T-cells to promote chronic intestinal inflammation. DC may present antigens to T-cells to provide a primary activation stimulus. DC may also provide a secondary activation stimulus via their co-stimulatory molecules. The interaction of co-stimulatory molecules between DC and T-cells during IBD progression remains elusive. The respective role of myeloid DC (mDC) and plasmacytoid DC (pDC) in this process remains unknown.

IL-23 is recognized to be important in IBD via its ability to drive Th17 cell differentiation, migration and cytokine production. IBD represents a complex inflammatory disorder in the gastrointestinal tract that involves Th17 cells. Situated within the lamina propria, Th17 cells produce an array of cytokines including IL-17, IL-21 and IL-22 in the gut compartment. These cytokines further activate epithelial cells, endothelial cells, and granulocytes to produce cytokines (such as TNF). Unchecked proliferation and cytokine production by Th17 cells leads to IBD flare-ups, accelerated disease progression and increased disease severity. Because IL-23 is necessary for the survival and activation of IL-17-producing cells, it represents a checkpoint in the Th17 differentiation. The critical role of IL-23 in IBD is revealed in a mouse model where IL-23 gene was deleted. (Hue S. et al. J. Exp. Med. 203: 2473-2483, 2006). The IL-23 receptor depletion abolishes the development of intestinal inflammation in colitis. There have been attempts to employ antibodies and peptides against IL-23 as a therapeutic means to control intestinal inflammation in IBD. (Elson C. O. et al., Gastroenterology 132(7): 2359-70, 2007). The success of this therapeutic approach remains to be confirmed.

Incidence of asthma and asthma-related disorders is increasing globally and in the developed world especially. According to a 2004 survey in the United States, asthma and related disorders resulted in almost 1.8 million emergency room visits, over 450,000 hospital admissions and 5,429 deaths. Asthma is directly responsible for approximately 15% of all pediatric emergencies (Cohn, Ann. Rev. Immunol., 2004; Barnes & Lemanske, New Engl. J. Med., 2001). The economic impact is high, estimated at ~$16 billion per year. These figures have been rising over the last 20 years. Thus, asthma constitutes a significant and growing medical problem in the United States in terms of morbidity and economic impact.

Triggered by airborne antigens such as pollens, viruses, fungi and bacteria, asthma involves a complex network of cytokines (Walker et al. J. Allergy Clin. Immunol., 1991). Accumulation of Th2 cells in the lung tissue is a key feature of asthma (Robinson et al., New Engl. J. Med., 1992). In the course of asthma, multiple cytokines are released from various cell types (e.g., epithelial cells, lymphocytes, mast cells and granulocytes) in the lung parenchyma. The released cytokines help to initiate and maintain asthma development. In experimental asthma models, airway hyper-reactivity is accompanied by high levels of IL-4 and IL-5. IL-4 appears to be essential for the development of Th2 responses in general (Mowen & Glimcher, Immunol. Rev., 2004), and animals genetically deficient in IL-4 (i.e., IL-4 knock-out mice) cannot be induced to develop allergic airway inflammation (Ray & Cohn, J. Clin. Invest., 1999).

Other evidence, however, suggests that IL-13, and not IL-4, seems to be a key cytokine to asthma pathogenesis in humans. In humans, asthma-specific T-cells produce IL-13, and IL-13 elevates mast-cell proliferation and induce IgE synthesis (Punnonen et al., Proc Natl Acad Sci USA., 1993). Sputa obtained from asthma patients are rich in IL-13 (Berry et al., J Allergy Clin Immunol., 2004). IL-13 mRNA and protein are expressed at a high level in the lungs of trigger-exposed human volunteers and asthma patients (Humbert et al., J. Allergy Clin. Immunol., 1997). Airway hyper-reactivity accompanied by high levels of IL-4, IL-5 and IL-13 can be induced in normal but not IL-13-/- mice (Mattes et al., J. Immunol., 2001) Thus far, experimental therapeutic strategies to target Th2 cytokines which do not address IL-13 have failed (O'Byrne, Chest, 2006). Asthma-sensitized animals can be protected by blocking the cell-surface receptor for IL-13 (Taube et al., J. Immunol., 2002). IL-13 appears to be a contributing factor in the increased IL-4 and IL-5 levels. Once initiated, elevated levels of IL-4 and IL-5 are believed to exacerbate the asthmatic response.

An attempt was proposed to use IFN-λ in order to alleviate asthma. To this end, Davies et al. (WO 2007/029041) disclose the use of IFN-λ in virus-induced exacerbation of asthma. An aerosolized dose is recommended to bring IFN-λ in direct contact with the virus-infected airway epithelial cells. This group hypothesized that IFN-λ would eradicate the viral infection, thus alleviating the virus's ability to exacerbate the asthma. Viruses (such as respiratory syncytial virus (RSV) and rhinovirus (RV)) are known to infect airway epithelial cells, and the anti-virus effect of IFN-λ is believed to be maximized by the proposed airway delivery of IFN-λ. The half-life of IFN-λ may hinder the approach, as attempts are made to couple the IFN-λ with polyethylene glycol (PEG) to extend its functional half-life and to present an alternative method of introducing IFN-λ, other than through expression of DNA constructs. However, the airway route does not guarantee IFN-λ to come in contact with cytokine-producing lymphoid cells in lung parenchyma. The presence of an exceedingly thick mucus layer in asthmatic patients further hinders the success of this approach. While Davies et al. proposes a direct anti-virus effect by IFN-λ, the possible role of IFN-λ with Th2 cells in the lung, blood and lymphoid compartments and their secreted products (i.e., IL-4, IL-5, IL-13 cytokines, etc.), has not been addressed.

Intravenous delivery of IFN-λ is undesirable. Once administered, circulating IFN-λ may exert global side-effects on a human body. In addition, Th2 cytokine-producing cells in the lung parenchyma may be shielded from the systemic levels of IFN-λ. It is generally believed that intravenous administration IFN-λ is not ideal to combat asthma.

There is a continuing need to find an effective means to modulate Th2 cells as well as Th17 cells in an attempt to blunt cytokine production. The present inventors surprisingly found that IFN-λ can directly modulate Th2 cells and Th17 cells in affecting the cytokine release. Specifically, the present inventors discovered that ex-vivo treatment of peripheral mononuclear cells (including naïve and memory T-cells) blunts the production of IL-4, IL-5 and IL-13. Also, the present inventors discovered that ex-vivo treatment of pDC blunts the production of IL-13, IL-10 and IL-17. Given that these cytokines contribute to an asthma and IBD response, the present inventors propose a method of alleviating asthma and IBD by ex-vivo treatment of human blood leukocytes and isolated pDC with IFN-λ, followed by its administration into a human. It is believed that administration of IFN-λ-treated blood leukocytes as well as pDC will inhibit the human body from generating Th2 and Th17 cytokines, and thus alleviating the symptoms and root-cause of diseases including inflammatory bowel diseases and asthma.

SUMMARY OF THE INVENTION

In one aspect, the present invention provides a method of alleviating a Th2 disease, comprising the steps of: (a) identifying a patient having a Th2 disease; (b) isolating peripheral blood leukocytes containing immune cells from said patient; (c) exposing said immune cells to IFN-λ in an amount effective to reduce IL-4, IL-5 and IL-13 production from said immune cells when stimulated; and (d) administering said IFN-λ-exposed immune cells to said patient.

In another aspect, the present method may be used to treat peripheral mononuclear blood cells or fractionated cells enriched for a particular cell type, such as, for example naïve T-cells or memory T-cells.

The Th2 diseases to be alleviated by the present method include, but are not limited to, asthma, allergic bronchitis, interstitial lung disease, allergic airway disease, allergic rhinitis, and the like. Preferably, the Th2 disease is asthma. Asthma includes allergic asthma, intrinsic asthma, and occupational asthma.

The present method may employ IFN-λ1, IFN-λ2, IFN-λ3 or a combination thereof. The cells that are used in this method may be peripheral mononuclear blood cells or a fraction of these cells enriched for a certain cell type, such as, for example, T-cells.

In yet another aspect, the present invention provides a method of ex vivo treatment, comprising the steps of: (a) obtaining peripheral blood from a human subject; (b) isolating mononuclear cells from said peripheral blood; (c) exposing said isolated mononuclear cells to IFN-λ; and (d) administering said exposed cells to said human subject, wherein said IFN-λ is in an amount sufficient to inhibit stimulus-induced cytokine release, and wherein said cytokine is selected from the group consisting of IL-4, IL-5 and IL-13 and said stimulus is selected from the group consisting of Concanavalin A and anti-CD2/3/28 beads. Preferably, IFN-λ is selected from the group consisting of IFN-λ1, IFN-λ2, IFN-λ3 and a combination thereof. Preferably, the mononuclear cells are T-cells. More preferably, the T-cells are naïve T-cells or memory T-cells.

In another aspect, the present invention provides an ex vivo treatment using IFN-λ in the concentration range about 1 ng/mL to about 200 μg/mL. Preferably, the concentration range is about 100 ng/mL to about 10 μg/mL.

In another aspect, the present invention provides an ex vivo treatment of IFN-λ for suitable duration sufficient to inhibit IL-4, IL-5 and IL-13 production. Preferably, the IFN-λ treatment is performed for about 1 hour to about 24 hours. Preferably, the treatment duration is about 6 hours to about 12 hours. More preferably, the treatment duration is about 6 hours.

In another aspect, the present invention provides an ex vivo treatment of immune cells with IFN-λ, where the immune cells used are in the range of about $1 \times 10^7$ cells to about $1 \times 10^9$ cells. Preferably, the immune cells are about $1 \times 10^8$ cells. Preferably, the ex vivo treatment of IFN-λ can be repeated by further exposing immune cells to IFN-λ.

In another aspect, the present method includes the step of administering IFN-λ-treated immune cells back into the human patients.

In another aspect, the present invention further provides co-administration of IFN-λ, in addition to the ex vivo treatment. Preferably, the IFN-λ treatment and ex vivo treatment may be performed simultaneously or sequentially. Preferably, IFN-λ treatment may be performed within 24-48 hours after ex vivo treatment.

In yet another aspect, the present invention also provides a method of ex vivo treatment of plasmacytoid dendritic cells (pDC), comprising the steps of: (a) obtaining peripheral blood from a human subject; (b) isolating mononuclear cells from said peripheral blood; (c) isolating pDC from said isolated mononuclear cells using negative cell selection; (d) exposing said isolated pDC to IFN-λ; and (e) administering said exposed pDC to said human subject, wherein said IFN-λ is present in an amount sufficient to inhibit pDC-supported cytokine release in a mixed lymphocyte reaction assay, and wherein said pDC-supported cytokine is selected from the group consisting of IFN-γ, IL-13, IL-10 and IL-17.

In another aspect, the present invention provides a negative cell selection that can be used to isolate pDC. The negative cell selection is performed by (i) exposing the isolated mononuclear cells to a magnetic bead that is coupled with a monoclonal antibody against a cell surface molecule that is present on said mononuclear cells but absent on pDC, and (ii) removing the mononuclear cells that are bound with the magnetic beads.

In one aspect, the present invention utilizes beads that are coupled with monoclonal antibodies against cell surface molecule including CD3 (T-cells), CD20 (B cells), CD19 (B cells), CD56 (NK cells), CD16 (NK cells), CD14 (monocytes), glycophorin A (red blood cells), CD1a (mDC), CD11c (mDC), BDCA 1 (mDC) or BDCA 3 (mDC).

Preferably, IFN-λ is selected from the group consisting of IFN-λ1, IFN-λ2, and IFN-λ3. The IFN-λ amount used in treating pDC is in the range of about 1 ng/mL to about 200 µg/mL. More preferably, the IFN-λ amount is in the range of about 100 ng/mL to about 10 µg/mL. Preferably, the exposing step is performed for about 1 hour to about 24 hours. More preferably, the exposing step is performed for about 6 hours to about 12 hours.

In one aspect, the IFN-λ treatment of pDC results in reduction of IL-17, including IL-17A or IL-17F.

In one aspect, the administration of IFN-λ treated pDC to a human subject could alleviate the progression of a disease selected from the group consisting of inflammatory bowel disease and asthma. The inflammatory bowel disease is Crohn's disease or ulcerative colitis. Preferably, the inflammatory bowel disease is Crohn's disease.

In one aspect, the administration of IFN-λ treated pDC to a human subject could alleviate the progression of asthma. The asthma can be virus-induced or allergen-induced.

In one aspect, the present invention provides a negative cell isolation which results in isolation of pDC having a cell purity of greater than 95%. Preferably, the isolated pDC having a cell purity of greater than 97%.

In one aspect, the present invention provides administering to a human subject suffering from a disease with IFN-λ exposed pDC. Preferably, about $5\times10^4$ cells to about $5\times10^6$ cells of IFN-λ-treated pDC are administered into a human subject. More preferably, about $1\times10^6$ cells of IFN-λ-treated pDC are administered.

In one aspect, the present invention provides co-administration of IFN-λ-treated pDC and a composition comprising IFN-λ to a human subject. Preferably, the IFN-λ composition is administered nasally, intravenously, or orally. Preferably, to co-administration can be performed simultaneously or sequentially.

BRIEF DESCRIPTION OF THE DRAWINGS

FIG. 17 shows the effect of IFN-λ1 and IFN-α on the pDC (A) and mDC (B) co-stimulatory molecules (i.e., CD80, CD83, CD86, and inducible co-stimulator ligand/B7RP-1 (ICOS-L) using flow cytometry.

DETAILED DESCRIPTION OF THE INVENTION

Figure 1:
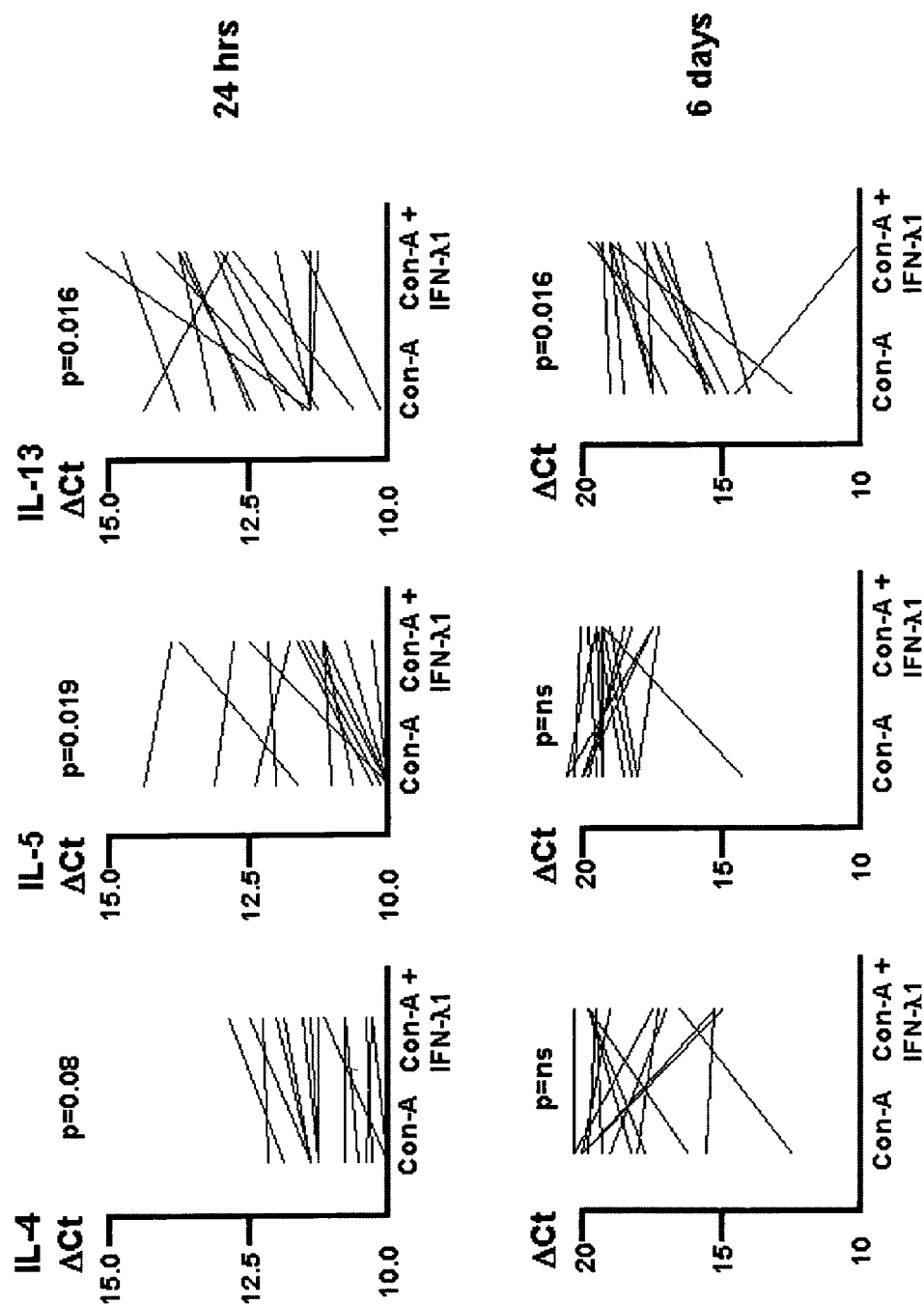
FIG. 1 shows that IFN-λ lowers the IL-4 and IL-13 mRNA levels. Panel A (IL-4 mRNA levels at 24 hours); Panel B (IL-5 mRNA levels at 24 hours); Panel C (IL-13 mRNA levels at 24 hours); Panel D (IL-4 mRNA levels at 6 days); Panel E (IL-5 mRNA levels at 6 days); Panel F (IL-13 mRNA levels at 6 days).

All patents, patent applications, published literature and citations to the NCBI database Accession Numbers cited herein are incorporated by reference in their entirety including all amino acid sequence data therein.

Standard reference works setting forth the general principles of recombinant DNA technology known to those of skill in the art include Ausubel et al., *CURRENT PROTOCOLS IN MOLECULAR BIOLOGY*, John Wiley & Sons, New York, 1998; Sambrook et al., *MOLECULAR CLONING: A LABORATORY MANUAL*, 2D ED., Cold Spring Harbor Laboratory Press, Plainview, N.Y., 1989; Kaufman et al., Eds., *HANDBOOK OF MOLECULAR AND CELLULAR METHODS IN BIOLOGY AND MEDICINE*, CRC Press, Boca Raton, 1995; McPherson, Ed.

DEFINITIONS

As used herein, the term "interferon lambda" (i.e., IFN-λ) is used interchangeably to describe a family of proteins that include IFN-λ1 (IL-29); IFN-λ2 (IL-28A); IFN-λ3 (IL-28B). These proteins are termed "Type III" interferons (Kotenko et al., 2003, Nat. Immunol., 4, 69-77). For purposes of this application, IFN-λ is intended to encompass all members of the IFN-λ family including, for example, IFN-λ1, IFN-λ2, IFN-λ3, and the variants thereof insofar as these molecules function equivalently in the methods of the invention in inhibiting cytokine production of IL-4, IL-5 and IL-13 from immune cells. Signaling is mediated through a heterodimeric receptor complex composed of the signaling subunit, IL-28Rα and the non-signaling chain, IL-10Rβ; all three ligands signal through this receptor.

The amino acid sequences of IFN-λ are known. The three IFN-λ polypeptide sequences have been dispositied in GenBank. The respective amino acid sequences are set forth as follow:

```
IFN-λ1: GenBank Accession No: Q8IU54
                                                          (SEQ ID NO: 1)
       MAAAWTVVLV  TLVLGLAVAG  PVPTSKPTTT  GKGCHIGRFK  SLSPQELASF        50

KKARDALEES  LKLKNWSCSS  PVFPGNWDLR  LLQVRERPVA  LEAELALTLK       100

VLEAAAGPAL  EDVLDQPLHT  LHHILSQLQA  CIQPQPTAGP  RPRGRLHHWL       150

HRLQEAPKKE  SAGCLEASVT  FNLFRLLTRD  LKYVADGNLC  LRTSTHPEST       200

IFN-λ2: GenBank Accession No: Q8IZJ0
                                                          (SEQ ID NO: 2)
       MKLDMTGDCT  PVLVLMAAVL  TVTGAVPVAR  LHGALPDARG  CHIAQFKSLS        50
```

```
-continued
PQELQAFKRA KDALEESLLL KDCRCHSRLF PRTWDLRQLQ VRERPMALEA      100

ELALTLKVLE ATADTDPALV DVLDQPLHTL HHILSQFRAC IQPQPTAGPR      150

TRGRLHHWLY RLQEAPKKES PGCLEASVTF NLFRLLTRDL NCVASGDLCV      200

IFN-λ3: GenBank Accession No: Q8IZI9
                                                   (SEQ ID NO: 3)
MKLDMTGDCM PVLVLMAAVL TVTGAVPVAR LRGALPDARG CHIAQFKSLS       50

PQELQAFKRA KDALEESLLL KDCKCRSRLF PRTWDLRQLQ VRERPVALEA      100

ELALTLKVLE ATADTDPALG DVLDQPLHTL HHILSQLRAC IQPQPTAGPR      150

TRGRLHHWLH RLQEAPKKES PGCLEASVTF NLFRLLTRDL NCVASGDLCV      200
```

As used herein, the term "human subject" refers to a human at risk of, or suffering from, asthma or IBD. Guidelines for diagnosing asthma are known in the art; for example, Global Initiative for Asthma has provided a guideline publication (see, ginasthma.com). Guidelines for diagnosing IBD are also recognized by a physician (e.g., gastroenterologist). For purposes of the present invention, the invention may also be used in mammals other than human, such as domestic animals (e.g., dog, cat, and the like) as well as experimental animals (e.g., mouse, rabbit, and the like).

As used herein, the term "ex vivo" refers to a condition that takes place outside an organism. Specifically, treatment of immune cells ex vivo means exposing such cells to IFN-λ in an artificial environment (sterile conditions) outside the organism with the minimum alteration of the natural conditions. This procedure involves culturing mononuclear cells that have been isolated from a human prior to administration back into the same human subject.

As used herein, the term "Th1 disease or disorder" refers to a pathological state in which a Th1 response contributes to the pathology. In Th1 disease, Th1-type cytokines tend to produce the pro-inflammatory responses responsible for killing intracellular parasites and for perpetuating autoimmune responses. Interferon gamma (IFN-γ) is the main Th1 cytokine. Excessive pro-inflammatory responses can lead to uncontrolled tissue damage.

As used herein, the term "Th2 disease or disorder" refers to a pathological state in which a Th2 response contributes to the pathology. In Th2 disease, Th2-type cytokines include IL-4, IL-5, and IL-13, which are associated with the promotion of IgE and eosinophilic responses in atopy, which has more of an anti-inflammatory response. Th2 responses will counteract the Th1 mediated microbicidal action. The optimal scenario to maintain a health condition would be that humans should produce a well balanced Th1 and Th2 response, suited to the immune challenge.

As used herein, the term "Th17 disease or disorder" refers to a pathological state in which Th17 cells or their secreted products contribute to the pathology. In Th17 diseases, Th17-related cytokines include IL-17 (e.g. IL-17A, IL-17F and the like), IL-21 and IL-22, which are associated with chronic inflammation. Th17 responses counteract the Th1 and Th2 responses.

As used herein, the term "asthma" includes various disorders of the airway, including, for example, asthma, allergic rhinitis and chronic obstructive pulmonary disorder. For purposes of this application, asthma is intended to encompass various forms of asthma including intrinsic asthma, allergic asthma, allergic airways disease, allergic bronchopulmonary aspergillosis, allergic bronchitis, occupational asthma, reactive airway disease syndrome, interstitial lung disease, and the like.

As used herein, the term "inhibit" refers to a decrease or elimination of the referenced parameter. The terms "treatment" and "inhibition" are used interchangeably in this application. For example, when an immune cell is stimulated with an agonist such as Concanavalin A or anti-CD2/3/28 engagement, cytokine production (e.g., IL-13) is elevated. However, when pre-treated with IFN-λ, the immune cell's production of IL-13 is decreased or eliminated.

As used herein, the term "peripheral blood mononuclear cells" (i.e., PBMC) is used interchangeable with "immune cells." PBMC is intended to encompass T-cells, B-cells, monocytes, and natural killer cells, all of which are characterized as having a single nucleus. PBMC can be conveniently obtained from human peripheral blood using a density-gradient centrifugation technique. ~70% of PBMC are T-cells, of which ~50% are naïve T-cells and ~50% are memory T-cells.

As used herein, the term "dendritic cells" (DC) represents a heterogeneous cell population including two main subtypes: namely, myeloid DC (mDC) and plasmacytoid DC (pDC) (Steinman et al., 1979, J. Exp. Med., 149, 1-16). These two blood DC subsets were originally differentiated by their expression of CD11c (integrin complement receptor) and CD123 (IL-3Rα). Each of the pDC and mDC populations constitutes between about 0.2 to about 0.6% of the PBMC population in humans.

As used herein, the term "pDC" means plasmacytoid dendritic cells and they represent a subtype of circulating dendritic cells found in the blood and peripheral lymphoid organs. These cells express the surface markers CD123, BDCA-2(CD303) and BDCA-4(CD304) and HLA-DR, but do not express CD11c, CD14, CD3, CD20 or CD56, which distinguishes them from conventional dendritic cells, monocytes, T-cells, B cells and NK cells. As components of the innate immune system, these cells express intracellular Toll-like receptors 7 and 9, which enable the detection of viral and bacterial nucleic acids, such as ssRNA or CpG DNA motifs. Upon stimulation and subsequent activation, these cells produce large amounts of Type I interferon (mainly IFN-α and IFN-β) and Type III interferon (e.g., IFN-λ), which are critical pleiotropic anti-viral compounds mediating a wide range of effects.

As used herein, the term "mDC" means myeloid dendritic cells and they represent a subtype of circulating dendritic cells found in blood and peripheral lymphoid organs. These cells express the surface markers CD11c, CD1a, HLA-DR and either BDCA-1 (CD1c) or BDCA-3 (CD141). They do not express BDCA-2 or CD123, which distinguishes them from pDC. mDC also do not express CD3, CD20 or CD56. As components of the innate immune system, mDC express Toll-like receptors (TLR), including TLR2, 3 and 4, which enable the detection of bacterial and viral components. Upon stimulation and subsequent activation, these cells produce large amounts of IL-12, which is critical for activation of certain immune responses.

As used herein, the term "stimulus-induced" refers to using a T-cell stimulus that induces T-cell activation. Exemplary stimuli include, but are not limited to, mitogens such as Concanavalin A, and anti-CD2/3/28 beads. The term "pDC-support cytokine release in a mixed lymphocyte reaction" refers to the ability of pDC to support T-cells' release of cytokine in a mixed reaction into the co-culture medium. In a mixed lymphocyte reaction, pDC normally support T-cell activation, via co-stimulatory molecules, for the cytokine release from the T-cells.

As used herein, the term "glycophorin A" refers to a sialoglycoprotein present on the surface of all human red blood cells.

As used herein, the term "T-cells" refers to a subset of lymphocytic cells (matured in thymus) that are present in PBMC and express a surface marker of "CD3" (T-cell receptor). T-cells are intended to include $CD4^+$ (i.e., T-helper cells) and $CD8^+$ (i.e., cytotoxic killer cells).

As used herein, the term "naïve T-cell" is a T-cell that has differentiated in bone marrow and successfully undergone the positive and negative processes of central selection in the thymus. A naïve T-cell is considered mature, but is distinguished from activated T-cells or memory T-cells, as it is thought not to have yet encountered cognate antigen in the periphery.

As used herein, the term "memory T-cell" is a specific type of infection-fighting T-cell that can recognize foreign invaders such as bacteria or viruses that were previously encountered by the cell during a prior infection or vaccination. At a second encounter with the invader, memory T-cells can reproduce to mount a faster and stronger immune response than the first time the immune system responded to the invader.

As used herein, the term "untouched" refers to cells that have not been bound by an antibody during cell isolation. Cell isolation often employs antibody to either positively or negatively select cells of interest. An "untouched" naïve T-cell refers to an isolated naïve T-cell that such antibody-isolation protocol is not employed (i.e., the isolated naïve T-cell has not been exposed to an antibody during the cell isolation).

As used herein, the term "GATA3" and "T-bet" refer to transcription factors in T-cells. GATA3 is recognized to participate in the transcription of multiple genes whose proteins are known to promote a Th2 response. T-bet is recognized to participate in the transcription of genes whose proteins are known to promote Th1 response.

As used herein, the term "homing receptor" refers to cell surface molecules that play an important role in lymphocyte trafficking between the blood compartment and the lymph compartment via the high endothelial venules. Homing receptors on pDC include, for example, "CD62L" (a.k.a. L-selectin) and "CCR7." While CD62L on DC primarily mediates migration of DC into lymphatic vessels, CCR7 primarily controls the migration of DC to inflamed tissues or compartments with secondary lymphoid organs.

As used herein, the term "co-stimulatory molecule" refers to a cell surface receptor (such as CD80, CD83, CD86 and ICOS-L [Inducible COStimulator Ligand/B7RP-1] that is present on the cell surface of antigen presenting cells (e.g., dendritic cells). The co-stimulatory molecules bind to specific receptors on immune cells (such as T-cells) to provide an excitatory or an inhibitory signal.

As used herein, the term "MLR" means a mixed lymphocyte reaction. In a MLR, T-cells from a blood donor are co-incubated with pDC from a different blood donor (i.e., allogeneic). One of ordinary skill in the art would optimize a MLR based on the classical MLR system detailed by Steinman R M et al. Proc Natl. Acad. Sci. U.S.A. 1978 October; 75(10):5132-6. pDC:T-cell ratio may range from 1:1 to 1:100. T-cells usually respond to the pDC and produce cytokines, which are released into the supernatant. Through the expression of specific co-stimulatory molecules (e.g., CD80, CD86, ICOS-L, CD83 and the like), pDC influence the T-cell response and cytokine production of T-cells. These co-stimulatory molecules bind receptors on T-cells and provide additional activation signals that may enhance or suppress cytokine production.

The present inventors surprisingly discovered that T-cells possess an IFN-λ receptor and that the T-cell function can be modulated by IFN-λ. To the best of inventors' knowledge, the present invention represents the first observation that IFN-λ can down-regulate the secretion of Th2 cytokines such as IL-4, IL-5 and IL-13 in peripheral blood mononuclear cells (PBMC). The present inventors discovered that this down-regulation of cytokine secretion is accomplished by a reduction in IL-4 and IL-13 mRNA and a decrease in the numbers of IL-4 and IL-13 positive $CD4^+$ T-cells. The present application relates to the discovery that IFN-λ decreases multiple Th2 cytokines, including IL-4, IL-5 and IL-13.

The present inventors also surprisingly discovered that treatment of isolated pDC (i.e., plasmacytoid dendritic cells; isolated using a negative cell selection process) with IFN-λ would significantly inhibit the ability of pDC to promote Th17 polarization. IFN-λ treatment may represent an important checkpoint for Th17 progression. The present inventors discover a method of using IFN-λ to treat isolated pDC as a therapy to attenuate intestinal inflammation and slow the progression of ulcerative colitis and Crohn's disease.

The present invention disclosed herein illustrates the hitherto unexpected ability of IFN-λ to modulate both the homing receptor molecules and co-stimulatory molecules on pDC. Without being bound by a theory, it is believed that IFN-λ modulation of these two types of molecules acts to dampen Th17 responses both separately and in concert.

During gut inflammation, there is a reduction in the numbers of circulating dendritic cells (DC) (including pDC and mDC). The reduction in blood DC corresponds to an increase of DC entering into the gut inflammation sites. Homing molecules present on DC may participate in the migration response, from the circulatory compartment to the gut compartment. DC is known to produce IL-23, which is required in an inflammatory bowel disease (IBD). Once present in the gut compartment, DC can stimulate Th17 cells and promote T-cell activation for chronic intestinal inflammation.

The present inventors first discovered that IFN-λ treatment alters the expression of the homing molecules on pDC. Specifically, IFN-λ treatment induces increases in CCR7 and CD62L on pDC. CCR7 is known to control the migration of memory T-cells to inflamed tissues, as well as stimulate dendritic cell maturation. CD62L is known to mediate pDC to leave the blood compartment and enter into secondary lymphoid tissues. We observed a greater increase in CD62L induced by IFN-λ treatment as compared to that of CCR7 (See, FIG. 16); thus suggesting that IFN-λ treatment overall would drive pDC to leave the blood compartment into the secondary lymphoid tissues.

Without being bound by a theory, the present inventors discovered that IFN-λ treatment alters the homing molecules on pDC and diminishes pDC's migration into the gut inflammatory sites. Instead, the IFN-λ treated pDC are directed to migrate from the peripheral blood circulation into the lymph nodes. This effect of IFN-λ therefore provides a powerful tool to divert pDC from entering into gut inflammatory sites and thereby inhibit the progress of inflammatory bowel diseases (such as Crohn's disease).

The present inventors also discovered that IFN-λ treatment alters the expression of co-stimulatory molecules on pDC. Specifically, IFN-λ treatment of isolated pDC induces an increase in CD80, CD83, ICOS-L on pDC, but no significant increase in CD86. These co-stimulatory molecules serve the function of stimulating T-cells to differentiate them as well as promote their production of various cytokines.

Without being bound by a theory, the present inventors believe that the IFN-λ treated pDC can no longer provide an excitatory signal that promotes T-cell proliferation and activation. This is evidenced by our finding that IFN-λ treatment, in a mixed lymphocyte reaction, reduces pDC's ability to influence T-cells to produce IL-17 (both IL-17A and IL-17F), thereby inhibiting the inflammatory process. Similarly, IFN-λ treatment reduces pDC's ability to influence T-cells to produce IFN-γ, IL-10 and IL-13.

It is believed that the Th17 responses require IL-23, which is shown to be critical in driving Th17 differentiation. During an intestinal inflammation event, IL-23 initiates and maintains Th17 cell activation and thereby promotes the inflammatory process. The present inventors discovered that IFN-λ treatment of pDC inhibits the Th17 responses (i.e., inhibiting T-cells ability to produce IFN-γ, IL-10 and IL-13, and IL-17). Therefore, IFN-λ exerts an effect that is opposite to that of IL-23. Unlike other investigators who choose to maneuver IL-23 as a therapy approach (e.g., neutralizing antibody against IL-23), the present inventors propose a therapy means of IFN-λ pretreatment of immune cells, which can achieve a better result by counter-balancing the deleterious effects of IL-23.

Accordingly, the present invention provides a method for treating the immune cells (i.e., PBMC) in an asthmatic patient with IFN-λ to down-regulate Th2 cytokines (e.g., IL-13, IL-4 and IL-5) in an attempt to ameliorate (i.e., inhibit) the severity of asthmatic diseases driven by a Th2 response. Such asthmatic diseases include, for example, allergic respiratory disorders, allergen-induced asthma and the like.

Accordingly, the present invention also provides a method for treating isolated pDC (isolated using a negative cell selection) in a patient who is suffering from inflammatory bowel diseases with IFN-λ to down-regulate, among other cytokines, Th17 cytokines (e.g. IL-17A and IL-17F) in an attempt to ameliorate the severity of inflammatory bowel diseases driven by a Th17 response. Such inflammatory bowel diseases, include, for example, ulcerative colitis, Crohn's disease and the like.

In one embodiment, the present method employs ex vivo treatment of peripheral blood mononuclear cells with IFN-λ. Those skilled in the art would appreciate that there are many established protocols for isolating PBMC from peripheral blood. Human peripheral blood may be drawn conveniently via venipuncture. Isolation of PBMC may be aided by density-gradient separation protocols, usually employing Ficoll-Hypaque or Histopaque. The PBMC isolation is performed under sterile conditions. Alternatively, cell elutriation methods may be employed to separate mononuclear cell populations. The advantages of the cell elutriation method include sterility and efficiency.

Isolated mononuclear cell populations include the lymphocytes such as T-cells. T-cells are often classified to include "helper" T-cell and "cytotoxic" T-cells, through the mutually-exclusive expression of the cell surface markers CD4 and CD8, respectively. It has become apparent that the T-helper response can itself be divided, according to whether it was polarized to support the development of hypersensitivity and antibody responses (i.e., "T-helper 2" or "Th2" cells), cell-mediated responses (i.e., "T-helper 1" or "Th1" cells) or inflammatory responses (i.e., "T-helper 17" or "Th17" cells). These polarized T-cells were defined according to certain signature cytokines produced upon stimulation. For example, Th1 cells produce IL-2 and IFN-γ, while Th2 cells produce IL-4, IL-5 and IL-13. Th1 and Th2 cells each arise from a precursor population (i.e., Th0 cell). Polarization to either Th1 or Th2 begins after activation through the T-cell receptor and is dependent upon signals received by the naïve T-cell. For example, if the T-cell is activated in the presence of IL-12, then the Th0 cell begins a process of Th1 maturation, wherein the IL-4 receptor ceases to be expressed on the surface, locking the cell to a Th1 pathway through activation of genes regulated by STAT-4, IFN regulatory and T-bet transcription factors. Conversely, cells activated in the presence of IL-4 down-regulate the IL-12 receptor and enter the Th2 pathway, activating the STAT-6, c-maf and GATA-3 transcription factors. In a similar fashion, cells activated in the presence of TGF-β and IL-6 polarize the cells towards Th17 differentiation, activating STAT3 and the RORγt transcription factor. In general, 100 mL of human peripheral blood can yield about $1 \times 10^8$ PBMC.

In one embodiment, the present invention provides a novel approach to purify or isolate pDC from PBMC. The approach involves the use of a negative cell selection. The isolated pDC attains a cell purity of at least >95% in accordance with the present protocol. The adopted negative cell selection process involves using beads (e.g., magnetic beads) that are coupled with monoclonal antibodies against different cell surface markers present in PBMC (but absent on pDC). One of ordinary skill in the art would recognize that pDC express unique cell surface molecules. Such technology, for example, involves the use of FACS. For purposes of this application, pDC is identified by FACS analysis with the following cell surface molecules: CD303 (BDCA-2)$^+$, CD304 (BDCA-4/Neutropilin-1)$^+$, CD123$^+$, and HLA-DR$^+$. However, pDC does not express CD3, CD11c CD14, CD16, CD19, CD20 or CD56.

To perform negative cell selection, we incubated PBMC ($1 \times 10^7$-$1 \times 10^8$ cells/mL in 2-10 mL) (total PBMC was obtained from ~250 mL whole blood) with a cocktail of beads (10 μL-100 μL/mL). Preferably, $5 \times 10^7$ cells/mL in ~2-10 mL PBMC was treated with 100 μL/mL. Each bead within the cocktail bears a specific monoclonal antibody against a specific cell surface marker in PBMC. Alternatively, PBMC may be incubated with a cocktail of monoclonal antibodies, with each monoclonal antibody specifically targeted against a cell surface marker on PBMC. Each antibody then is linked to a secondary monoclonal antibody which has specificity to dextran. Magnetic beads (50-150 nm) are coated with dextran, and added to the PBMC and antibody cocktail mixture.

After PBMC incubation of the beads, cells bound to the beads are removed (e.g., by a magnet). Monoclonal antibodies against different cell surface molecules are used to negatively select pDC. The concentration monoclonal antibody ranges from 10 ng/mL-5 μg/mL. Cell surface markers include: CD3 (to remove T-cells), CD20 (to remove B-cells), CD19 (to remove B-cells), CD56 (to remove monocytes and NK cells), CD16 (to remove monocytes and NK cells), CD14 (to remove monocytes), glycophorin A (to remove red blood cells). The use of such a cocktail of beads (coupled with various monoclonal antibodies) effectively removes T-cells, B-cells, NK cells, monocytes and red blood cells from PBMC. After the removal of beads, the process leaves behind a population of highly purified DC (i.e., both pDC and mDC).

Commercially available kits may be employed to perform negative cell selection to isolate DC. Such commercial kits include Miltenyi Biotec (Auburn, Calif.) and Stemcell Technologies (Vancouver, BC). pDC can further be negatively selected by incubating beads that are coupled with specific monoclonal antibodies against cell surface markers of mDC. For purposes of this application, mDC is identified by flow cytometry with the following cell surface molecules: HLA-DR$^+$, CD1a$^+$, CD11c$^+$, BDCA-1$^+$ or BDCA-3$^+$. The negative cell selection for pDC is made possible because pDC cells do not express CD1a, CD11c, BDCA-1 and BDCA-3. Instead, pDC expresses CD123$^+$, CD303$^+$, which represents the unique markers for these cells. Both mDC and pDC each constitutes about 0.2-0.5% of total PBMC.

To the best of the present inventors' knowledge, there is no available means to negatively select mDC. This is because mDC may share some of the aforementioned markers with T, B, NK cells and monocytes. For example, mDC shares the expression of CD11c and CD14 with monocytes. mDC also shares the expression of CD16 with NK cells. As such, using monoclonal antibodies against CD11c, CD14 and CD16 will inevitably remove mDC along with monocytes and NK cells from PBMC and hence decreases the mDC yield concomitantly. For at least these reasons, there has been no viable means (including commercial kits) to negatively isolate mDC.

The present inventors confirmed that negative cell isolation is insufficient and ineffective to purify mDC. In six (6) studies, we employed a cocktail of monoclonal antibodies targeted against specific cell surface molecules (i.e., CD3, CD16, CD20, CD19, CD56, CD14 and glycophorin A). Despite multiple best attempts and in each instance, after exposing PBMC ($1 \times 10^9$) with the cocktails, we recovered variable and small amount ($<1 \times 10^5$) of mDC. In addition, the cell population that contained mDC was a mixed cell population (<60% purity) as judged by their cell surface expression of HLA-DR, CD1a, CD11c, BDCA-1 or BDCA-3. Without being bound by a theory, it is believed the cocktails used during the negative cell selection also removed mDC, making it impossible to purify mDC. Accordingly, we were unable to purify mDC using a negative cell selection. It is unexpected that while our isolation methodology using negative cell selection is effective in isolating pDC, the same methodology is inapplicable for mDC.

Notably, isolation of pDC using positive cell selection has been reported. To perform positive cell selection, PBMC has been incubated with beads (for example, magnetic beads) that are coupled with monoclonal antibodies against CD303 (BDCA-2), Neuropilin-1 (BDCA-4) and CD85g (ILT7). These represent unique cell surface markers for pDC. After removing the unbound cells (for example, by a magnet), the bound pDC is isolated. While this approach can yield a pDC population of purity >95%, these positively-selected pDC are found to be unsuitable for studies. The present inventors, among other investigators, have discovered that the positively-selected pDC exhibit a decrease in cellular function, implying that the pDC have been stimulated during the positive cell isolation.

One of the hallmark features of pDC is the production of IFN-α upon viral stimulation (e.g. influenza virus and herpes simplex virus). In a series of studies, we reported that these positively-isolated pDC failed to fully produce IFN-α in response to viral stimulation. In contrast, negatively-isolated pDC retains full ability to produce IFN-α in response to viral stimulation. Without being bound by a theory, this observation is consistent with the speculation that cross-linking cell surface molecules during positive cell selection induces an activation signal to pDC, thereby dampening their ability to fully respond to a physiological stimulus following cell isolation. This observation further establishes the lack of feasibility of using positively selected pDC in any studies. The present inventors have discovered a negative cell selection that provides high yield of purity (e.g., >95%) and that these negatively selected cells could be used for therapeutic purposes.

Another form of positive selection for pDC involves the use of Fluorescence Activated Cell Sorting (FACS or "cell sorting"). In this procedure, monoclonal antibodies against pDC-specific markers are used to isolate pDC from PBMC. These monoclonal antibodies include, for example, CD303 (BDCA-2), Neuropilin-1 (BDCA-4) or CD85g (ILT7). These monoclonal antibodies are also coupled to a fluorescent molecule, which permits the isolation of pDC using a cell sorter. The present inventors have found that pDC isolated using cell sorting method exhibited a decrease in cellular function as evidenced by reduced IFN-α production following viral stimulation. This further confirms that pDC isolated using a positive cell selection is stimulated. Additionally, cell sorting isolation of pDC suffers from a high probability of contamination (e.g., bacteria or mycoplasma) and maintenance of sterility is difficult.

In one embodiment, the present invention relates to using IFN-λ to treat immune cells that are isolated from peripheral blood from a human. IFN-λ is a member of the Type-III interferon family which contains three members: namely, IFN-λ1, IFN-λ2 and IFN-λ3. The present method encompasses the use of any one of the three IFN-λ members or combinations thereof. These three proteins use the same unique hetero-dimeric receptor, comprised of the CRF2-12 (IFN-λ R1/IL-28Rα) chain and the CRF2-4 (IL-10-R-β) chains. As far as can be determined, IFN-λ, IFN-λ2 and IFN-λ3 are functionally synonymous. This receptor pair is not used by any other known ligand, although the CRF2-4 chain is also part of the IL-10, IL-22 and IL-26 receptors. Like their close relatives the Type-I interferons, IFN-λ1, IFN-λ2 and IFN-λ3 promote the phosphorylation of STAT1 and STAT2, induce the ISRE3 complex, elevate OAS and MxA expression, and exhibit an anti-viral activity in vitro.

Treatment of mononuclear cells with IFN-λ must be performed under strict sterile conditions. Freshly isolated mononuclear cells (about $1 \times 10^7$-$1 \times 10^9$ cells) are suspended in suitable culture medium to achieve a suitable cell concentration of about $1 \times 10^6$-$1 \times 10^7$ cells/mL. Alternatively, freshly isolated pDC cells (about $1 \times 10^5$-$1 \times 10^6$) suspended in suitable culture medium (1 mL) can be used to achieve a suitable cell number of about $1 \times 10^5$-$1 \times 10^6$ cells/mL). Exemplary media include RPMI and the like; optionally, the media may contain 2-10% heat-inactivated human serum albumin. IFN-λ is added to the culture media and incubation may be performed at a range of temperatures (e.g., 4° C., 25° C. or 37° C.). Preferably, the IFN-λ treatment occurs at 37° C. Suitable treatment duration can be conveniently optimized by one of ordinary skill in the art. Preferred treatment times include 1 hour to 24 hours. More preferred treatment times include 6 hours to 12 hours. Exemplary IFN-λ treatment doses include about 1 ng/ml to about 200 μg/ml. Preferably, the IFN-λ may be present at a concentration dosage of about 100 ng/mL to about 10 μg/mL.

One of skilled in the art would easily determine the optimal amounts of IFN-λ. With respect to PBMC, an optimal amount of IFN-λ that is effective in inhibiting stimulus-mediated release of IL-4, IL-5 and IL-13 from the mononuclear cells can be determined by established ELISA protocols. With respect to pDC, an optimal amount of IFN-λ that is effective in inhibiting stimulus-mediated release of IL-4, IL-5 and IL-13 from the mononuclear cells can be determined by established ELISA protocols.

IFN-λ treated immune cells may then be reintroduced back into the human patient. Without being bound by any particular theory, it is believed that the IFN-λ treated mononuclear cells, when in the human body, have the diminished capability to produce IL-4, IL-5 and IL-13. It is further believed that IFN-λ treated pDC, when in the human body, have the diminished capability to migrate into inflamed sites and produce less IFN-γ, IL-13, IL-10, IL-17.

Optionally, IFN-λ treated cells may be washed prior to administering into the same human subject from which the immune cells (e.g., mononuclear cells or pDC) were isolated (i.e., autologous). Washing medium is exemplified by PBS, HBSS, RPMI and the like. Without bound by a theory, washing procedure may remove any cell-released cytokines (e.g., IL-8) that may exert adverse effects in the human host body. Ideally, only the IFN-λ treated cells are administered back into a human. One of ordinary skill in the art would recognize that administering of cells in a human requires strict sterility conditions. Optimal amount of IFN-λ treated mononuclear cells may be administered. In one embodiment, about $1\times10^7$-$1\times10^9$ mononuclear cells are treated with IFN-λ and are administered back into patients. Preferred, about $1\times10^8$ cells mononuclear cells are used. Alternatively, optimal amounts of IFN-λ treated pDC may be administered. In one embodiment, about $1\times10^5$-$1\times10^6$ pDC are treated with IFN-λ and are administered back into patients. Preferred, about 1×10 cells mononuclear cells are used. Administration can be performed conveniently with the use of intravenous infusion tubing. Infusion may either be a bolus infusion or continuous infusion over a suitable time (e.g., 1 hour). Suitable infusion media include dextrose, saline or the like as known in the art.

The present invention utilizes the novel observation that IFN-λ has potent effects on Th2 responses by inhibiting the production of Th2 cytokines. Asthma disease is marked by an imbalance of Th1 or Th2 response (i.e., an elevated Th2 response) that actually leads to its exacerbation. For example, although asthma development is multi-factorial, Th2 cytokines are highly associated with the disease, especially IL-4, IL-5 and IL-13, secreted following antigen challenge in allergic asthma. Susceptibility to asthma in humans has been linked to the IL-4/IL-5/IL-13 locus on chromosome 5. In murine asthma models, airway hypersensitivity develops upon transfer of antigen-specific Th2, but not Th1 cells and IL-4$^{-/-}$ mice do not develop an allergic inflammatory response after airway challenge. In another embodiment, the present invention provides an ex vivo treatment of immune cells with IFN-λ followed by administering of IFN-λ treated immune cells back into the human, thereby inhibiting the immune cells' production of Th2 cytokine and thus alleviating the development and symptoms of asthma. Accordingly, the present invention is based on the premise that influencing the Th2 response in an asthmatic disease is beneficial to the outcome of disease.

The present inventors discovered that IFN-λ exerts potent immuno-modulatory effects on T-cells and their cytokine release during the Th1/Th2 T-cell responses.

One of ordinary skill in the art would conveniently assess if administration of IFN-λ-treated cells may improve a patient's asthmatic response. Standard Pulmonary Function Tests may be performed to determine if there is an improvement in lung function following administering of IFN-λ cells. One example includes the spirometry test where a spirometer is used to create a volume-time curve or flow-volume loop. The most commonly used guidelines for spirometric testing and interpretation are set by the American Thoracic Society. With the aid of a spirometer, pulmonary tests (e.g., Forced Vital Capacity (FVC) and Forced Expiratory Volume in 1 second ($FEV_1$)) can be measured. FVC represents the total amount of air that can forcibly be blown after full inspiration, measured in liters, and $FEV_1$ represents the amount of air that one can forcibly blow in one second, measured in liters. The ratio of $FEV_1$ to FVC provides an index if improved respiratory function occurs. A healthy adult has a $FEV_1$ to FVC value of ~75-80%.

The effectiveness of ex vivo treatment may be alternatively assessed by a diminution of blood Th2 cytokines (e.g., IL-13) level after administering of IFN-λ cells. The concentration of cytokines such as IL-13 can be conveniently assayed by an ELISA. Lung lavage fluid may also be obtained from a patient following IFN-λ-treated cell administration. Levels of Th2 cytokines (e.g., IL-13) may be determined by an ELISA. Other indications of improvement may include a decreased mucus production in the airway and morphological assay to verify a lesser bronchial inflammation (e.g., reduced infiltration of Th2 inflammatory cells into the airway of a patient). All of these parameters can be used individually or in combination to assess the effectiveness of ex vivo treatment. Based on this information, one of ordinary skill in the art would easily determine if an additional ex vivo treatment may be needed.

In yet another embodiment, PBMC can further be fractionated to enrich for T-cells. Furthermore, naïve T-cells and memory T-cells can be further purified using standard protocols, such as negative selection protocol using magnetic beads. The isolated T-cells, naïve T-cells, or memory T-cells can be treated with an effective amount of IFN-λ. An effective amount is an amount of IFN-λ that causes a reduction in the levels of IL-13, IL-4 and IL-5 in PBMC, naïve T-cells or memory T-cells.

In one embodiment, the mononuclear cells are further fractionated into T-cells and treated with an effective amount of IFN-λ. IFN-λ treated T-cells are then returned to the human patient. In another embodiment, naïve T-cells or memory T-cells are isolated and also treated with an effective amount of IFN-λ and returned to the human patient. Without being bound by any particular theory, it is believed that the IFN-λ treatment of T-cells, naïve T-cells, or memory T-cells is effective in inhibiting production of IL-4, IL-5, and IL-13 in the human patient.

The present invention encompasses various allelic variants of IFN-λ polypeptides insofar as they would inhibit the IL-4, IL-5 and IL-13 production and release, like that of a naturally-occurring IFN-λ polypeptides. The present invention also encompasses all three members of the IFN-λ: namely, IFN-λ1, IFN-λ2, and IFN-λ3.

In another embodiment, a human patient is treated ex vivo. Such a method comprises identifying a human patient in need of treatment (e.g., an asthmatic patient having a Th2 disease); removing PBMC from the patient and treating the PBMC with an effective amount of IFN-λ, and returning treated PBMC to the human patient. An effective amount will be an amount that causes a reduction in IL-13, IL-4 and IL-5 levels from the PBMC. The treated cells, when introduced back into the patient, provide relief of symptoms of the disease or disorder being treated.

The present method utilizes the novel observation that IFN-λ prevents the loss of homing receptor from T-cells (i.e., naïve and memory T-cells). Specifically, IFN-λ treatment inhibits the shedding of L-selectin (i.e., CD62L). L-selectin on T-lymphocytes plays a role in homing (i.e., transmigration from blood vessels into lymphatic vessels and further into lymph nodes). If L-selectin on T-cells is prevented from shedding, it would allow T-cell to undergo firm adhesion and transmigration. Once migrated into lymphoid tissue, L-selectin on T-cells is necessary for its homing into lymph nodes, where T-cells interact with dendritic cells and receive information therefrom.

Without wishing to be bound by a theory, the present inventors believe that IFN-λ's effect on blockade of L-selectin shedding in T-cells would alleviate symptoms associated with asthma (e.g., less mucus formation and eosinophil infiltration). By preventing L-selectin from shedding, IFN-λ treated T-cells can swiftly migrate into lymphoid organs. IFN-λ prevents Th2 cytokine-producing T-cells from being sequestered in asthmatic tissues (i.e., inflamed airways). With intact L-selectin, IFN-λ treated T-cells are expected to follow their normal migratory paths (i.e., migrate into lymphatic tissues and into lymph nodes). The IFN-λ treated T-cells are further expected to stay in the lymphoid tissues for a longer duration prior to their re-entry into the blood vessels. In the absence of IFN-λ treatment, T-cells would shed the L-selectin and accumulate into asthmatic inflamed tissues. As such, IFN-λ treatment is advantageous in that there is less expected infiltration of T-cells into asthmatic tissues. Notably, less T-cell infiltration translates into reduced local accumulation of IL-13 in inflamed airways.

IFN-λ also renders the T-cells to be less responsive to stimuli in terms of Th2 cytokine release. The combined effect of IFN-λ on T-cells is believed to be advantageous to alleviate the symptoms of asthma.

In another embodiment, the effectiveness of ex vivo treatment for pDC may be assessed by a diminution of T-cell derived cytokines (e.g., IL-13, IL-10, IL-17 or IFN-γ) level after treatment of IFN-λ with pDC. One convenient means to measure the effect is to adopt a mixed lymphocyte reaction. In the present MLR, pDC:T-cell ratio was 1:5. pDC and T-cells were derived from different donors (i.e., allogeneic). MLR experiments can be co-incubate for 3-6 days. At the end of the co-incubation period, supernatants (e.g., 100-500 μL aliquots) from the co-culture of mixed lymphocyte reaction can be easily obtained. The concentrations of cytokines such as IL-17 can be conveniently assayed by an ELISA. Indications of improvement after IFN-λ treatment of pDC may include a decreased incidence of flare-up and discomforts as indicated by the patients who receive the IFN-λ treatment therapy. Morphological evaluation may be conducted to verify a lesser gut inflammation (e.g., reduced infiltration of inflammatory cells into the gut of a patient). Alternatively, colonoscopy may be performed by a physician to ascertain the reduction of inflammatory lesions after the IFN-λ therapy. All of these parameters can be used individually or in combination to assess the effectiveness of ex vivo treatment. Based on this information, one of ordinary skill in the art would easily determine if an additional ex vivo treatment may be needed.

Further not wishing to be bound by a theory, the present inventors believe that IFN-λ's effect on pDC would alleviate symptoms associated with inflammatory bowel disease and asthma as well as other Th17-associated diseases. By altering homing receptors on pDC, IFN-λ treated pDC is diverted from migrating into a gut inflamed site, instead pDC can swiftly migrate into lymphoid organs. IFN-λ prevents Th17 cytokine-producing T-cells from being sequestered in an inflamed site of the gut as well as asthmatic tissues (i.e., inflamed airways). The IFN-λ treated pDC are further expected to stay in the lymphoid tissues for a longer duration prior to their re-entry into the blood vessels. In the absence of IFN-λ treatment, pDC would migrate out from the blood circulation and accumulate into gut and airway inflamed tissues. As such, IFN-λ treatment is advantageous in that there is less expected infiltration of pDC into asthmatic tissues. Notably, less pDC infiltration translates into reduced local accumulation of T-cells in inflamed airways.

IFN-λ also renders the pDC to be less responsive to stimulate T-cells in the context between dendritic cells and T-cells. Normal pDC allows the interaction with T-cells and stimulate them to release inflammatory cytokines, such as IL-13, IL-10, IL-17 and the like. The mechanism whereby IFN-λ treated pDC mediates this dampening effect is presently unknown.

The present invention provides a therapeutic means to purify pDC and alters its functions by pre-treatment with IFN-λ. The combined effect of IFN-λ on pDC (both on homing receptors and co-stimulatory molecules) is believed to be advantageous to alleviate the symptoms of inflammatory bowel disease and asthma.

In one embodiment, the present invention includes a combined treatment, whereby a human patient is treated ex vivo of mononuclear cells or T-cells or pDC, and a co-administration of IFN-λ. Accordingly, the present ex vivo method may be used in combination with IFN-λ administration.

In one embodiment, the ex vivo method is first performed. Specifically, PBMC from a human patient in need of treatment are isolated. The isolated PBMC are treated with an effective amount of IFN-λ, followed by administering the IFN-λ-treated PBMC back into the same human patient (i.e., autologous). Then, a second administration of IFN-λ will be performed with the same human subject. The second IFN-λ administration may be performed simultaneously, separately or sequentially with the ex vivo method (i.e., before or after the administration of ex vivo IFN-λ treated PBMC).

In one embodiment, the second administration of IFN-λ may be performed systemically, nasally, or orally. Alternative routes of administration include, but are not limited to, intranasal, subcutaneous and parenteral administration. IFN-λ may be administered alone or in admixture with a pharmaceutically acceptable carrier. The IFN-λ formulations may be provided using any formulation known in the art and appropriate for the route of administration. Such formulations may be as provided using the guidance of such resources as *REMINGTON'S PHARMACEUTICAL SCIENCES*, 18th ed., Mack Publishing Co., Easton, Pa. 1990. Exemplary formulation may include a solution that is isotonic with blood such as saline, Ringer's solution, or dextrose solution. Alternatively, non-aqueous vehicles such as fixed oils and ethyl oleate may be used, as well as liposomes. IFN-λ may conveniently be in the form of an aerosol spray. The spray may be coupled with a pressurized container, pump, or nebulizer with the use of a suitable propellant. Exemplary propellants include, but are not limited to, dichlorodifluoromethane, trichlorofluoromethane, hydrofluoroalkane and the like. The spray may contain ethanol and lubricants (e.g., sorbitan trioleate). It is appreciated that the daily dose with an aerosol will vary from patient to patient, and may be administered in a single dose or in divided doses.

Further, excipients may be included that improve the efficacy, receptor affinity, or half-life of the active ingredient. For example, but not by way of limitation, the IFN-λ of the methods of the invention may be pegylated (i.e., coupled with polyethylene glycol) by means well-known in the art to prolong the half-life of the active ingredient in the circulation. (See, e.g., Kozlowski et al. J. Control Release 72: 217-224, 2001). Such modification may enhance biological activity to be useful as therapeutic agents.

In one embodiment, the ex vivo IFN-λ-treated immune cells are returned to the human intravenously and a second dose of IFN-λ is administered parenterally. The IFN-λ- treated immune cells can be infused back into human via a bolus injection intravenously. Alternatively, the injection can be performed slowly over the course of hours. The IFN-λ parenteral administration can be performed intradermally, intranasally, etc. Preferably, the administering of ex vivo IFN-λ-treated cells may occur simultaneously with the second dose of IFN-λ administration. In one embodiment, the administrations may be repeated.

The following examples are provided to further illustrate various non-limiting embodiments and techniques. It should be understood, however, that these examples are meant to be illustrative and do not limit the scope of the claims. As would be apparent to skilled artisans, many variations and modifications are intended to be encompassed within the spirit and scope of the invention.

Materials and Methods

I) Human Subjects

Human peripheral blood mononuclear cells (PBMC) were isolated from buffy coats purchased from the Newark Blood Bank (Newark N.J.). These buffy coats were completely anonymous and it was not possible to identify the donors. PBMC were isolated by density-gradient centrifugation over Histopaque-1077 (Sigma, St. Louis).

II) Cell Preparation

PBMC were harvested by density gradient centrifugation over Histopaque within 24 hours of sampling. Cells were collected and washed twice in RPMI 1640 medium (Invitrogen, Grand Island, N.Y.). The cells were finally re-suspended at a final concentration of $1 \times 10^6$/mL in RPMI 1640 medium supplemented with 10% heat-inactivated fetal calf serum (FCS; GIBCO).

III) T-Cell Subsets Isolation

"Untouched" naïve CD4$^+$T-cells (CD3$^+$CD4$^+$CD45RA$^+$CD45RO$^-$) and memory CD4$^+$-cells (CD3$^+$CD4$^+$CD45RO$^+$) were prepared from PBMC using a negative magnetic separation kit (Stemcell Tech), according to the manufacturer's instructions. In brief, freshly isolated PBMC were incubated (room temperature, and 20 min.) with a cocktail of antibodies against CD8, CD14, CD16, CD19, CD20, CD36, CD56, CD123, TCRγ/δ, and glycophorin A (See, FIG. 5). Dextran-coated magnetic nanoparticles microbeads were added. Magnetically labeled cells were separated from unlabeled cells using a magnet device. The unlabeled cells constitute the memory T-cells. For naïve T-cell isolation, PBMC were incubated with biotinylated anti-CD45RO antibody first, followed by the addition of the cocktail of antibodies (i.e., CD8, CD14, CD16, CD19, CD20, CD36, CD56, CD123, TCRγ/δ, and glycophorin A). Separation of unlabeled cells (i.e., naïve T-cells) was performed as described above. The purities of the both memory T-cell and naïve T-cell populations were determined to be >95% (See FIG. 6A).

IV) Cell Culture Conditions

After washing, cells were adjusted to density of $1 \times 10^6$ cells/mL per well in 24-well flat-bottom plates. Cells were stimulated with microbeads coated with anti-CD2/CD3/CD28 ("beads", $5 \times 10^5$/mL, bead-to-cell ratio 1:2, Miltenyi biotech Inc., CA) in the presence or absence of 100 ng/ml IFN-λ1 (Peprotech, N.J.), in 1 ml cultures. For Th2 cell polarization, naïve CD4$^+$ T-cells were cultured in Th2 condition with CD2CD3CD28beads+10 ng/ml of IL-4 (Peprotech, N.J.). Supernatants were harvested at different time points as indicated, while cells were stored at −80° C. in lysis (Stratagene CA) buffer for RNA extraction. RPMI-1640 culture medium supplemented with 10% (v/v) heat-inactivated fetal calf serum was used throughout (complete medium).

V) Immunophenotype Analysis by Flow Cytometry

For immunophenotype analysis, PBMC, purified naïve or memory CD4$^+$ T-cells were quadruple stained with fluorescent-conjugated (FITC) mAbs (monoclonal antibodies) specific for cell surface markers and analyzed by flow cytometry using a FACSCalibur™. FITC-labeled anti-CD3, PE-labeled anti-CD45RA, PE-labeled anti-CCR7, PECy5.5-labeled anti-CD4 were purchased from eBioscience. FITC-labeled anti-lineage124 (IL-4Rα), PECy5-labeled anti-CD62L, APC-labeled anti-CD45RO were purchased from BD PharMingen. For surface staining, cells were incubated with the respective mAbs at 4° C. in the dark for 30 minutes. The cells were thereafter washed twice and fixed in 0.5% paraformaldehyde before acquisition.

VI) Quantitation of Secreted Cytokine by ELISA

Levels of accumulated IFN-γ and IL-13 were determined by ELISA from 24 hours and 3 day cultures. Antibody pairs for IFN-γ were purchased from eBioscience (CA) and for IL-13, from R&D Systems (MN). Manufacturers'protocol was followed and all washes were performed with phosphate-buffered saline (PBS) containing 0.05% (v/v) Tween-20 (Sigma). Briefly, flat-bottom, 96-well plates were coated with the appropriate capture antibody and incubated at 4° C. overnight in the dark. After washing, plates were blocked with 1% (w/v) bovine serum albumin (BSA; Sigma) then standards and culture supernatants were plated in triplicate. After incubation at 37° C. for 2 hrs, plates were washed, exposed to relevant biotinylated antibodies, then streptavadin-conjugated horse-radish peroxidase and finally to the chromogen, TMB. After 20 minutes, the reaction was halted by addition of sulphuric acid and the optical density at 450 nm determined. Cytokine concentrations were calculated from the standard curve present on each plate.

VII) Real Time Quantitative RT-PCR Analysis

Total RNA was extracted from cells (Stratagene CA) and cDNA prepared and subsequently assayed using a two-step procedure ("AffinityScript", Stratagene, CA). Quantitative (real-time) RT-PCR (qRTPCR) was carried out using a SYBRA Green method in a Stratagene MX-3000 instrument. cDNA samples were amplified thus: 10 minutes at 95° C. then 40 cycles of 95° C. 30 s, 60° C. 60 s, 72° C. 30 s. A melting curve analysis was carried out to verify that the Ct values were based upon a single PCR product. All primer concentrations were at 300 nM, except those for EF-1α (150 nM).

Primer pairs for cytokine analysis were:

```
                                       (SEQ ID NO: 4)
IL-28RαF    5' CCA GCC AGT CCA GAT CAC TCT 3'

(SEQ ID NO: 5)
IL-28RαR    5' ACA GCA GTA TCA GAA GCG ATG G 3'

(SEQ ID NO: 6)
T-betF      5' ACC ACC TGT TGT GGT C 3'

(SEQ ID NO: 7)
T-betR 5'   5' CCT TTC CAC ACT GCA C 3'

(SEQ ID NO: 8)
GATA3F      5' TCA AGG CAA CCA CGT C 3'

(SEQ ID NO: 9)
GATA3R      5' GAT GGA CGT CTT GGA G 3'
```

Relative levels of these cDNAs and the effect of IFN-λ1 were established using the ΔΔCt method against the housekeeping gene EF-1a:

```
                                                   (SEQ ID NO: 10)
    EF-1aF      5' CTG AAC CAT CCA GGC CAA AT 3'

(SEQ ID NO: 11)
    EF-1aR      5' GCC GTG TGG CAA TCC AAT 3'
```

VIII) Proliferation of CFSE-Labeled Naïve and Memory CD4+ T-Cells

Purified naïve or memory CD4$^+$ T-cells were re-suspended in complete RPMI 1640 medium at $10^7$ cells/mL. Carboxyfluorescein diacetate succinimidyl ester (CFSE; Invitrogen, Carlsbad, Calif.) was added at a final concentration of 5 μM, and the cells were incubated for 10 minutes at 37° C. in 5% $CO_2$. The stain was quenched using 5 times the volume of ice-cold complete RPMI 1640 medium for 5 minutes. The cells were then washed 3 times and re-suspended in complete RPMI 1640 medium before stimulating them with CD2CD3CD28 beads. After 6 days of culture, cells were acquired with FACSCalibur and analyzed using FlowJo software.

IX) Human Lymphoid Cells

Human peripheral blood mononuclear cells (PBMC) were isolated from anonymous buffy coats purchased from the Blood Center of New Jersey (East Orange, N.J.).

X) Cell Preparation and Culture Conditions

PBMC were harvested by centrifugation over Ficoll Paque (Sigma) within 24 hours of collection, by mixing buffy coats with serum-free RPMI 1640 medium (InVitrogen, Grand Island, N.Y.) at a 1:2 ratio, layering the mixture in a 2:1 ratio over Ficoll and spinning for 25 minutes at 425 g with no brake. Light density cells were harvested and washed twice in RPMI by spinning for 10 minutes at 300 g. Unless indicated, cells were resuspended at a final density of $1 \times 10^6$/mL in complete medium (RPMI 1640 medium supplemented with 10% (v/v) heat-inactivated fetal calf serum (FCS; GIBCO)) in 12- or 24-well plates. The following stimuli were added as indicated: HSV-1 (MOI=1, KOS strain)), IL-4 (100 ng/mL, R&D Systems Minneapolis, Minn.) IL-13 (100 ng/mL, R&D), Poly I:C (100 μg/mL, Sigma), LPS (100 ng/mL, Sigma), Concanavalin-A (ConA, 5 μg/mL, Sigma), IFN-α (1000 U/mL, PBL Piscataway, N.J.), Imiquimod (5 μg/mL, Invitrogen), CpG 2236 or 2247 (35 μg/mL, IDT Coralville, Iowa), PMA (10 μg/mL, Sigma), Ionomycin (1 μg/mL, Sigma) and IFN-λ1 (100 ng/mL, Peprotech Rocky Hill, N.J.). Th17 differentiation was achieved by incubating that indicated cells with IL-1b (2 ng/mL) and TGF-β (10 ng/mL; Humanzyme Chicago, Ill.) and IL-6 (Humanzyme, 10 ng/mL) for 6 days. Supernatants were collected after 24 hours and stored at −20° C.

XI) Dendritic Cell Isolation

"Untouched" pDC were negatively isolated using a commercial human pDC isolation kit (StemCell Technologies, Vancouver, BC), according to the manufacturer's instructions. Briefly, PBMC were re-suspended in PBS-0.1% bovine serum albumin (BSA; Sigma, St. Louis, Mo.) at a concentration of $5 \times 10^7$ cells/mL and incubated at room temperature for 30 minutes with i) Anti-Human CD32 (Fcγ RII) Blocker and ii) a proprietary cocktail of antibodies with specificities to all cellular subsets (including RBC and platelets) except pDC. The mixture was then incubated with magnetic particles for 5 minutes, after which the mixture was placed in a magnet for 5 minutes. Non-labeled cells were removed and counted. The resultant pDC populations were routinely 95%-98% pure as assessed by flow cytometric analysis using antibodies to the following: FITC-labeled anti-CD11c or Lineage cocktail (CD3, 14, 16, 19, 20, 56), anti-HLA-DR-PerCP, anti-CD123APC (Becton Dickinson-Pharmingen San Jose, Calif.), and PE-labeled anti-BDCA-1 or 2 (Miltenyi Biotec Auburn, Calif.), as described below.

XII) Receptor Cross-Linking on pDC (Positive Cell Selection)

Data (FIG. 13) shown are taken from a previous publication (see {Fanning et al., 2006, J Immunol, 177, 5829-39}). Briefly, CD4 and BDCA-4 on PDC were cross-linked using anti-CD4 and anti-BDCA-4 microbeads, respectively (Miltenyi Biotec). Briefly, PBMC were washed and re-suspended in MACS buffer. Anti-CD4 or anti-BDCA-4 microbeads (25 μL/$1 \times 10^7$ cells) were added and cells were incubated at 4° C. for 15 min. BDCA-2 was cross-linked on PDC using either biotinylated anti-BDCA-2 Ab (25 μL/$1 \times 10^7$ cells) or unlabeled anti-BDCA-2 Ab (10 μL/$1 \times 10^7$ cells). PBMC were incubated with primary Ab for 10 min. After washing in MACS buffer, anti-biotin microbeads (40 μL/$1 \times 10^7$ cells) or rat anti-mouse IgG1 microbeads (20 μL/$1 \times 10^7$ cells) (Miltenyi Biotec) were added and incubated for 15 min at 4° C. For CD123 cross-linking, anti-CD123 Ab (2 ng/$1 \times 10^6$ cells) (BD Pharmingen) was added to PBMC, incubated for 20 min at 4° C., and washed in MACS buffer, followed by incubation with rat anti-mouse IgG1 conjugated microbeads (Miltenyi Biotec) for 15 min at 4° C. Mouse IgG1 isotype control Ab (BD Pharmingen) with anti-IgG1 microbeads were used as a negative control for cross-linking. Following cross-linking, PBMC were washed and re-suspended in RPMI 1640, 10% FCS.

XII) CD4+ T-Cell Isolation

T-cells were isolated using the RosetteSep CD4$^+$ T-cell Isolation Kit from StemCell, according to the manufacturer's instructions. This kit allows CD4$^+$ cell isolation directly from whole blood, without the need to first isolate PBMC. Unwanted cells are labeled with Tetrameric Antibody Complexes at room temperature for 20 minutes, in order to ligate them to red blood cells (RBC) in a process known as "rosetting". This increases the density of the unwanted (rosetted) cells, such that they pellet along with free RBCs when centrifuged over Ficoll Paque as described above; highly enriched, non-rosetted T-cells are isolated from the interface, washed and counted. Purity of T-cells was assessed using the following fluorescently-labeled antibodies to the following cell surface receptors (eBioscience, San Diego, Calif.): CD3-FITC, CD45RA-PE, CD4-PeCy5 and CD45RO-APC.

XIII) Immunophenotype Analysis by Flow Cytometry

For immunophenotype analysis, PBMC were stained with one or more of the following fluorophore-labeled mAbs and analyzed by flow cytometry using a FACSCalibur™ (BD) machine and software packages from BD (CellQuest Pro) and Tree Star (FlowJo): Anti-CD83-FITC, anti-ICOS-L-PE, anti-CD3 FITC, anti-CD4 PeCy5.5 and anti-CCR7-PE were purchased from eBioscience. Anti-CD80-FITC, anti-CD62L-PECy5 and anti-CD86-APC were purchased from BD PharMingen. Cell surface expression of these receptors was analyzed on pDC and mDC present within the PBMC population; pDC were identified using FITC or PE-labeled anti-BDCA-2, APC labeled anti-CD 123 and PerCP-labeled anti-HLA-DR. mDC were identified using FITC or PE-labeled anti-BDCA-1 or BDCA-3 and PerCP-labeled anti-HLA-DR. Cells were washed with PBS-0.1% BSA, blocked with 5% (v/v) heat-inactivated human AB serum and incubated with the appropriate antibodies in the dark at 4° C. for 30 minutes, then washed twice in PBS and fixed in 1% paraformaldehyde.

XIV) Quantitation of Secreted Cytokine by ELISA

Levels of accumulated IL-17A, IL-17F, IFN-γ and IL-10 were quantified according to the manufacturer's instructions using kits from eBioscience, according to the manufacturer's instructions. IL-13 ELISA kits were purchased from R&D Systems (Minneapolis, Minn.). All washes were performed with PBS 0.05% Tween (Sigma). Optical density at 450 nm was determined using a VERSAmax spectrophotometer (Molecular Devices Sunnyvale, Calif.).

XVI) Real Time Quantitative RT-PCR Analysis

Total RNA was extracted from cells and cDNA prepared and subsequently assayed using the "AffinityScript" two-step procedure (Stratagene La Jolla, Calif.). Quantitative (real-time) RT-PCR (qRTPCR) was carried out using a SYBR Green method in a Stratagene MX-3000P instrument. cDNA samples were amplified thus: 10 minutes at 95° C. then 40 cycles of 95° C. 30 s, 60° C. 60 s, 72° C. 30 s. A melting curve analysis was carried out to verify that the Ct values were based upon a single PCR product. All primer concentrations were 150 nM. Primer pairs for cytokine analysis were:

```
                                          (SEQ ID NO: 4)
IL-28RαF  5' CCA GCC AGT CCA GAT CAC TCT 3'

(SEQ ID NO: 5)
IL-28RαR  5' ACA GCA GTA TCA GAA GCG ATG G 3'

(SEQ ID NO: 12)
IL-17A F  5' CTG.GGA.AGA.CCT.CAT.TGG.TGT.CAC 3'

(SEQ ID NO: 13)
IL-17A R  5' CGG.TTA.TGG.ATG.TTC.AGG.TTG.ACC 3'

(SEQ ID NO: 14)
IL-17F F  5' CCT.CCC.CCT.GGA.ATT.ACA.CTG.TC 3'

(SEQ ID NO: 15)
IL-17F R  5' CAG.GGT.CTC.TTG.CTG.GAT.GGG 3'
```

Relative levels of these cytokine cDNAs and the effect of IFN-λ1 was established using the ΔΔCt method against the housekeeping gene GAPDH:

```
                                          (SEQ ID NO: 16)
GAPDH F   5' TGC.ACC.ACC.ACC.TGC.TTA 3'

(SEQ ID NO: 17)
GAPDH R   5' GGA.TGC.AGG.GAT.GAT.GTT.C 3'
```

Example 1

Stimulation of Peripheral Blood Mononuclear Cells Causes Specific Cytokine Transcription: IFN-λ Lowers the mRNA Levels for IL-4 and IL-13

Human peripheral blood was obtained by venipuncture. Peripheral blood mononuclear cells (PBMC) were isolated using Ficoll-Hypaque gradient. PBMC were stimulated in vitro with Con-A, in the presence or absence of 100 ng/ml IFN-λ1 for 24 hours or 6 days. Then, $2\times10^6$ PBMC were incubated in 2 ml volume in 24-well plates. Total RNA was harvested and subjected to reverse transcription. The resulting cDNA was tested for the level of expression of IL-4, IL-5 and IL-13. EF-1a was used as the reference cDNA against which the Ct for the cytokine genes was established. Samples were run in triplicate. These ΔCts are plotted in FIG. 1. Results shown non-dotted lines were the ΔCts that were higher in the presence of IFN-λ1 (indicating less cytokine signal was present). Results were compared by the Wilcoxon test for non-parametrically distributed paired data. The data show that IFN-λ1 significantly diminished the level of IL-13 mRNA at both 24 hours (12/14 donors, 0.63×[0.37-0.87] (med+semi-interquartile range) versus no IFN-λ1 (ΔΔCt method) and 6 days (12/14 donors, 0.45×[0.17-0.91] versus no IFN-λ1. While not reaching statistical significance, 8/14 donors also showed a marked decrease in IL-4 mRNA levels at 24 hours. We observed that IFN-λ2 and IFN-λ3 also possessed similar inhibitory effects on mononuclear cells as compared to that of IFN-λ1.

Example 2

Stimulation of Peripheral Blood Mononuclear Cells Causes Specific Cytokine Release: IFN-λ Lowers Secretion of IL-4, IL-5 and IL-13, but not IFN-γ

Figure 2:
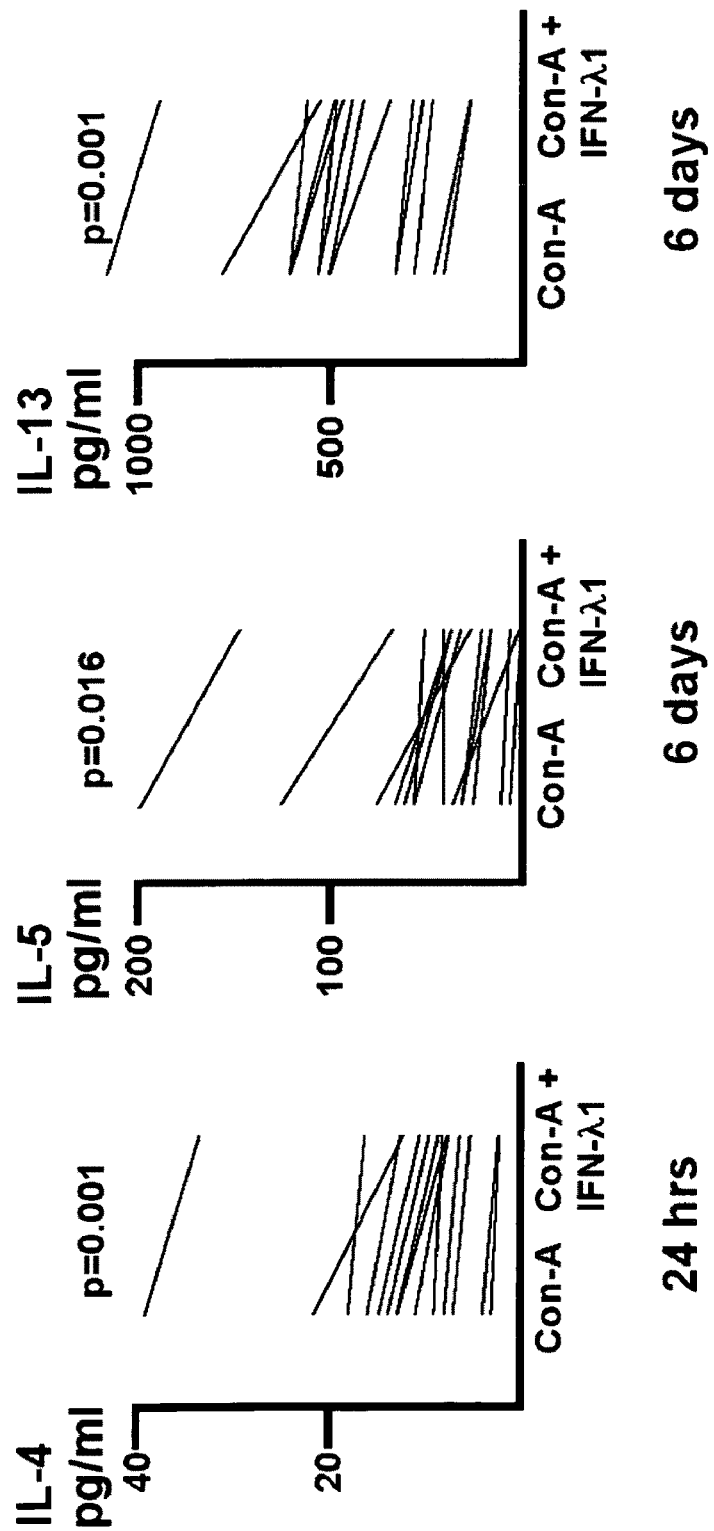
FIG. 2 shows that IFN-λ, lowers secreted levels of IL-4, IL-5 and IL-13. Panel A (IL-4 levels at 24 hours); Panel B (IL-5 levels at 6 days); Panel C (IL-13 levels at 6 days).

Supernatant fluid was harvested from the cultures described in Example 1 and tested for cytokine levels by ELISA (eBiosciences). Samples were run in triplicate. IFN-λ1, was observed to reduce cytokine secretion for IL-4 at 24 hours (14/14 donors, p=0.001), and IL-5 (13/14 donors, p=0.016) and IL-13 at 6 days (14/14 donors, p=0.001). Over all 14 donors, the level of IL-4, IL-5 and IL-13 were reduced by IFN-λ by 0.33×[0.25-0.38], 0.42×[0.27-0.49] and 0.22× [0.18-0.32], respectively. IFN-γ levels were not affected by IFN-λ1. The results of the study are shown in FIG. 2.

Example 3

IFN-λ Reduces the Number of IL-4, -5, -13 and IFN-γ Positive Cells CD4 T-Cells

Figure 3A:
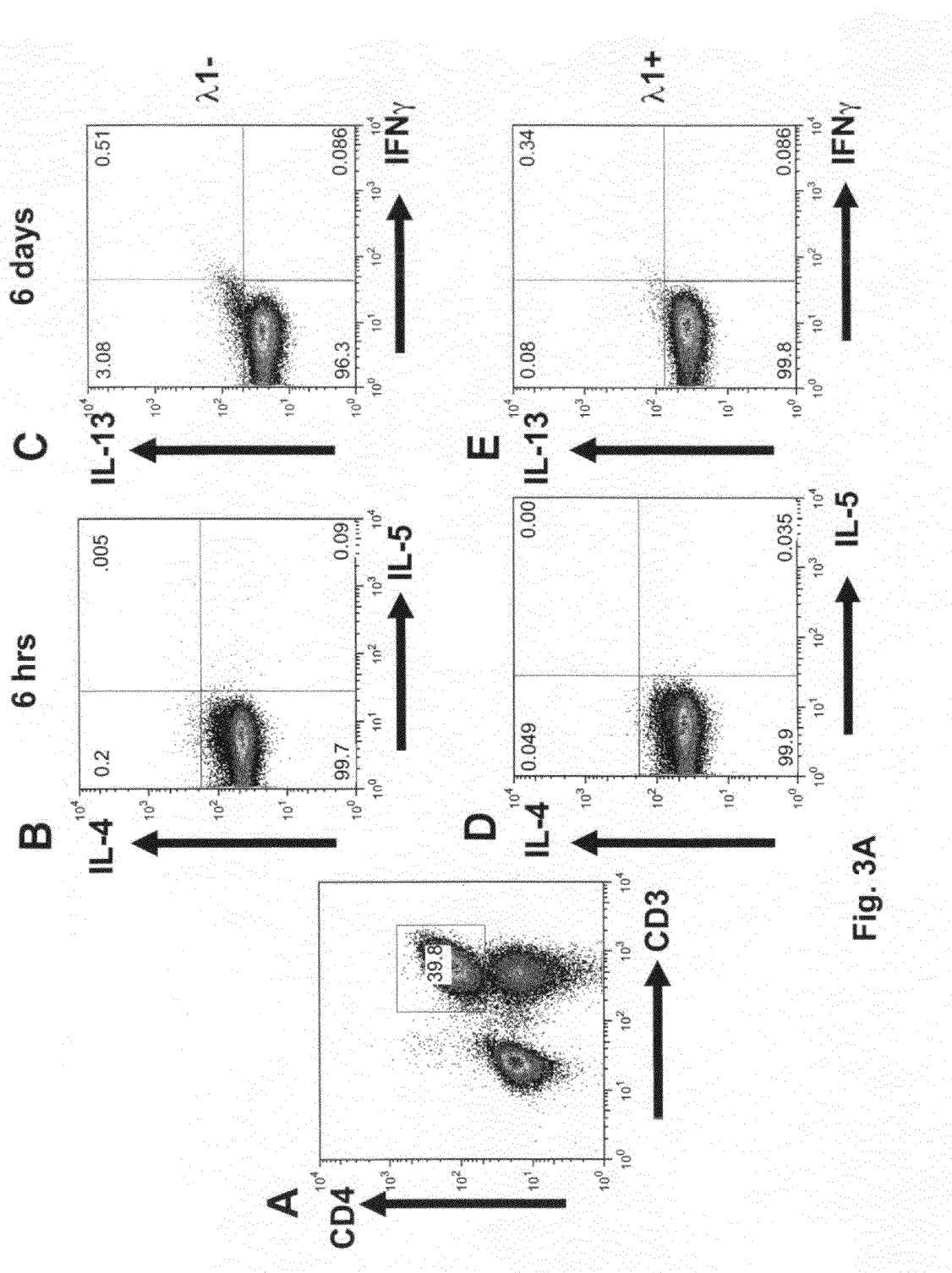
FIG. 3A shows that IFN-λ reduced the numbers of cytokine positive CD4 T-cells. Panel A, FACS analysis of $CD4^+$ and $CD3^+$ cells; Panel B, FACS analysis of $IL-4^+$ and $IL-5^+$ cells (6 hours without IFN-λ1 added); Panel C, FACS analysis of $IL-13^+$ and $IFN-\gamma^+$ cells (6 days without IFN-λ added); Panel D, FACS analysis of $IL-4^+$- and $IL-5^+$ cells (6 hours with IFN-λ, added); Panel E, FACS analysis of $IL-13^+$ and $IFN-\gamma^+$ cells (6 days with IFN-λ, added).
Figure 3B:
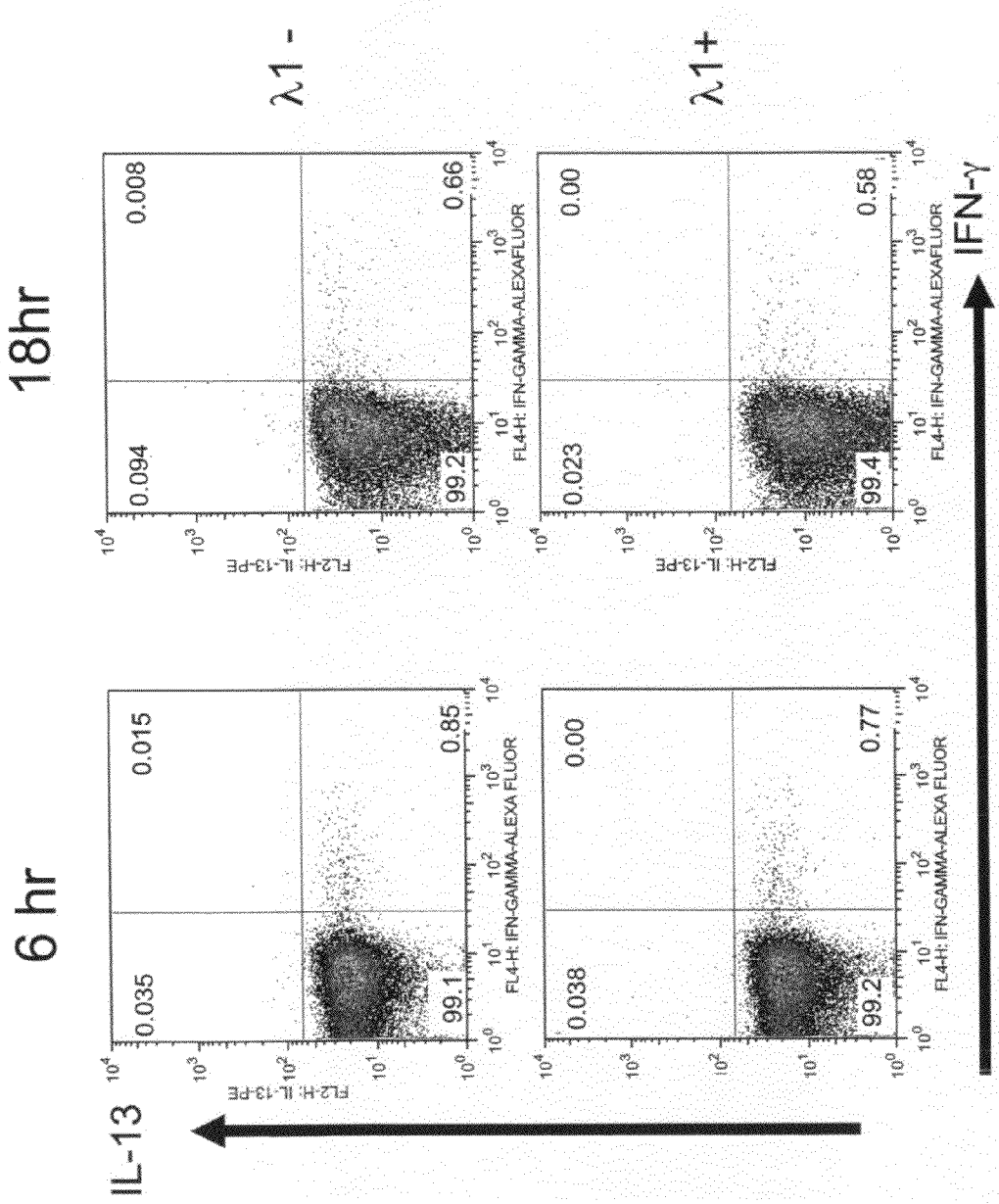
FIG. 3B shows that IFN-λ reduced the numbers of cytokine positive CD4 T-cells. The Time Course Study shows $IL-13^+$ and $IFN-\gamma^+$ cells with and without added IFN-λ. Top row, FACS analysis of cells not treated with IFN-λ over 6 hours, 18 hours, 48 hours, 72 hours and 6 days; bottom row, FACS analysis of cells treated with IFN-λ over 6 hours, 18 hours, 48 hours, 72 hours and 6 days.

FACS was used to evaluate the effects of IFN-λ1 on number of IL-4, IL-5, IL-13 and IFN-γ cells. As in Example 1, cells were incubated with IFN-λ1 for 6 hours or 6 days, with no re-stimulation. Cells were gated on the $CD4^+$ population and examined by FACS for positivity with intracellular IL-4, IL-5, IL-13 and IFN-γ. Antibodies were from eBiosciences or BD BioSciences. Although the numbers of stained cells were low, IFN-λ1 reproducibly diminished the number of $IL-4^+$ $CD4^+$ T-cells (by 75%, 56% and 46%, donors A-C) at 6 hours and of $IL-13^+$ CD4 T-cells (by 84%, 54%, 48%, 75%, 49% and 42%, donors A-E (See FIG. 3)). $IFN-γ^+$ $CD4^+$ T-cells were not altered by IFN-λ1. Notwithstanding the presence of $IFN-γ^+$ T-cells and the presence of $IFN-γ^-$ in the supernatant, cells progressed through to a population of $IL-13^+$, $IFN-γ^-$ cells (See FIG. 3B). In addition, we observed that IFN-λ is effective at decreasing the number of $IL-13^+$ $CD4^+$ cells when administered 24 hours before measurement at 6 days. Thus, IFN-λ1 may be used to treat existing asthma and other Th2-associated diseases.

In sum, the present inventors have discovered an unrecognized immuno-modulatory property of IFN-λ. Our inventors found that IFN-λ is capable of down-regulating the secretion of three major Th2 and asthma-associated cytokines: namely, IL-4, IL-5 and IL-13. The effect of IFN-λ is specific, because IFN-γ secretion was not affected. IFN-λ's effect in cytokine secretion was accompanied by mRNA reduction. This was significant for IL-13 at two time points and approached significance for IL-4 at 24 hours. Not wishing to be bound by any particular theory of operability, IFN-λ is believed to act in part by reducing Th2 cytokine transcription in activated cells.

The present inventors further observed that IFN-λ decreases the number of $IL-13^+$, $CD4^+$ T-cells, as well as IL-4 positive $CD4^+$ T-cells without altering the numbers of IFN-γ cells, demonstrating a preferential, modulating effect on the Th2 system. Without wishing to be bound by any theory, IFN-λ is proposed to diminish the secretion of IL-4 and IL-13, the principle cytokine mediator of asthma and associated Th2 cytokines in healthy individuals, perhaps by a mechanism governing control of the "Th2 locus" on chromosome 5.

Example 4

IFN-λ1 Inhibits IL-13 Production and Gives Rise to IFN-γ Production in PBMC In Example 2, we showed that IFN-λ1 modulates IL-13 (representative of Th2 responses) with little impact on IFN-γ production (representative of Th1 responses) following mitogen (i.e., Concanavalin A) stimulation of PBMC. Here, a physiologically relevant stimulation was adopted using anti-CD2/3/28 coated MACS iBeads ("beads") to stimulate T-cells directly through their T-cell receptor complex, with appropriate co-stimulation. PBMC were stimulated with beads for 3 days in the presence or absence of IFN-λ1. We observed that IFN-λ1 inhibited IL-13 production and elevated IFN-γ levels.

Figure 4:
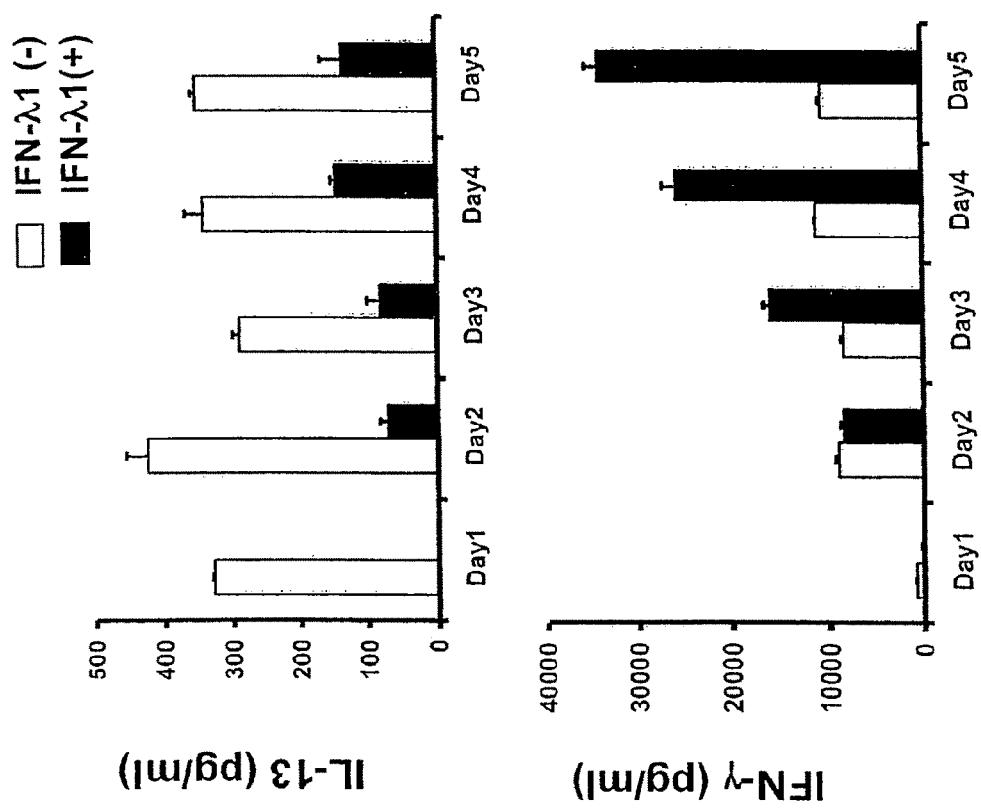
FIG. 4 shows that IFN-λ inhibited the release of IL-13. PBMC were isolated and stimulated with anti-CD2/3/28 coated beads for various days. IFN-λ completely blocked the IL-13 production at day 1, and consistently reduced IL-13 from day 2 to day 5. IFN-λ delayed the IFN-γ production.

To determine whether IL-13 production was inhibited by IFN-λ1 directly (produced early, in response to the bead stimulation), a daily time-course for this experiment was undertaken. IFN-λ1 blocked IL-13 production completely at day 1, with consistent reductions from day 2 to day 5 (56.8%-82.9% inhibition, FIG. 4). In contrast, we did not find any differences in IFN-γ production by IFN-λ1 treatment at day 1 and day 2. Thus, IFN-λ1 acted primarily to inhibit the production of IL-13. The subsequent rise in IFN-γ was therefore likely a consequence of the reduction of Th2 cytokines. Given that the stimulation used was specific for T-cells, we hypothesized that IFN-λ1 was acting directly on T-cells to inhibit IL-13 production.

Example 5

Figure 5:
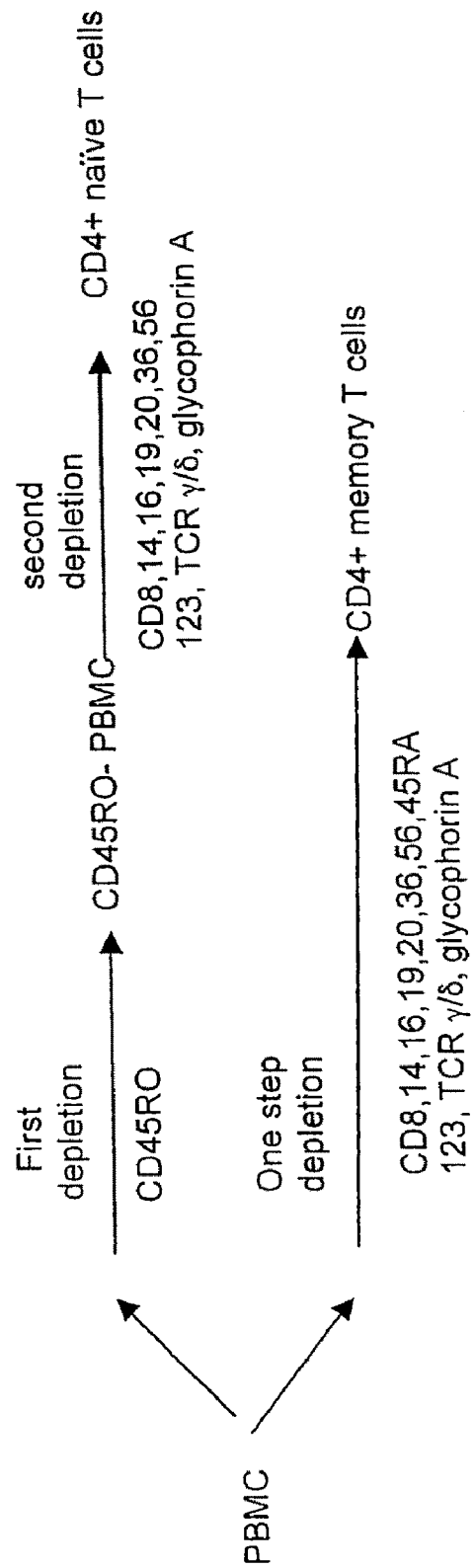
FIG. 5 shows the isolation protocol for naïve and memory T-cells from human peripheral blood using a magnetic separation kit.
Figure 6A:
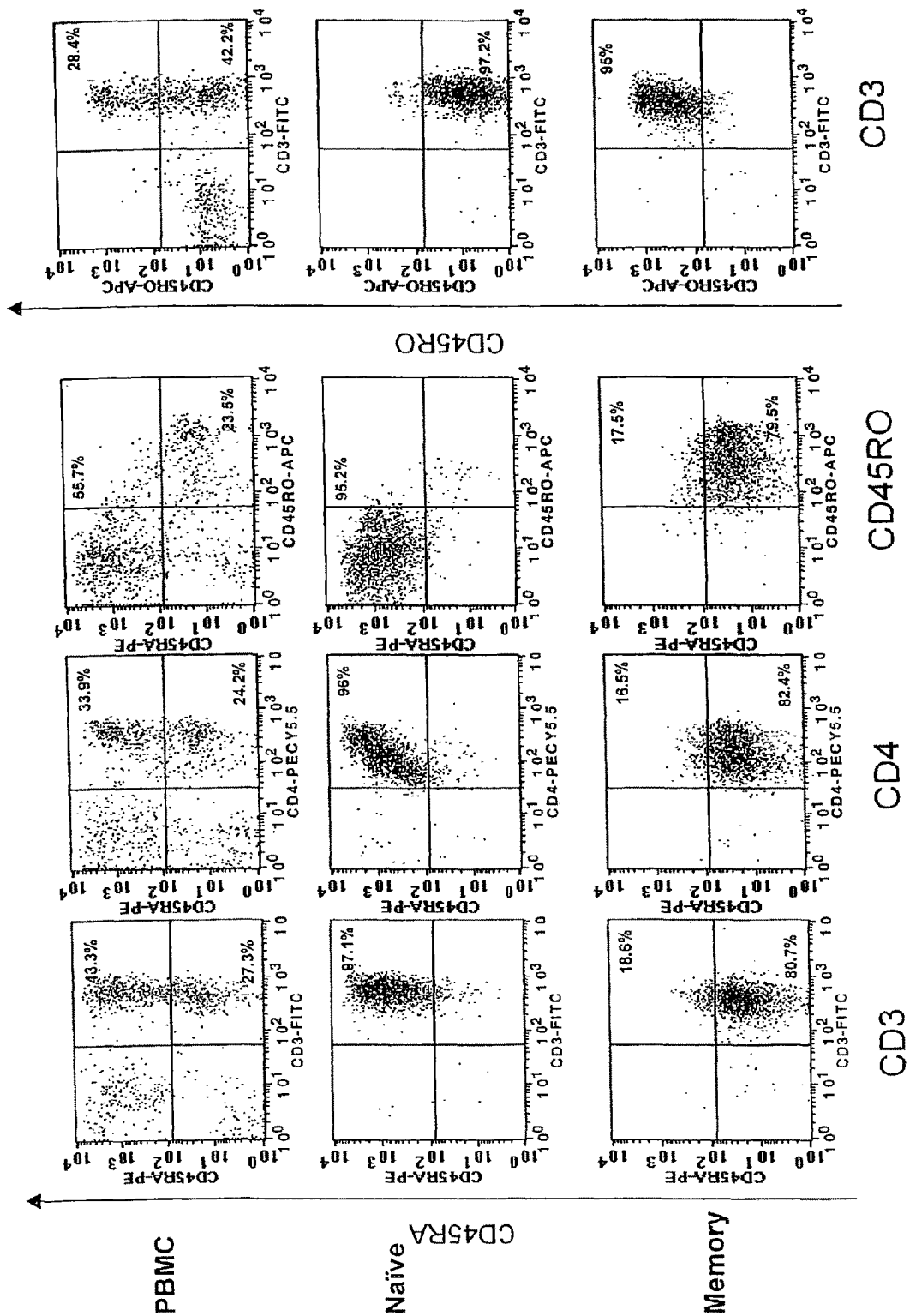
FIG. 6A shows FACS analysis of purified naïve and memory $CD4^+$ T-cells after isolation using negative isolation protocol. More than 95% of the naïve T-cells were $CD3^+CD4^+CD45RA^+CD45RO^-$ cells. More than 95% of the memory T-cells were $CD3^+CD4^+CD45RO^+$ cells, with a small proportion expressing both CD45RO and CD45RA.
Figure 6B:
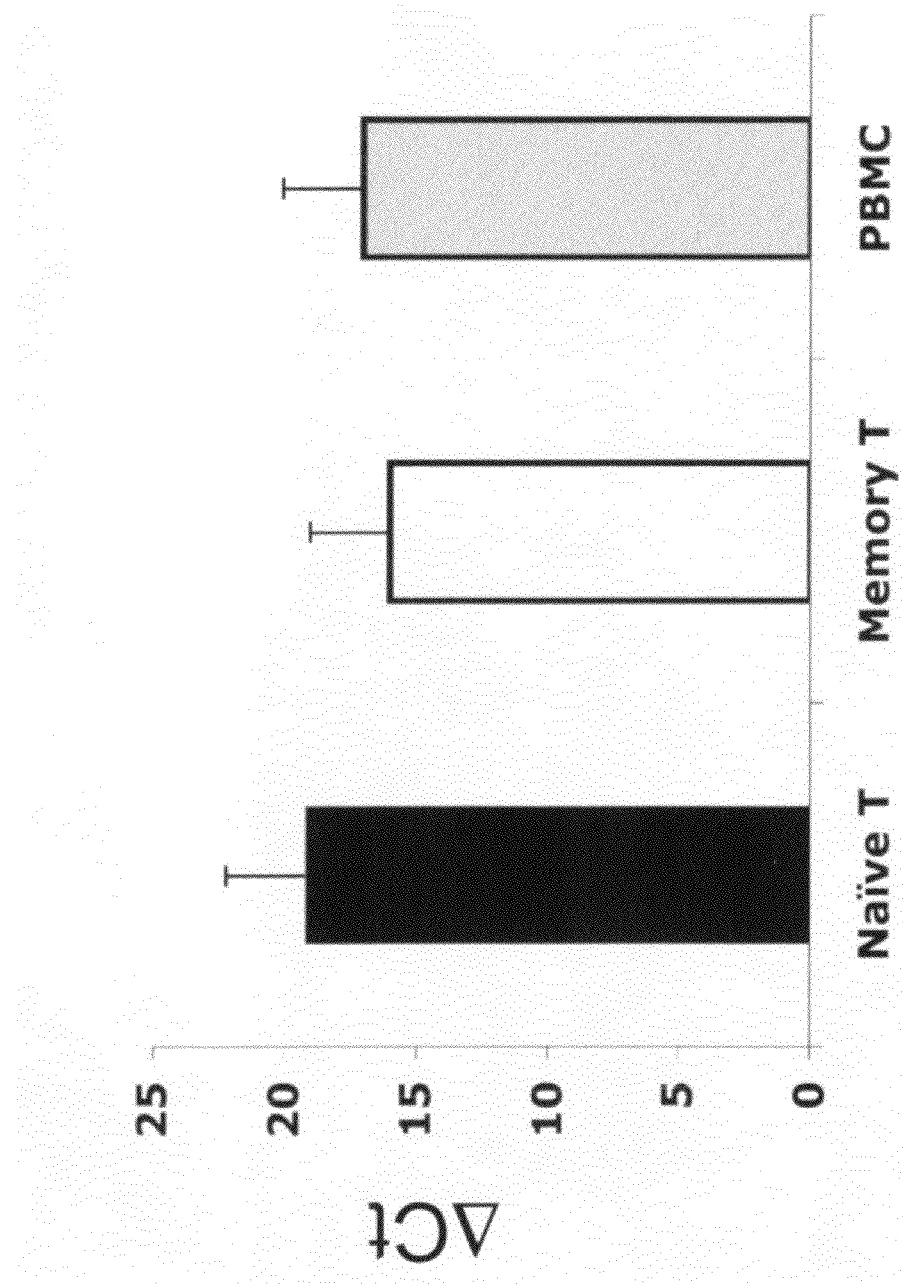
FIG. 6B shows the ΔCT of IFN-λ (IL28Rα) mRNA expression in PBMC, naïve and memory T-cells.

IFN-λ1 Receptor IL-28Rα is Expressed on Both Naïve and Memory CD4$^+$ T Cells In order to identify IFN-λ1-responsive cell types in human PBMC, we assayed various cell types for the presence of the IFN-λ1 receptor (IL-28Rα) mRNA by qRT-PCR. "Untouched" populations of naïve and memory CD4$^+$ T-cells were purified using negative isolation (FIG. 5). More than 95% of the naïve T-cells were CD3$^+$CD4$^+$CD45RA$^+$ CD45RO$^-$ cells. Greater than 95% of the memory T-cells were CD3$^+$CD4$^+$CD45RO$^+$ cells, with a small proportion (18.6%) expressing both CD45RO and CD45RA (FIG. 6A). FIG. 6B shows the ΔCT of IL-28Rα mRNA expression in PBMC, naïve and memory T-cells. Using this approach, higher ΔCT values signify lower mRNA expression levels. The highest values were found in CD4$^+$ naïve T-cells, indicating a lower level of IL-28Rα expression on this population. Interestingly, memory CD4$^+$ T-cells expressed higher amounts of IL-28Rα mRNA levels than naïve cells, approaching that of PBMC. These data lend strong support to the hypothesis that IFN-λ1 has the ability to act directly on multiple CD4$^+$ T-cell populations.

Example 6

Figure 7A:
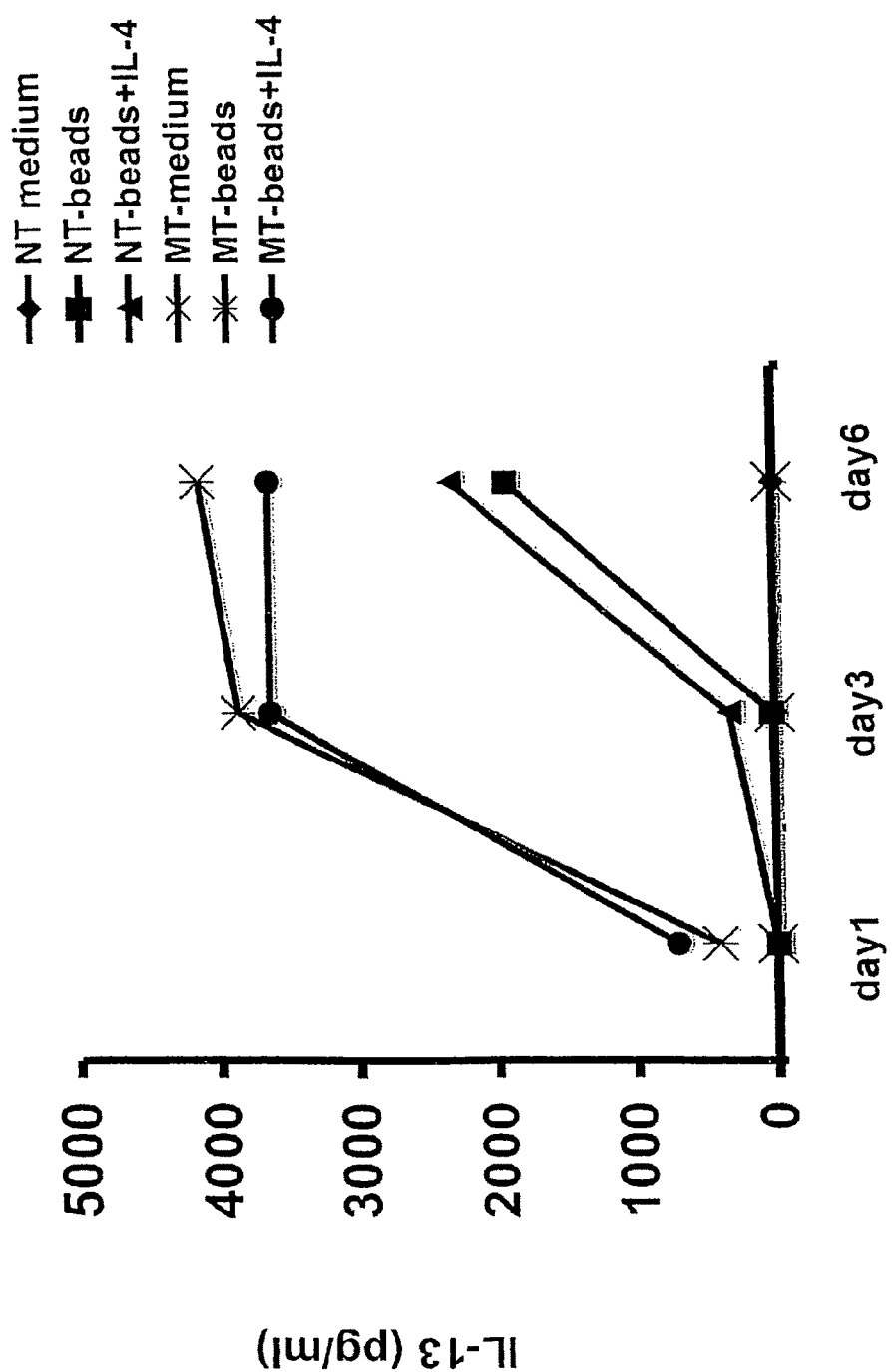
FIG. 7A shows the effect of IL-4 on naïve and memory $CD4^+$ T-cells to produce Th2 cytokine IL-13. Purified naïve and memory T-cells from the same donor were stimulated with anti-CD2/3/28 beads under neutral (beads only) or Th2 conditions (beads+IL-4).

Differential Effects of IL-4 on IL-13 Production in Naïve and Memory CD4$^+$ T-Cells To determine the capacity of naïve and memory CD4$^+$ T-cells to produce the Th2 cytokine IL-13 in the presence of IL-4 (i.e., under Th2 conditions), highly purified naïve and memory T-cells from the same donor were stimulated with anti-CD2/3/28 beads under neutral (beads only) or Th2 conditions (beads+IL-4). At different time points (days 1, 3 and 6), the supernatant was collected and IL-13 production was examined by ELISA. As shown in FIG. 7A, naïve T-cells did not produce IL-13 immediately at day 1, and produced less at day 3 than memory cells were producing on day 1; as expected, memory T-cells produced a large amount of IL-13 from day 1, reaching peak levels at day 3. Interestingly, IL-4 specifically increased IL-13 production by naïve T-cells, but did not affect IL-13 production by memory T-cells at day 1 and day 3, and actually slightly inhibited their IL-13 production at day 6.

Example 7

Figure 7B:
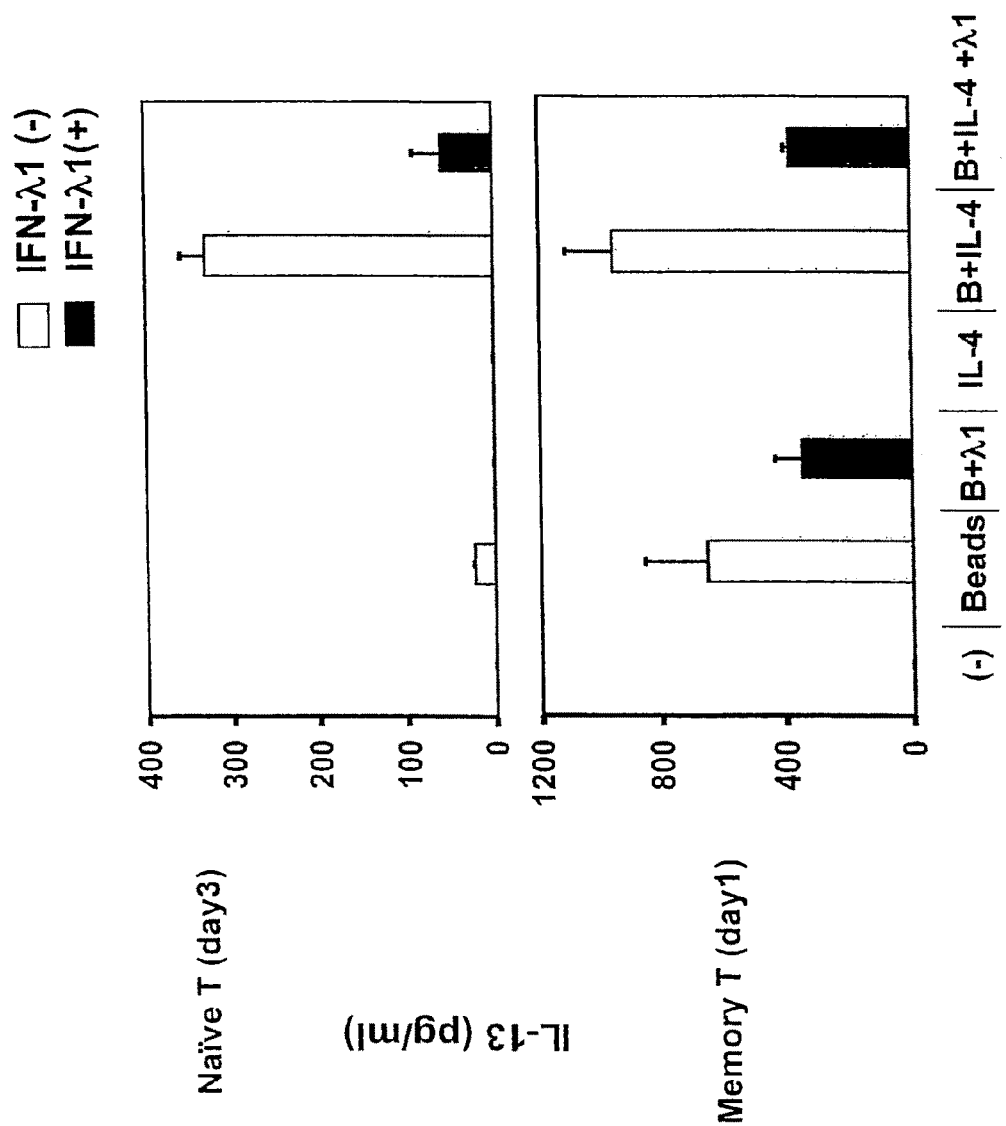
FIG. 7B shows the effect of IFN-λ in reducing IL-13 production in both naïve and memory T-cells.
Figure 7C:
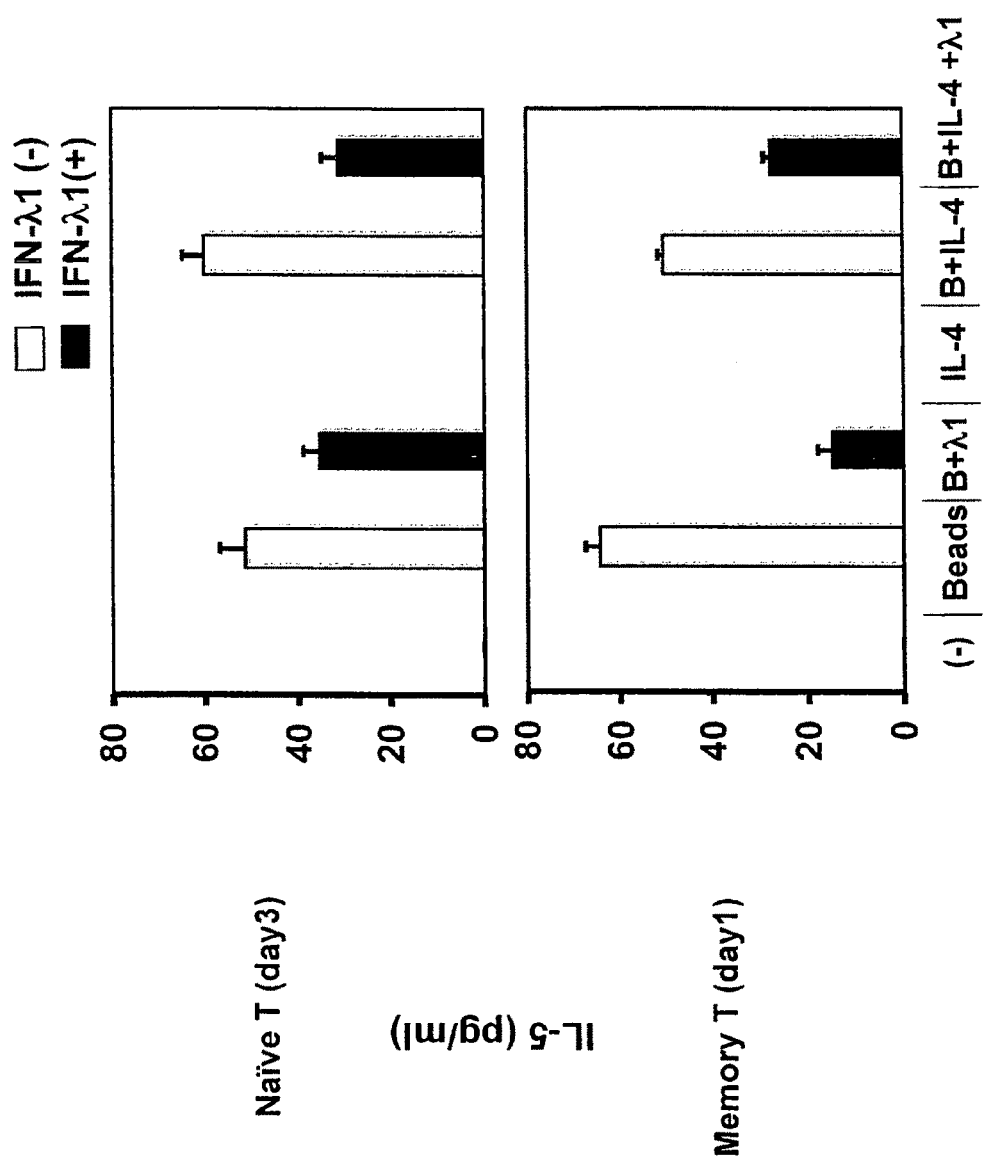
FIG. 7C shows the effect of IFN-λ in reducing IL-5 production in both naïve and memory T-cells.

IFN-λ1 Directly Inhibits Th2 Cytokine Production by Either Naïve or Memory T-Cells Given that both naïve and memory cells expressed IL-28Rα (FIG. 6B), we next characterized the direct effect of IFN-λ1 on Th2 cytokine production. In the absence of other cell types, purified naïve or memory CD4$^+$ T-cells were stimulated under neutral (beads alone) or Th2 conditions (beads+IL-4), in the presence or absence of IFN-λ1. Supernatants were assayed by ELISA for the Th2 cytokines IL-13 and IL-5. As shown in FIGS. 7B and 7C, naïve CD4$^+$ T-cells did not produce any Th2 cytokines at day 1 (data not shown); only after the cells were driven towards a Th2 phenotype did they produce IL-13 and IL-5 (day 3 or day 6). Likewise, IL-4 significantly enhanced IL-13 production by naïve T-cells. Notably, this increased IL-13 production was greatly reduced by IFN-λ1, suggesting it may act specifically to antagonize the activity of IL-4. In contrast, under the same Th2 polarizing conditions, IL-13 and IL-5 production were induced in memory T-cells immediately after overnight stimulation. Interestingly, IFN-λ1 immediately inhibited their IL-13 and IL-5 production under both neutral and Th2 conditions. Similar inhibitions were seen at day 3, and less of an effect was observed at day 6, (data not shown).

In sum, IL-13 and IL-5 secretion was inhibited by IFN-λ under neutral and Th2 conditions, in naïve and memory CD4$^+$ T-cells. This occurred independently of a rise in Th1-associated cytokines, and was also observed in the presence of neutralizing antibody to IFN-γ.

Example 8

Figure 8A:
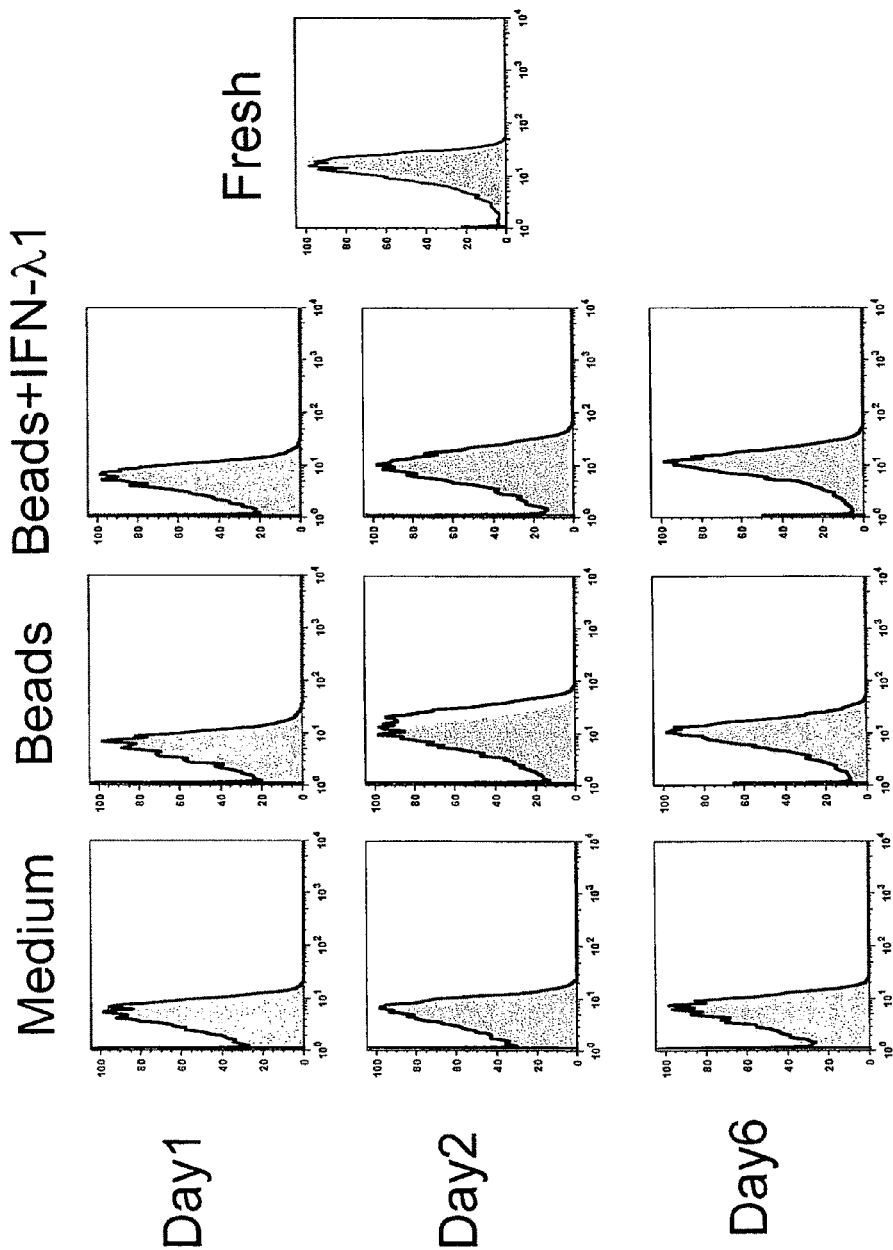
FIG. 8A shows expression of IL-4Rα on freshly isolated naïve $CD4^+$ T-cells following stimulation with anti-CD2/3/28 beads.
Figure 8B:
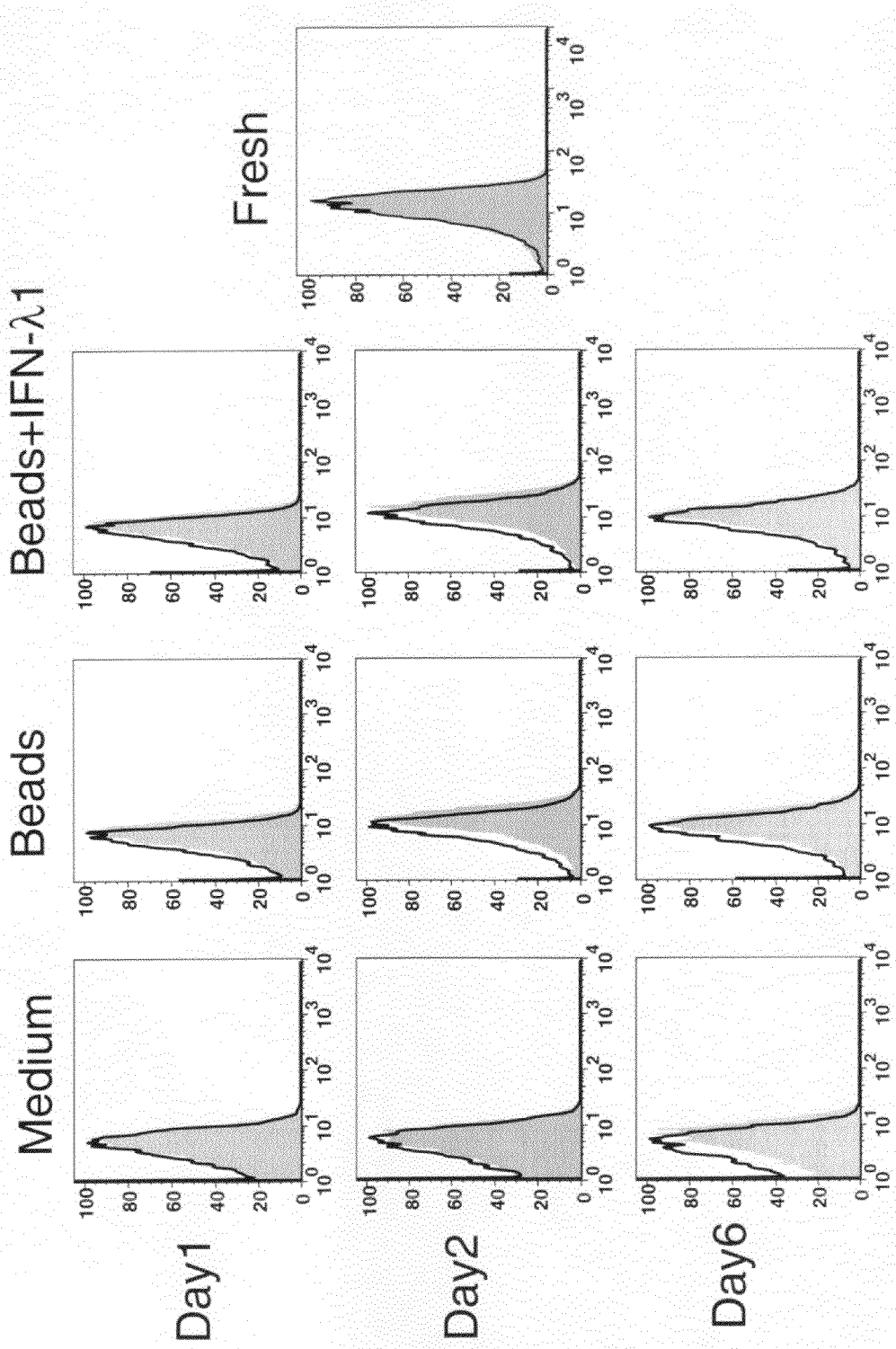
FIG. 8B shows expression of IL-4Rα on freshly isolated memory $CD4^+$ T-cells following stimulation with anti-CD2/3/28 beads. Following bead stimulation, only naïve T-cells express IL-4Rα, which was down-regulated by IFN-λ.

Differential Expression of IL-4Rα on Naïve and Memory T-Cells and the Effect of IFN-λ1 on IL-4Rα Expression To determine whether IFN-λ1 specifically antagonized the activity of IL-4 on naïve T-cells through the regulation of the IL-4 signaling pathway, IL-4Rα expression on naïve and memory T-cells was measured by flow cytometry, with or without stimulation, in the presence or absence of IFN-λ1 at different time points. As shown in FIGS. 8A and 8B, freshly isolated naïve and memory CD4$^+$T-cells did not express IL-4Rα on their surface. However, IL-4Rα expression was detected after 48 hr stimulation with anti-CD2/3/28 beads, but only on naïve T-cells. Remarkably, naïve T-cells that were stimulated in the presence of IFN-λ1 did not express detectable cell-surface expression levels of IL-4Rα, suggesting that IFN-λ1 down-regulated, or prevented, the expression of IL-4Rα. In contrast, IL-4Rα expression was not detectable on memory T-cells with or without stimulation, in any culture conditions through the whole culture period (6 days), which is consistent with our observation that IL-4 was not required for IL-13 production by memory CD4$^+$ T-cells.

Example 9

IFN-λ1 Regulates Expression of GATA3 and T-Bet

We next addressed whether downstream signaling can be modulated by IFN-λ1. As widely recognized, the polarized cytokine profiles of Th1 and Th2 cells are primarily dictated by the mutually exclusive expression of the "master" Th1 and Th2 transcription factors, T-bet and GATA3. IL-4 stimulation through the IL-4R leads to phosphorylation of STAT6 and upregulation of GATA3 expression, while IL-12 and IFN-γ perform the complementary function of upregulating T-bet.

Figure 9:
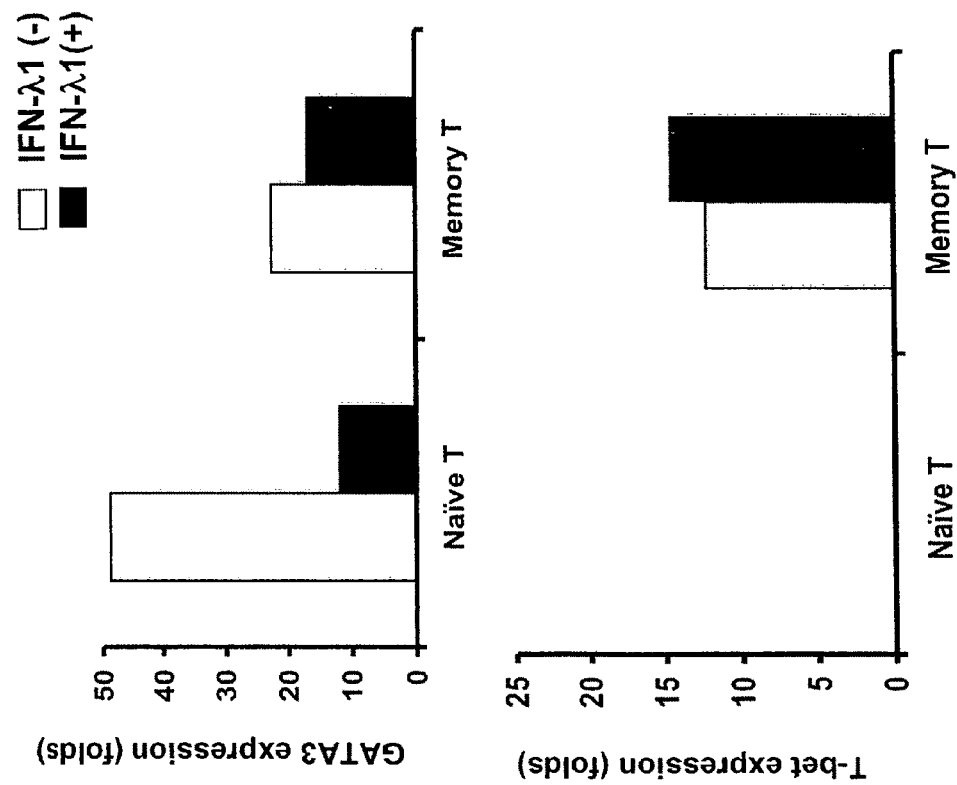
FIG. 9 shows GATA3 and T-bet expression in purified naïve and memory $CD4^+$ T-cells following Th2 conditions (i.e., beads+IL-4) for 18 hours. IFN-λ1 inhibited the expression of GATA3 expression (as measured by qRT-PCR) 4-fold in naïve T-cells. Memory T-cells exhibited only small changes in either GATA3 or T-bet expression.

In these experiments, purified naïve or memory CD4$^+$ T-cells were stimulated under Th2-polarizing conditions (beads+IL-4) for 18 hr, in the presence or absence of IFN-λ1. RNA was harvested for qRT-PCR quantitation of T-bet and GATA3 expression. As shown in FIG. 9, expression of GATA3 by naïve T-cells was decreased 4-fold (3-6 fold, depending on the donor) upon treatment with IFN-λ1. As expected, T-bet expression was barely detectable under Th2 conditions. Memory T-cells on the other hand, exhibited only small changes in either GATA3 or T-bet expression. Considering the heterogeneous composition of memory CD4$^+$ T-cells, it is possible that the presence of non-Th2 polarized or non-Th1 polarized has diminished our ability to measure any changes in GATA3 or T-bet expression. Nonetheless, these data strongly support the direct inhibition of Th2 polarization by IFN-λ1, through the regulation of the Th2-restricted transcription factor GATA3, and that this effect is most pronounced in naïve CD4$^+$ T-cells.

Example 10

IFN-λ1 does not Modulate the Proliferation of Naïve CD4$^+$ T-Cells

Figure 10:
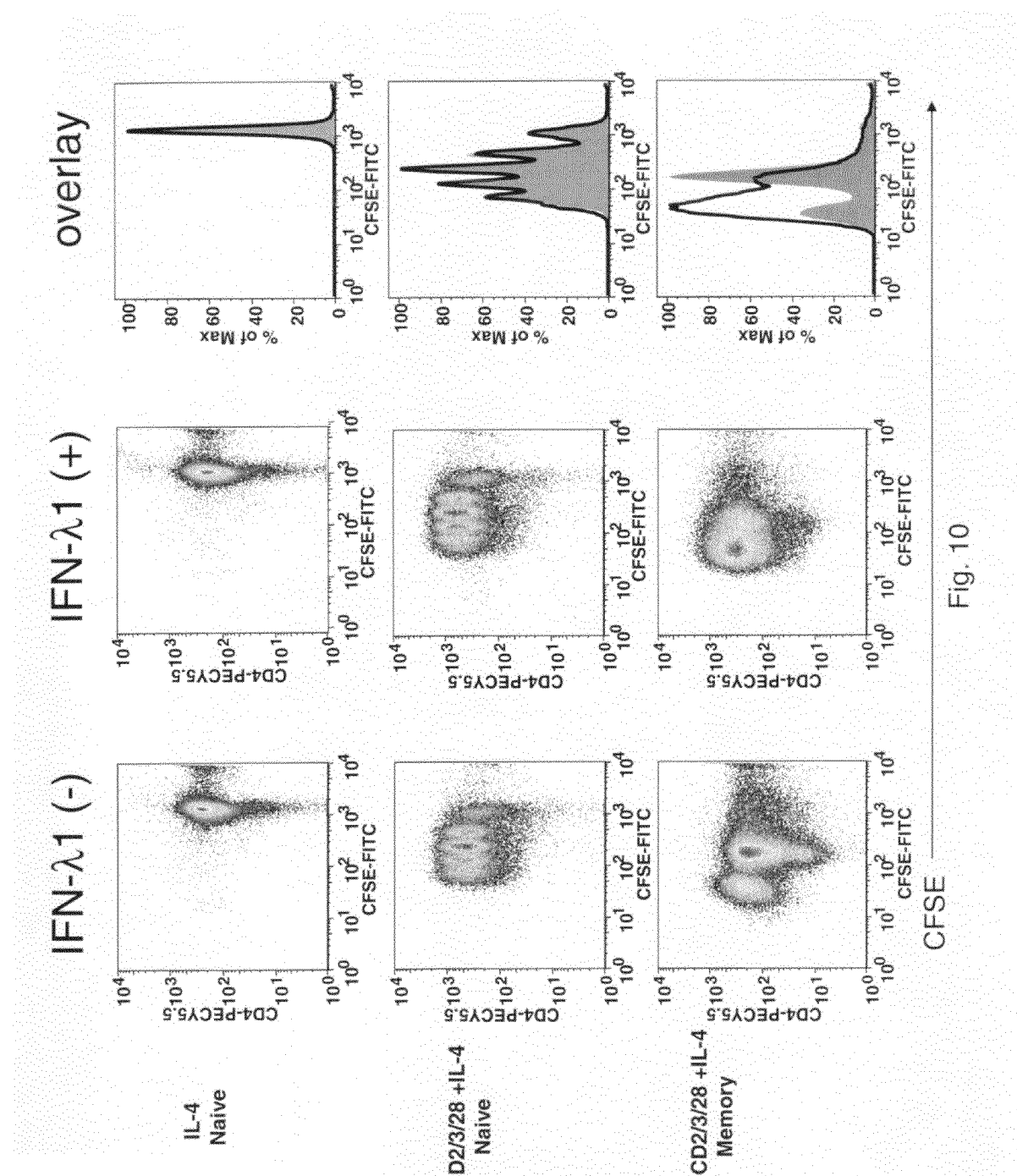
FIG. 10 shows the effect of IFN-λ1 on $CD4^+$ T-cell proliferation of naïve and memory T-cells using a CFSE dilution method. Naïve T-cells proliferated more extensively than memory T-cells under Th2 conditions. IFN-λ did not affect proliferation of naïve $CD4^+$ T-cells.

To characterize the potential effects of IFN-λ1 on T-cell function, and to determine whether the decrease in cytokine production was due to inhibition of T-cell proliferation, we assessed its effect on T-cell proliferation. Using the CFSE dilution method, we defined the effect of IFN-λ1 on CD4$^+$ T-cell proliferation in naïve and memory cells. In these experiments, IL-4 alone did not induce proliferation of naïve or memory T-cells. As shown in FIG. 10, naïve T-cells proliferated more extensively than memory T-cells under Th2 conditions. IFN-λ1 did not affect proliferation of naïve CD4$^+$ T-cells, which undertook four rounds of division over the 6-day culture period. A minor enhancement of proliferation was noted in memory cells. No significance difference in the morphology of expanded naïve T-cells or memory T-cells was observed in the presence or absence of IFN-λ1.

Example 11

IFN-λ1 Inhibits T-Cell Differentiation

We investigated whether IFN-λ1 affects the phenotype or differentiation of naïve and memory T-cells upon activation. Two memory T-cell subsets have previously been defined based on their expression of the lymph node homing receptors CD62L and CCR7 and designated "central memory"-like T-cells (CD62L$^+$CCR7$^+$; which primarily reside in lymphoid tissue), and "effector memory" T-cells (CD62L$^-$CCR7$^-$; which are the predominant subset in non-lymphoid tissue, including the periphery). We examined the expression of these two homing receptors on naïve and memory CD4$^+$ T-cells after stimulation under either neutral or Th2 conditions, in the presence or absence of IFN-λ1.

Figure 11A:
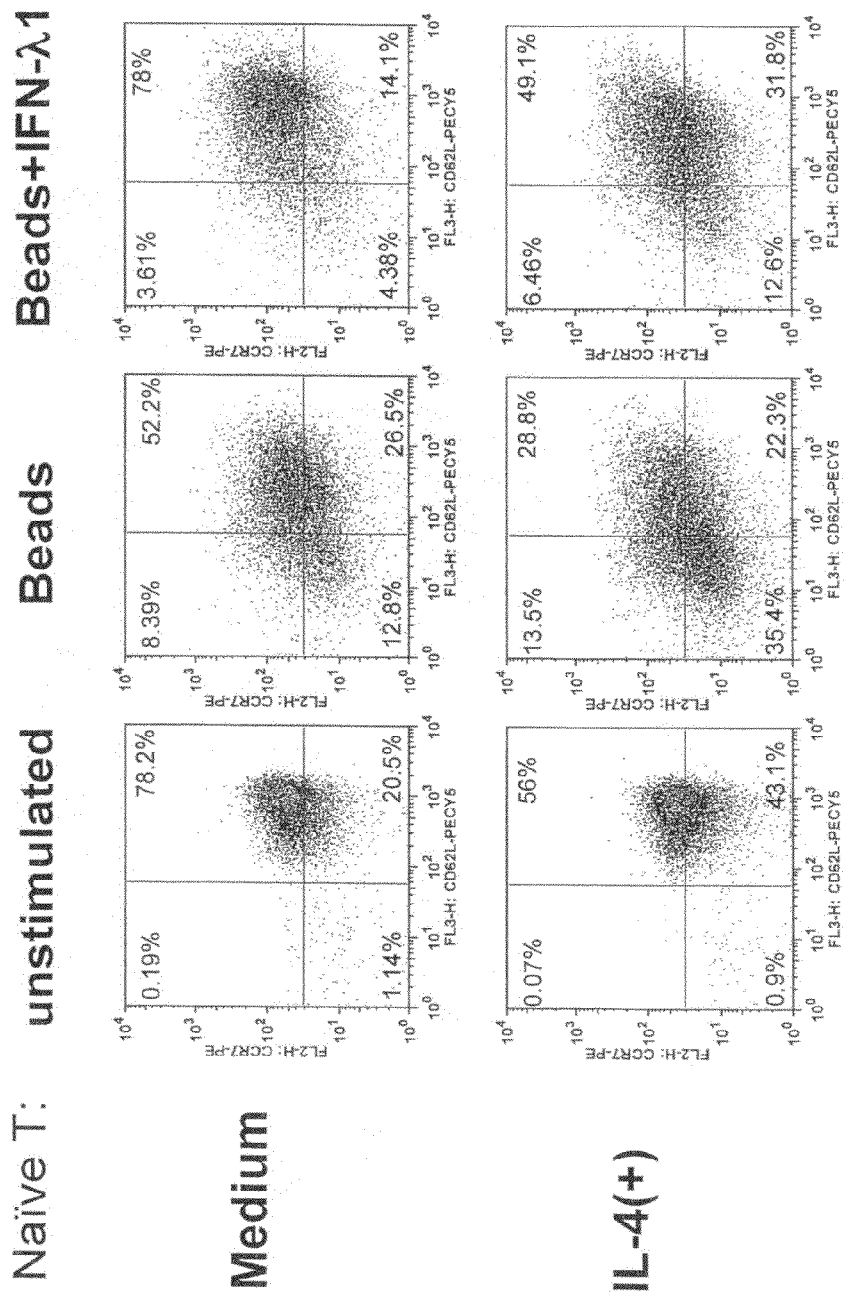
FIG. 11A shows that IFN-λ prevented the activation-induced down-regulation of CD62L under both neutral and Th2 conditions on naïve $CD4^+$ T-cells. Bead activation induced the differentiation of CD62L⁺CCR7⁺ cells into CD62L⁻CCR7⁻ cells. IFN-λ significantly prevented the activation-induced differentiation of naïve cells and maintained the phenotype of CD62L⁺CCR7⁺.
Figure 11B:
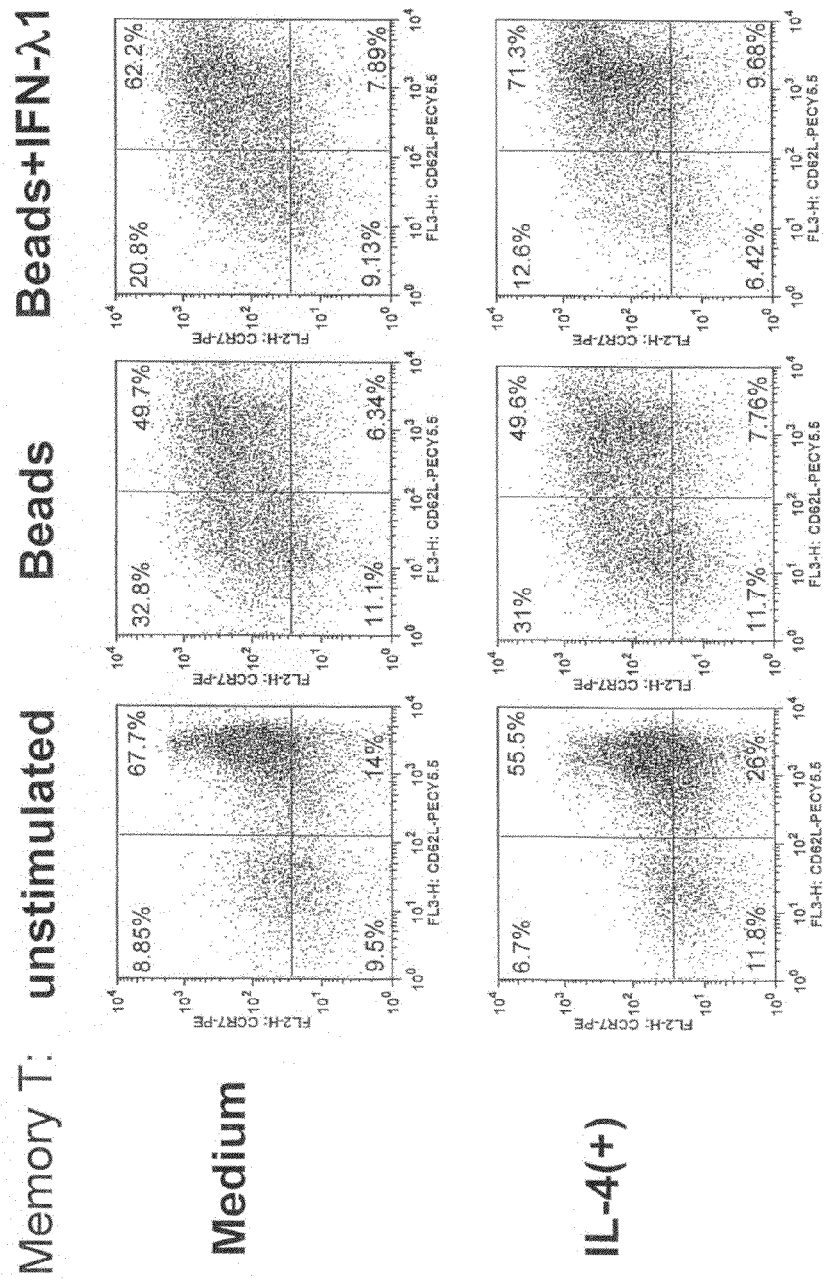
FIG. 11B shows that IFN-λ prevented the activation-induced down-regulation of CD62L under both neutral and Th2 conditions on memory CD4⁺ T-cells. Bead activation induced down-regulation of CD62L. IFN-λ significantly prevented the activation-induced differentiation of memory cells.

As shown in FIGS. 11A and 11B, IFN-λ1 prevented the activation-induced down-regulation of CD62L under both neutral and Th2 conditions, on both naïve or memory CD4$^+$ T-cells. Freshly-isolated naïve CD4$^+$ T-cells were CD62L$^+$CCR7$^+$. After the 3-day culture period, the majority of un-stimulated, (previously naïve) cells had retailed this "central memory-like" phenotype and were CD62L$^+$CCR7$^+$ (78.2%). When exposed only to IL-4 for 3 days, a smaller proportion of these cells was CD62L$^+$CCR7$^+$ (56%). Bead-mediated activation caused a loss of this double positive population, both in medium alone (78.2% to 52.2%) and in the presence of IL-4 (56% to 28.8%). The decrease coincided with an increase in cells with a CD62L$^-$CCR7$^-$ phenotype (12.8% and 35.4%, respectively). Therefore, bead activation induced the differentiation of CD62L$^+$CCR7$^+$ cells into CD62L$^-$CCR7$^-$, effector-memory-like cells; this process was enhanced by IL-4. The presence of IFN-λ1 in the medium significantly prevented this activation-induced differentiation of naïve T-cells and maintained the phenotype of CD62L$^+$CCR7$^+$ in activated naïve T-cells, in the presence or absence of IL-4 (49.2% and 78%, respectively).

The majority of memory CD4$^+$ T-cells was central memory-like T-cells, whether they were cultured with medium alone (67.7%) or in the presence of IL-4 (55.5%). Upon stimulation with beads, these cells continued to express CCR7, but down-regulated CD62L (un-stimulated vs. bead-stimulated cells: 8.85% vs 32.8% CD62L$^-$CCR7$^+$), with a corresponding reduced percentage of central memory-like T-cells (49%). IL-4 did not alter the differentiation of memory T-cells upon activation with beads. However, IFN-λ1 once again inhibited the differentiation of these central memory-like T-cells into CD62L$^-$CCR7$^+$ cells, and maintained their double positive phenotype of non-activated central memory-like cells (62.2%). Thus, IFN-λ1 prevented the activation-induced differentiation of central memory T-cells, and may represent a mechanism by which effector cells are sequestered in the lymph node and rendered incapable of entry into the periphery by modulation of their homing receptor expression.

Example 12

IFN-λ1-Pretreatment Inhibits Cytokine Production

Figure 12:
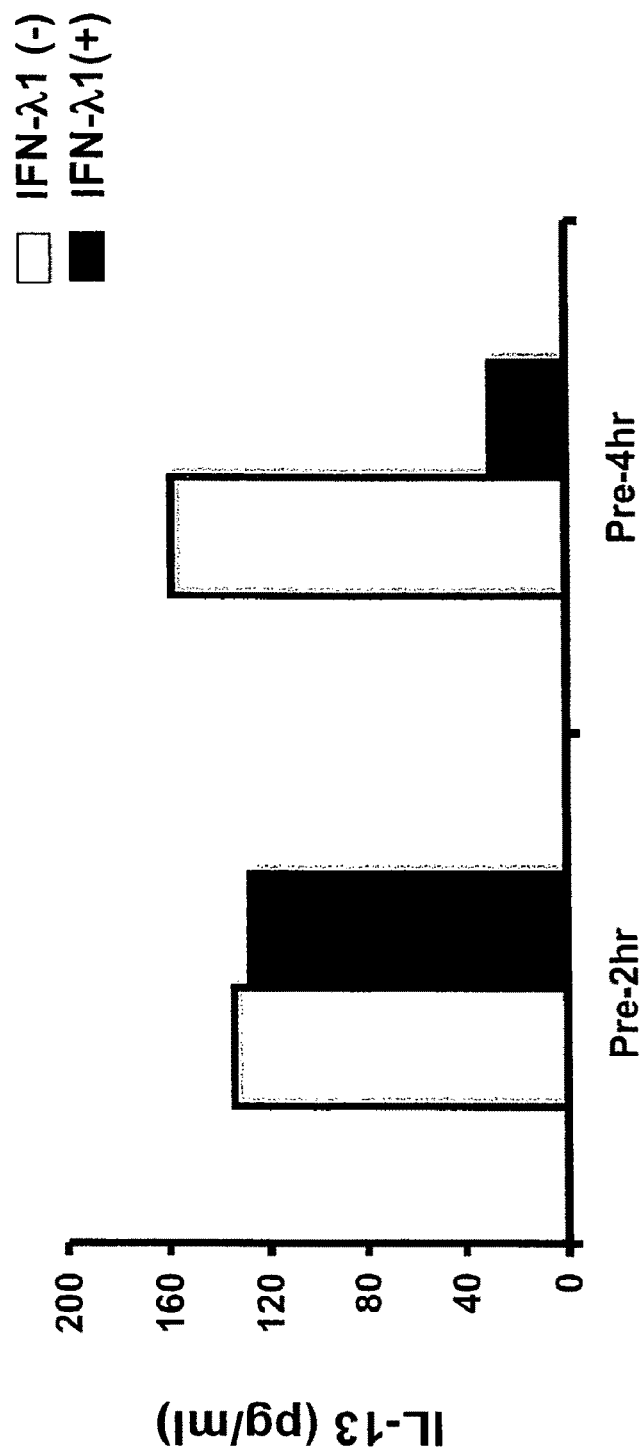
FIG. 12 shows that IFN-λ pre-treatment of PBMC inhibited the release of IL-13. PBMC were isolated and pre-treated with IFN-λ. Treated PBMC were washed followed by stimulation with anti-CD2/3/28 coated beads for 3 days. IFN-λ pre-treatment of 4 hours blocked the IL-13 production at day 3.

Human PBMC were isolated from human blood as described above in Example 1. PBMC were pre-treated with IFN-λ1 (100 ng/ml) for various time periods (i.e., 1, 2, 4 or 8 hours). After IFN-λ1 pretreatment, mononuclear cells were washed free of all added IFN-λ1. Washed cells were then stimulated with CD2/3/28 coated beads, as described. After three days of stimulation, culture supernatants were harvested and the level of secreted IL-13 was quantified by ELISA. As shown in FIG. 12, pre-treatment of mononuclear cells with IFN-λ1 for a time period of 2 hours or less produced a marginal decreased in IL-13 secretion. Pre-treatment of mononuclear cells with IFN-λ1 for a time period of 4 hours or greater produced a down-regulation of IL-13 secretion. Overall, we observed that IFN-λ pre-treatment of mononuclear cells is generally mimicking that of IFN-λ co-incubation with mononuclear cells, in terms of the inhibitory effects on Th2 cytokines.

Example 13

Isolation of Highly-Purified pDC Using One-Step Magnetic "Negative" Purification Yields Cells with Intact Cellular Function To obtain purified plasmacytoid dendritic cells (pDC) for these studies, cells were first enriched from PBMC. Commercially available reagents used for these separations have typically utilized a positive cell selection step that yields highly-purified cells (≧95%) which are bound to magnetic beads. This process has recently been shown to inhibit pDC function through receptor cross-linking, leading to inhibition of cell surface expression and suppression of cytokine production (Fanning et al., 2006, J. Immunol., 177, 5829-39). Upon isolation, the pDC recovered using positive isolation no longer produce IFN-α in response to HSV (a hallmark activity of these cells).

Figure 13A:
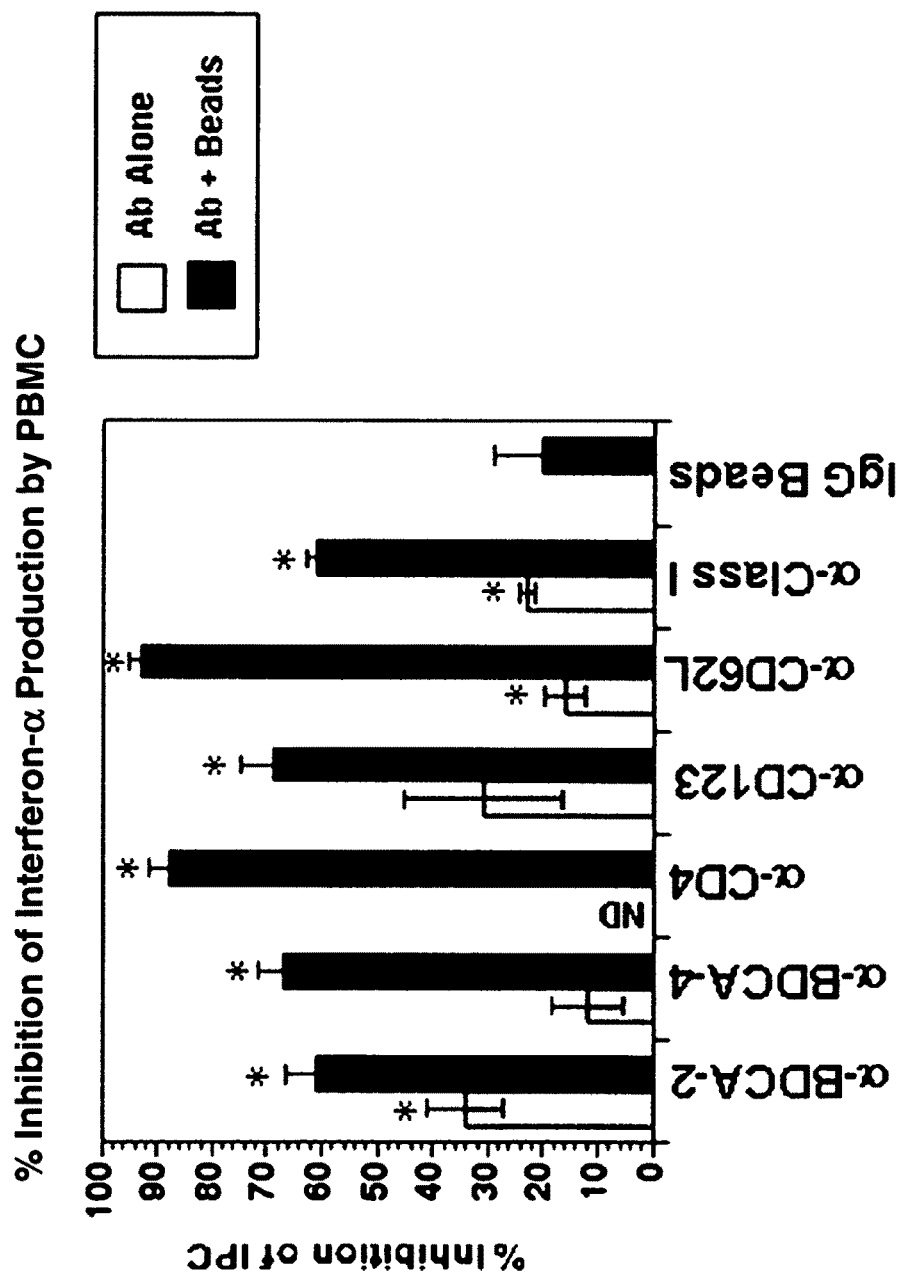
FIG. 13 shows the effect of the positive cell selection process on plasmacytoid dendritic cell (pDC) function (from a previous study, Fanning et al., 2006, J. Immunol., 177, 5829-39). Notably, antibodies are employed during positive cell selection. To perform the positive cell selection, beads coupled with antibodies were added to PBMC. Cells were collected after they are bound to beads. PBMC cells that are bound to various beads showed significant reduction in the ability to respond to a stimulus (e.g., Herpes Simplex virus (HSV)-stimulation) as evidenced by the reduced production of IFN-α from these cells (A). pDC isolated by the positive cell selection process also show reduced responsiveness (B).
Figure 13B:
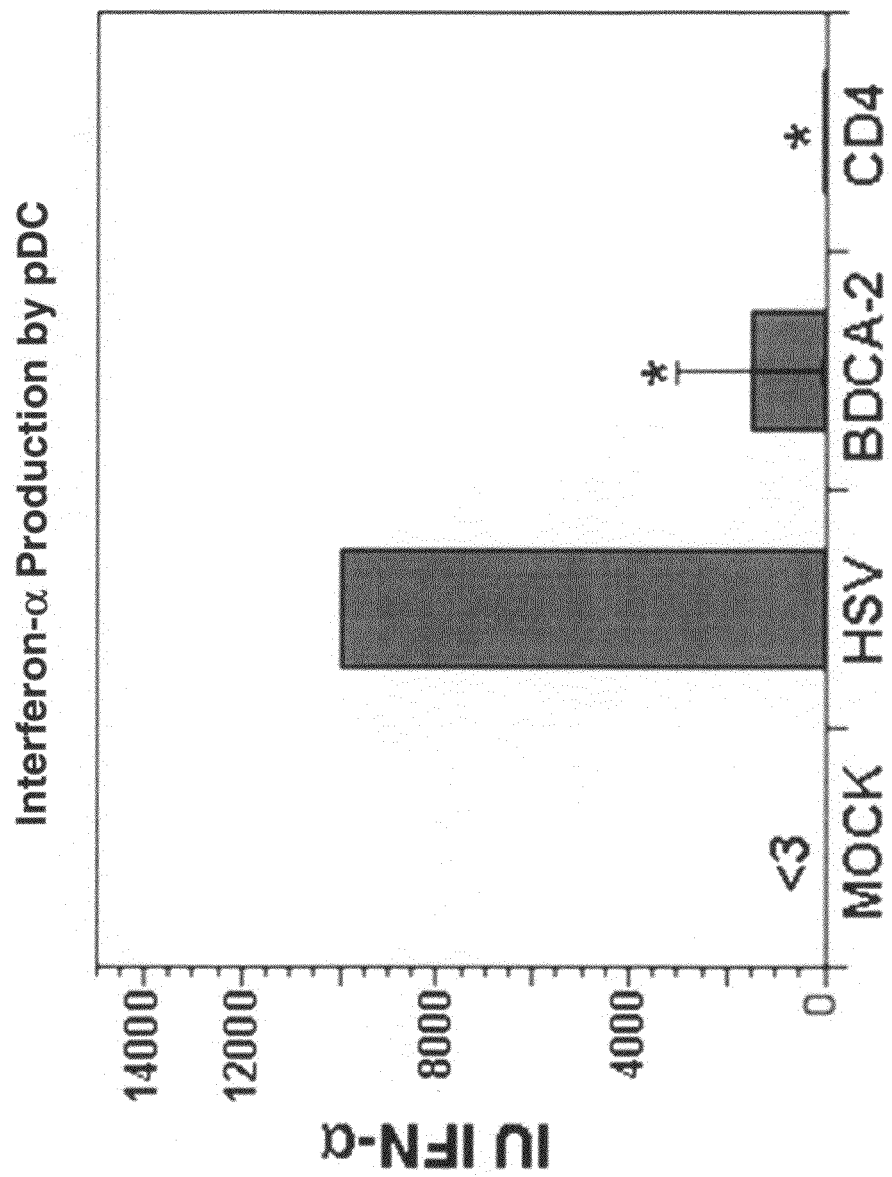

In FIG. 13B, pDC were incubated with biotinylated antibodies specific for BDCA-2 or CD4 (both of which are highly expressed on pDC) in the presence of streptavidin-coated microbeads. This treatment mimics the positive selection process: (i) the biotinylated antibodies bind their cellular targets; (ii) the biotinylated microbeads bind multiple antibodies on the surface of the cell; and (iii) cellular receptors are drawn together on the surface of the cell, inducing signaling events in a phenomenon known as receptor cross-linking As shown, cells treated in this manner (cross-linking either BDCA-2 or CD4) produce significantly less IFN-α upon stimulation with HSV than do untreated pDC. In FIG. 13A, pDC have been treated with a greater variety of biotinylated antibodies, all with specificities to molecules also known to be present on pDC. The cells were then stimulated with HSV in the presence or absence of streptavidin-coated microbeads. Values shown denote percent (%) inhibition of Interferon-Producing Cell (IPC) function (determined using IFN-α production). As shown, cross-linking each of the indicated molecules leads to significant inhibition of pDC function (FIG. 13A).

Figure 14:
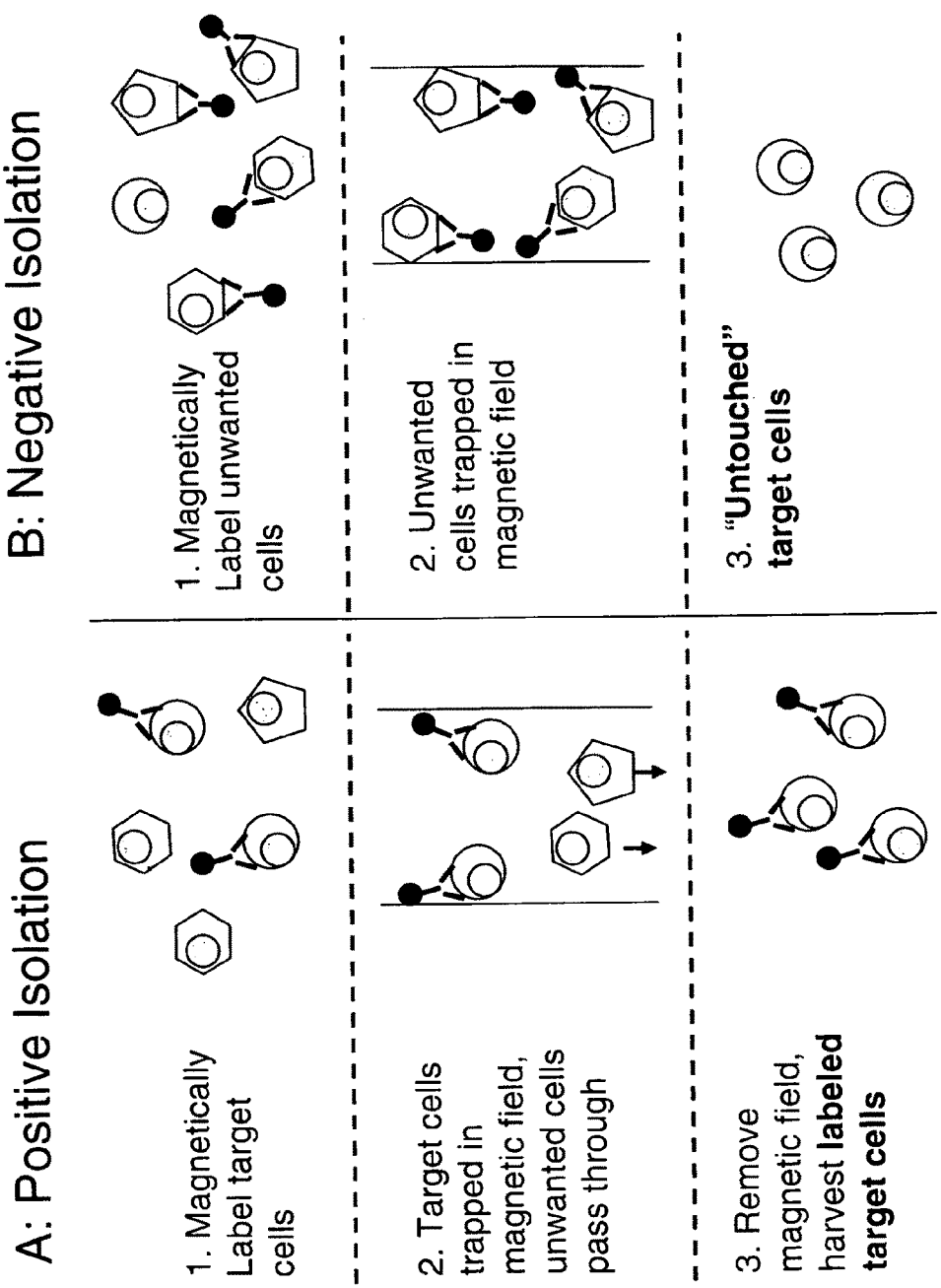
FIG. 14 shows the schematic depiction showing the positive cell selection (A) and negative cell selection (B) during the isolation of pDC from PBMC.
Figure 15:
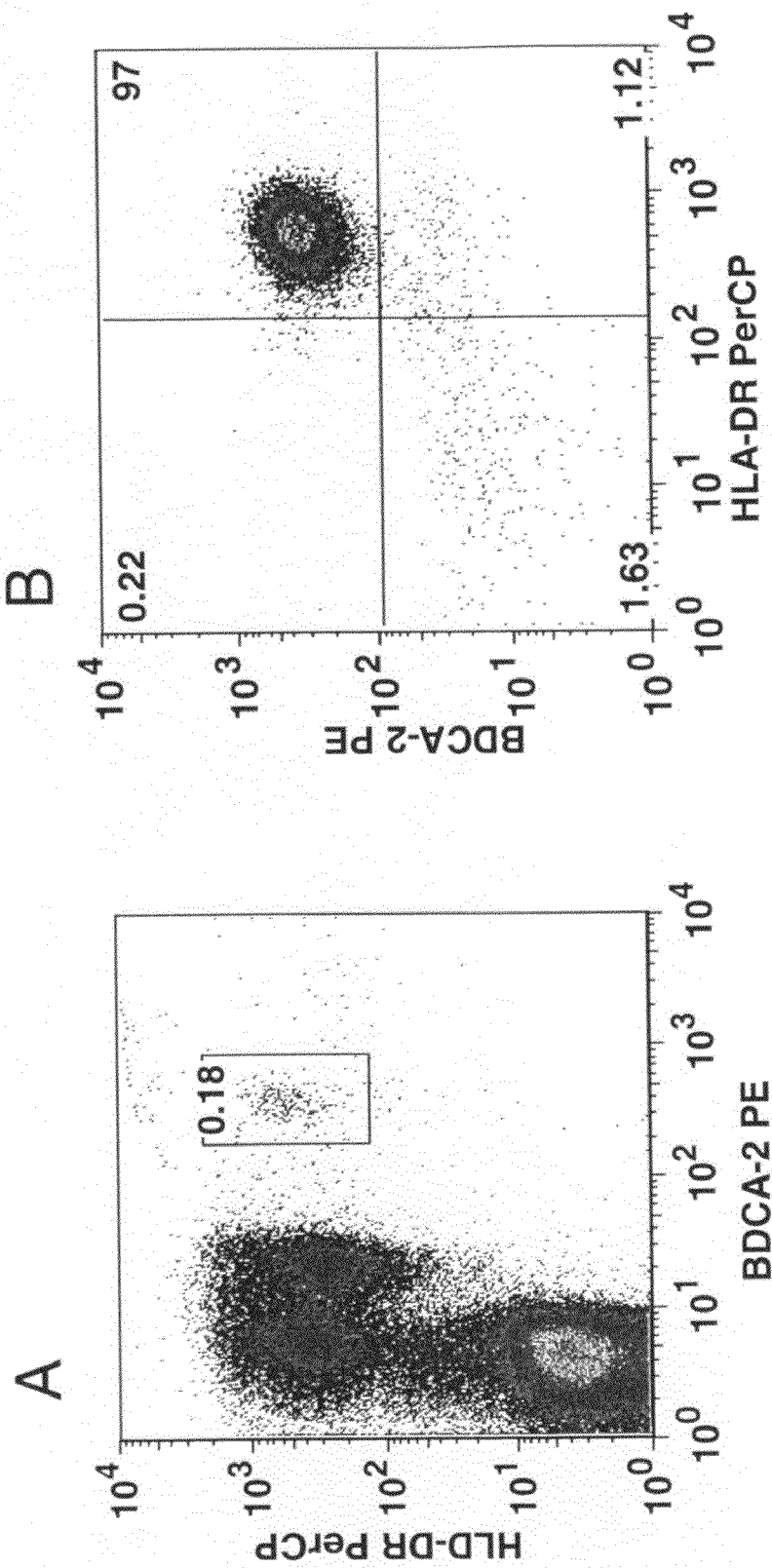
FIG. 15 shows the two-color flow cytometry on isolated peripheral mononuclear cells (PBMC) using PE-conjugated anti-CD303 (BDCA-2) and PerCP-conjugated anti-HLA-DR antibodies. The frequency of pDC was ~0.2% of the PBMC population (A). pDC was identified as staining positive for HLA-DR and CD303. Following the negative cell selection, pDC was enriched to ~97% (B). Note that purified pDC responded normally to HSV, CpG, and imiquimod in the production of IFN-λ1 (C).
Figure 15:
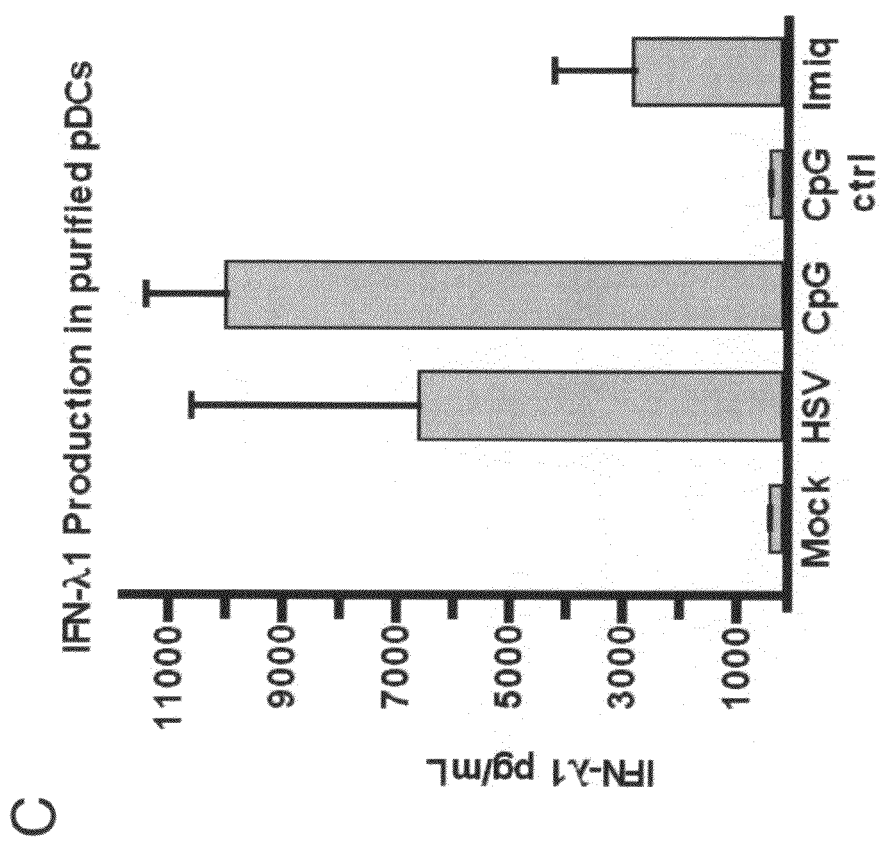

Thus, the positive selection process yields cells that are labeled with microbead-conjugated antibodies, and exhibit decreased function (FIG. 14A). Recently, commercial reagents have become available which yield negatively-isolated cells of the same high purity (≧95%) that are untouched by antibodies or microbeads (FIG. 14B). PBMC were isolated from buffy coats and labeled with fluorescently-labeled antibodies (anti-BDCA-2 and anti-HLA-DR) to measure starting percentage of pDC (FIG. 15A). In this study, PBMC were negatively enriched for pDC using the plasmacytoid DC isolation kit as described in the Methods section. This one-step process is the most efficient commercial method for isolating highly-purified, "untouched" cells and routinely yields highly-purified populations (FIG. 15B). These cells are functionally intact and are able to respond to classical pDC stimuli by producing high levels of IFN-λ1. To demonstrate this, enriched pDC were stimulated for 24 hours with Herpes Simplex virus (HSV) and immunostimulatory CpG oligodeoxynucleotides (ODN). Supernatants were harvested and assayed for the IFN-λ1 using ELISA (FIG. 15C). pDC respond vigorously to each stimulus, as shown by their robust production of cytokine.

Example 14

IFN-λ1 Alters the Expression of CCR7 and CD62L on Human pDC

Figure 16A:
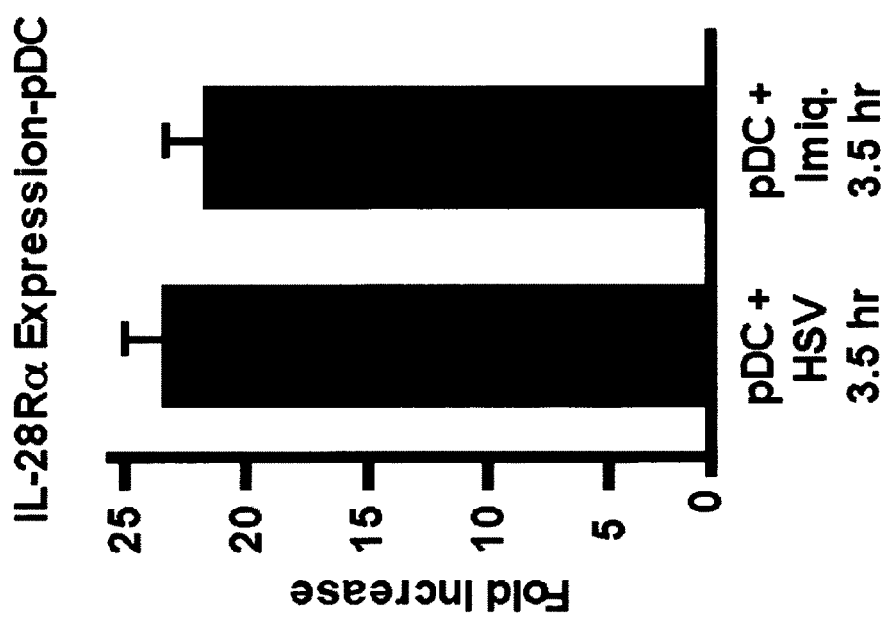
FIG. 16 shows the fold mRNA increase of IL-28Rα (i.e. IFN-λ1 receptor) in the highly-purified pDC that were treated with IFN-λ1 (A). Expression of homing receptors CCR7 and CD62L on the surface of both IFN-λ1-treated pDC and myeloid dendritic cells (mDC) was determined by flow cytometry using PE-conjugated anti-CCR7 and PeCy5-conjugated anti-CD62L antibodies (B and C).
Figure 16B:
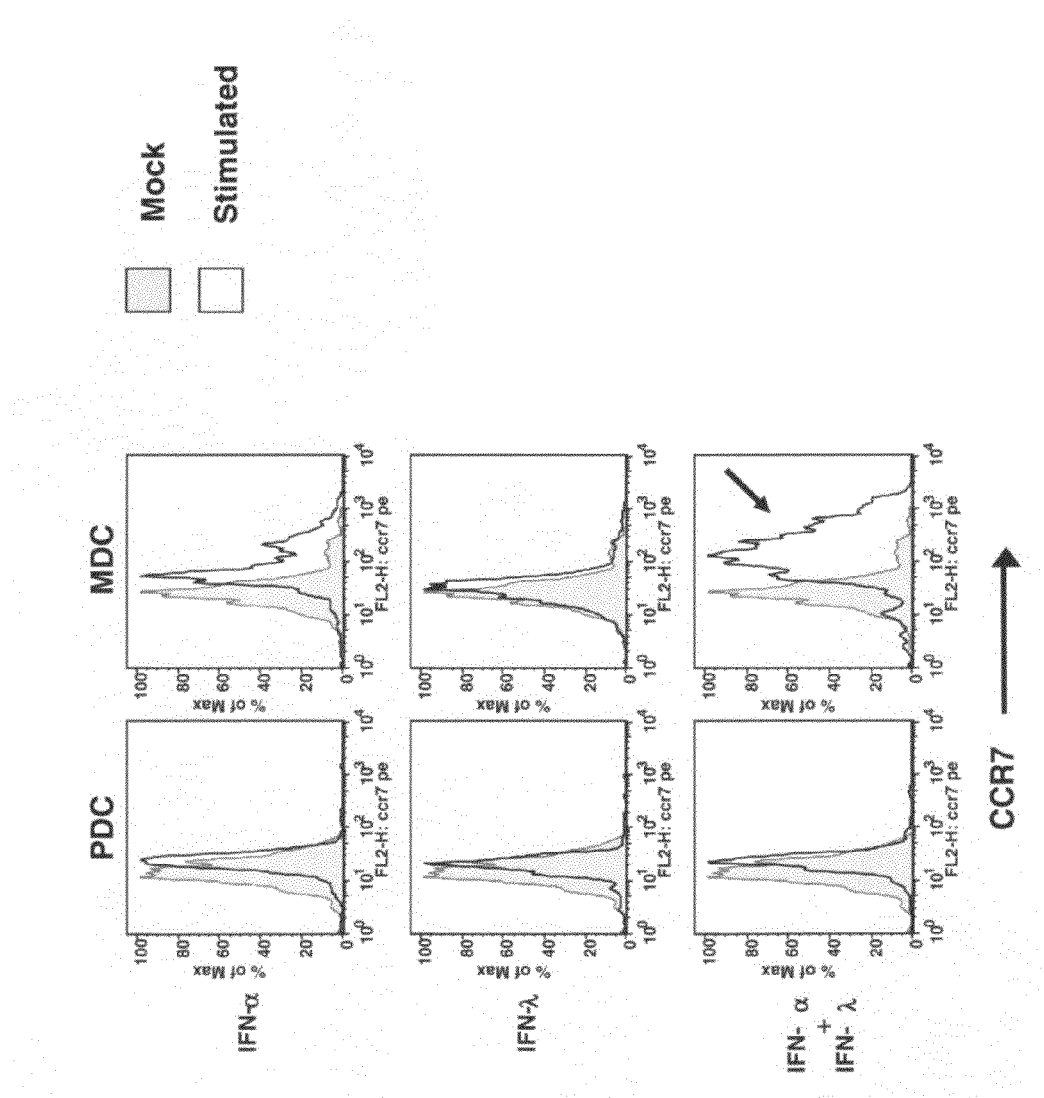

In addition to producing high levels of IFN-λ1, pDC are also able to respond to it. Purified pDC express high levels of mRNA for the IFN-λ receptor (IL-28Rα), and upon stimulation, further upregulate these transcripts (FIG. 16A). When purified pDC were stimulated for 3.5 hours with either HSV or Imiquimod (each known to stimulate pDC, through TLR9 or TLR7, respectively), IL-28Rα transcript levels rise at least 20-fold. This enhanced expression confers a greater ability to respond to IFN-λ in an autocrine as well as exocrine fashion. pDC play a specialized, yet still poorly-characterized, role as antigen presenting cells, a process which is dependent upon their expression of co-stimulatory molecules. Therefore, we investigated the modulation of several of these molecules on pDC by IFN-λ1. In addition to stimulation for 24 hours with IFN-λ1, PBMC were also stimulated with IFN-α, which can act as a survival factor and activation stimulus for pDC. We used flow cytometry to determine activation-dependent changes in expression of cell surface molecules on pDC, using fluorescently-labeled antibodies.

pDC, DC generally and T-cells all regulate their expression of cell-surface homing molecules to localize them appropriately for their degree of activation. Ideally, pDC could be first isolated using negative cell selection procedure. Then, the effect of IFN-λ treatment on the homing molecule expression could be examined. However, because mDC could not be isolated using a similar negative cell selection procedure, this approach could not permit us to compare pDC with mDC.

Figure 16C:
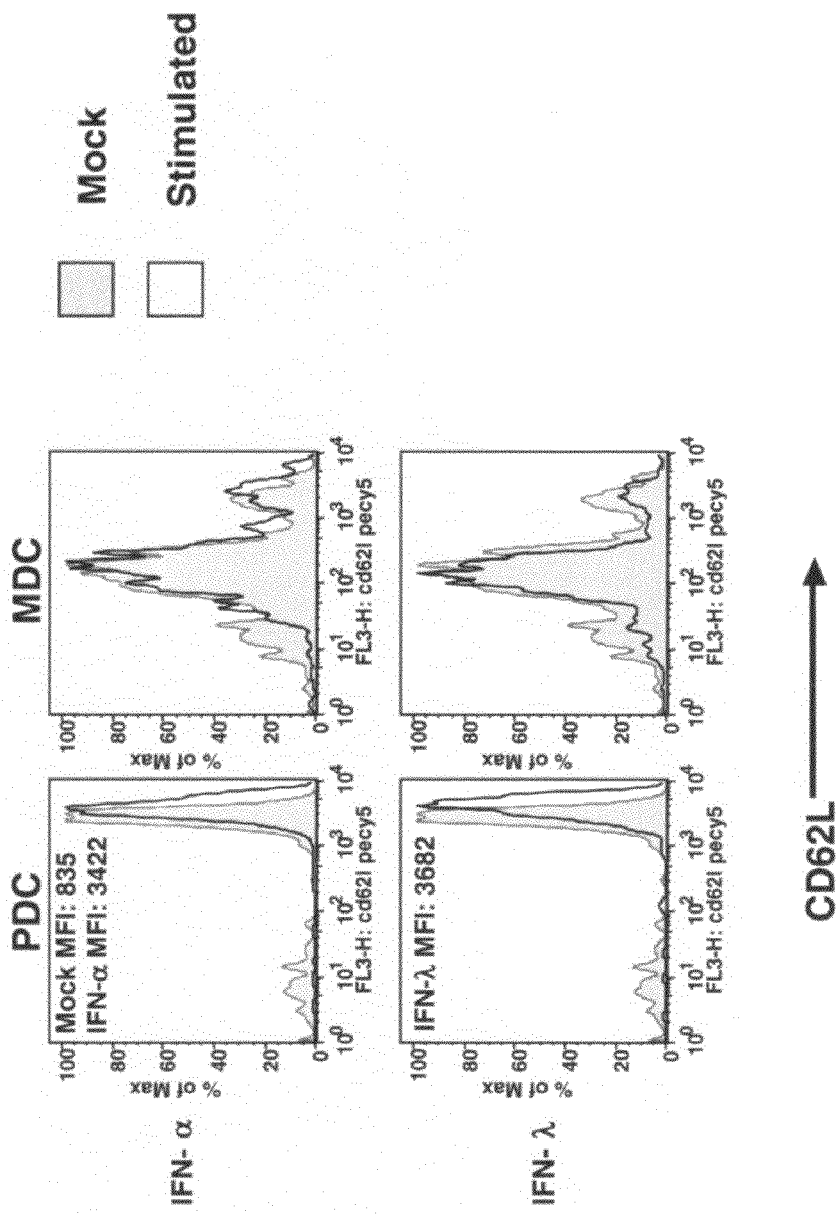

For the purposes of our goal (i.e., to compare pDC and mDC with respect to their homing molecules following IFN-λ treatment), we therefore performed this series of experiments using PBMC. It is expected that the homing molecule response should be identical to that when using negatively isolated pDC. To evaluate the impact of IFN-λ1 on the homing potential of pDC and mDC, PBMC were stimulated with IFN-λ1 for 24 hours; IFN-α was used as a control. mDC and pDC were subsequently identified by flow cytometry and evaluated for its expression of the homing molecules CCR7 and CD62L. IFN-λ1 caused only a slight increase in CCR7 expression on the surface of human pDC (FIG. 16B), but had a much greater effect on CD62L expression (FIG. 16C). In the absence of IFN-λ1, pDC showed a bi-phasic expression of CD62L; approximately 80% (±4.2) of the unstimulated cells were positive and the remainder was negative after 24 hrs in culture. In the presence of IFN-λ1, 99% (±1.1) of the pDC expressed CD62L to a uniform degree, at levels brighter (70.2%±8.2) than un-stimulated pDC (mean increase of MFI: 2770 to 3930). Enhancement of CD62L expression has a significant impact on pDC function. Expression of CD62L is critical and necessary for inducing migration of these cells out of the periphery and into secondary lymphoid tissue (Cella et al., 1999, Nat. Med., 5, 919-23). Since IFN-λ1 is a powerful stimulator of CD62L expression on pDC, it can be used to selectively modify the ability of pDC to migrate to secondary lymphoid organs (e.g., lymph nodes).

These findings are in stark contrast to the effect of IFN-λ on mDC (FIG. 16). mDC upregulate CCR7 in response to treatment with IFN-λ+IFN-α (FIG. 16A), but do not modulate CD62L (FIG. 16B), in complete discordance with pDC. This difference offers a method of selectively targeting modulation of pDC using IFN-λ1.

Example 15

IFN-λ1 Modulates Co-Stimulatory Molecule Expression on pDC

The co-stimulatory molecules CD80, CD83, CD86 and Inducible COStimulator Ligand/B7RP-1 (ICOS-L), and the homing molecules CCR7 and L-selectin (CD62 Ligand), were examined. While the activity of CD80 and CD86 are well-studied, much less is known about signaling through ICOS-L and CD83; ICOS-L can be induced in pDC and binds ICOS during co-stimulation of naive T-cells (Ito et al., 2007, J. Exp. Med., 204, 105-15), while CD83 remains a poorly-defined DC activation marker.

In these studies, IFN-λ1 enhanced CD80 and ICOS-L expression on pDC and synergized with IFN-α to upregulate CD83. As shown in FIG. 17A, IFN-λ1 was able to upregulate the expression of CD80 and ICOS-L. IFN-α, a related cytokine, could only upregulate CD80. No significant changes in CD83 or CD86 expression were induced with IFN-λ1 alone. However, the addition of IFN-α strongly enhanced the ability of IFN-λ to upregulate CD80, CD83 and ICOS-L over that of either alone (51%±16.8, 40%±12.1 and 24%±9.6, respectively).

The modulation of co-stimulatory molecules by IFN-λ1 is, again, completely divergent between mDC and pDC. mDC do not upregulate CD80 or ICOS-L in response to IFN-λ1, but instead express CD86, the complete opposite effect to what is seen in pDC. This reinforces the findings for homing molecule expression, that treatment of pDC with IFN-λ1 induces changes in cell surface molecule expression that are clear and distinct from effects on mDC. The changes in downstream pDC function will therefore be unique, and are the focus of the next set of experiments.

Example 16

IFN-λ1 Alters the Immunostimulatory Ability of pDC

Figure 18A:
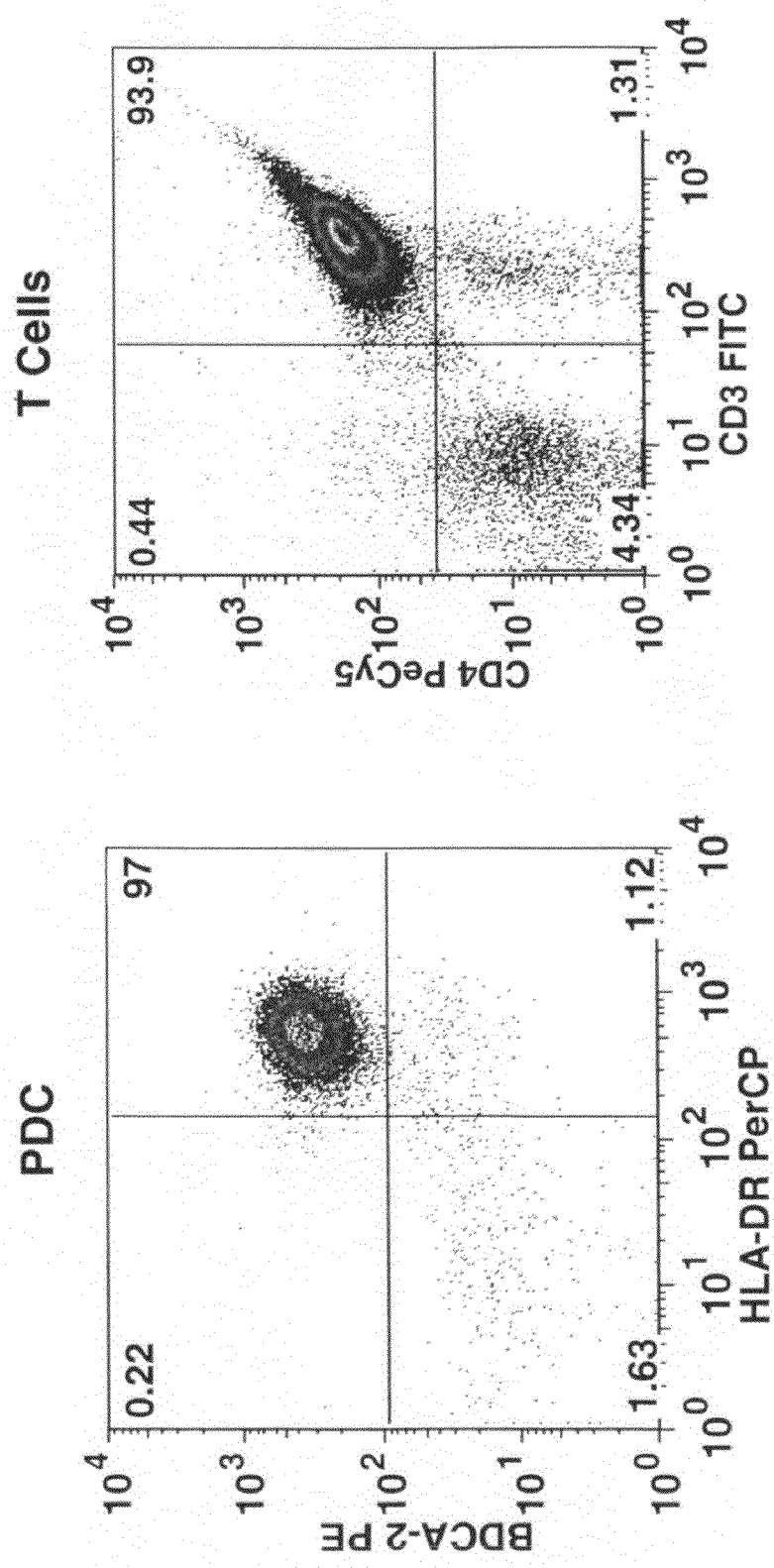
FIG. 18A shows the two-color flow cytometry on isolated pDC using PE-conjugated anti-BDCA-2 (CD303) and PerCP-conjugated anti-HLA-DR antibodies, and on isolated T-cells using PeCy5-conjugated anti-CD4 and FITC-conjugated anti-CD3 antibodies. pDC was treated with IFN-λ1 followed by co-culture in a MLR with T-cells. In the MLR, supernatants from pDC and T-cells co-cultures were harvested to determine the levels of secreted cytokines IL-10 (B), IL-13 (C) and IFN-γ (D) by ELISA. IFN-λ treated pDC showed a reduction in IL-10, IL-13 IFN-γ production in a mixed lymphocyte reaction (MLR).
Figure 18:
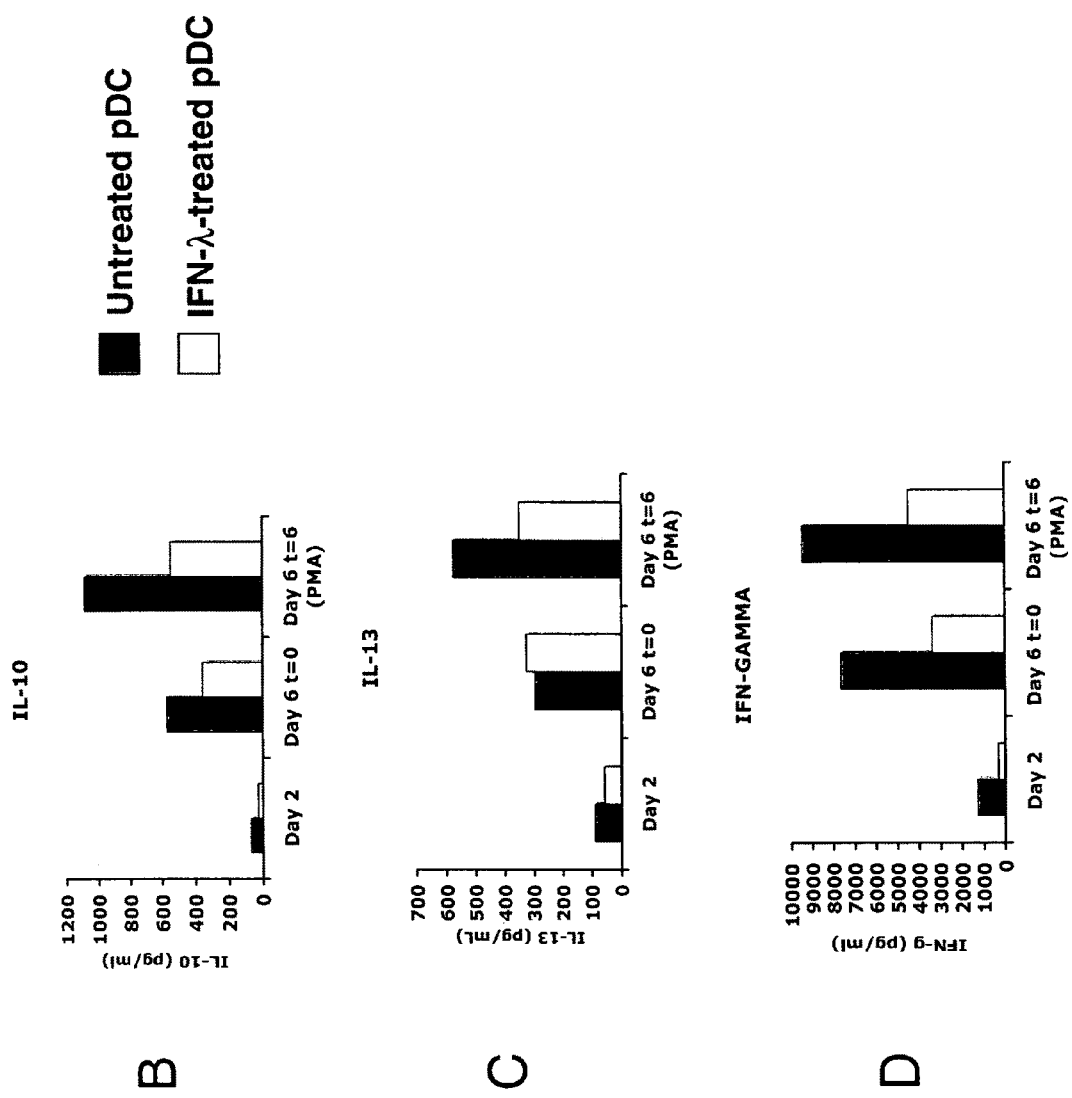

The IFN-λ1-induced changes in surface molecule expression suggest that pDC display an altered ability to stimulate T-cell responses. To determine functional relevance of these changes, pDC were treated overnight with IFN-λ1, then washed and co-cultured with allogeneic T-cells in a mixed lymphocyte reaction (MLR) (FIG. 18A). Supernatants were harvested at days 2 and 6; at day 6 a portion of cells were cultured for an additional 5 hours in fresh medium supplemented with PMA/ionomycin in order to trigger de novo cytokine expression. Levels of the signature cytokines IL-10 (FIG. 18B), IL-13 (FIG. 18C), and IFN-γ (FIG. 18D) were determined by ELISA. Compared with untreated cells, IFN-λ1-treated pDC show a significant difference in their ability to stimulate production of each of the measured cytokines.

Figure 19A:
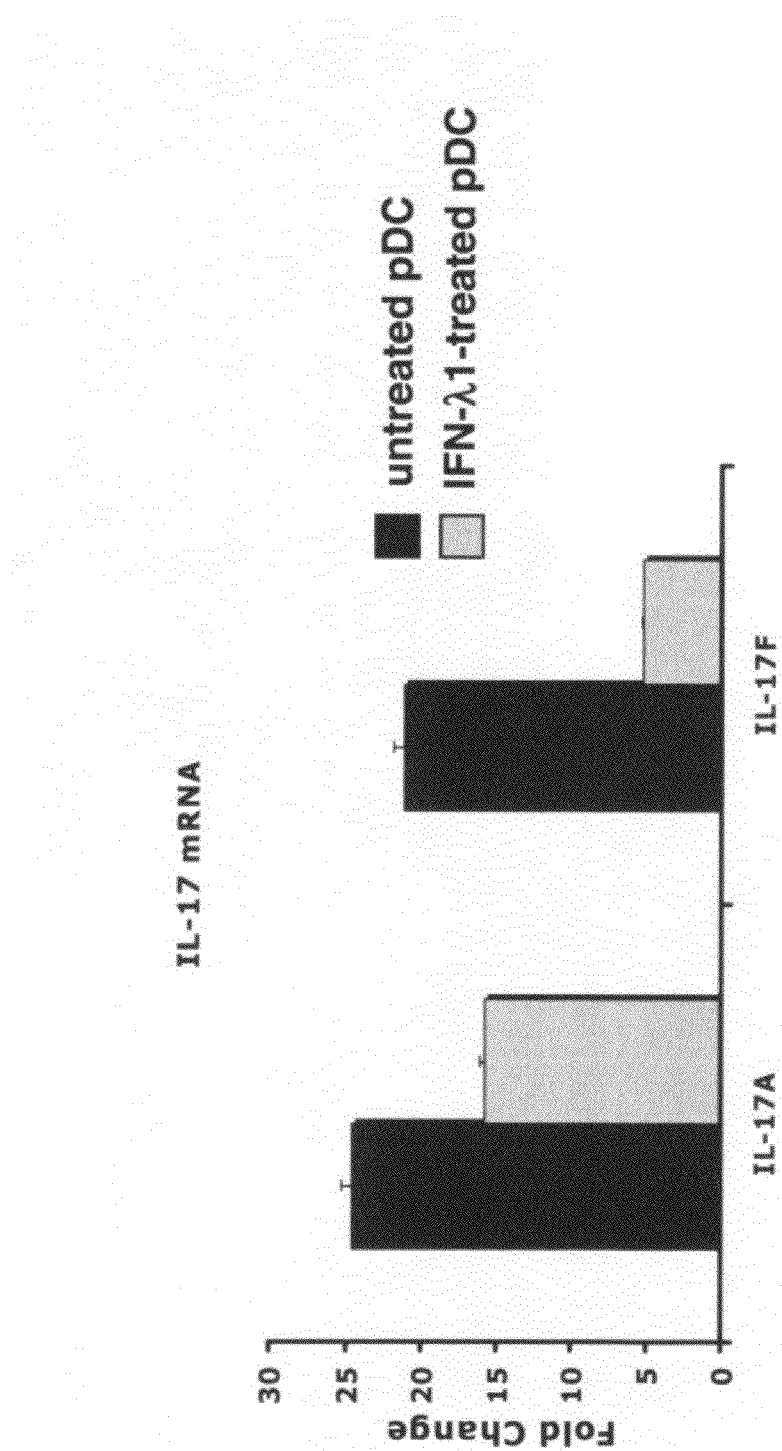
FIG. 19 shows the ability of IFN-λ1-treated pDC to inhibit IL-17 production by T-cells. IFN-λ1-treated pDC was shown to reduce IL-17A and IL-17F mRNA levels in T-cells (A) as well as to reduce IL-17A and IL-17F protein levels in a mixed lymphocyte reaction (MLR) (B).

Of specific interest is the inhibition of IL-17 production by T-cells, mediated by IFN-λ1-treated pDC (FIG. 19A), which was manifest in two distinct ways. On one hand, treated pDC elicited an overall decrease in IL-17, as evidenced by a reduction in the mRNA and protein levels of the two main isoforms, IL-17A and IL-17F. In addition, IL-17F was inhibited to a greater degree than IL-17A. At the protein level, production of both IL-17A and IL-17F are also inhibited by IFN-λ1-treated pDC (results shown are representative of 3 experiments).

Figure 19B:
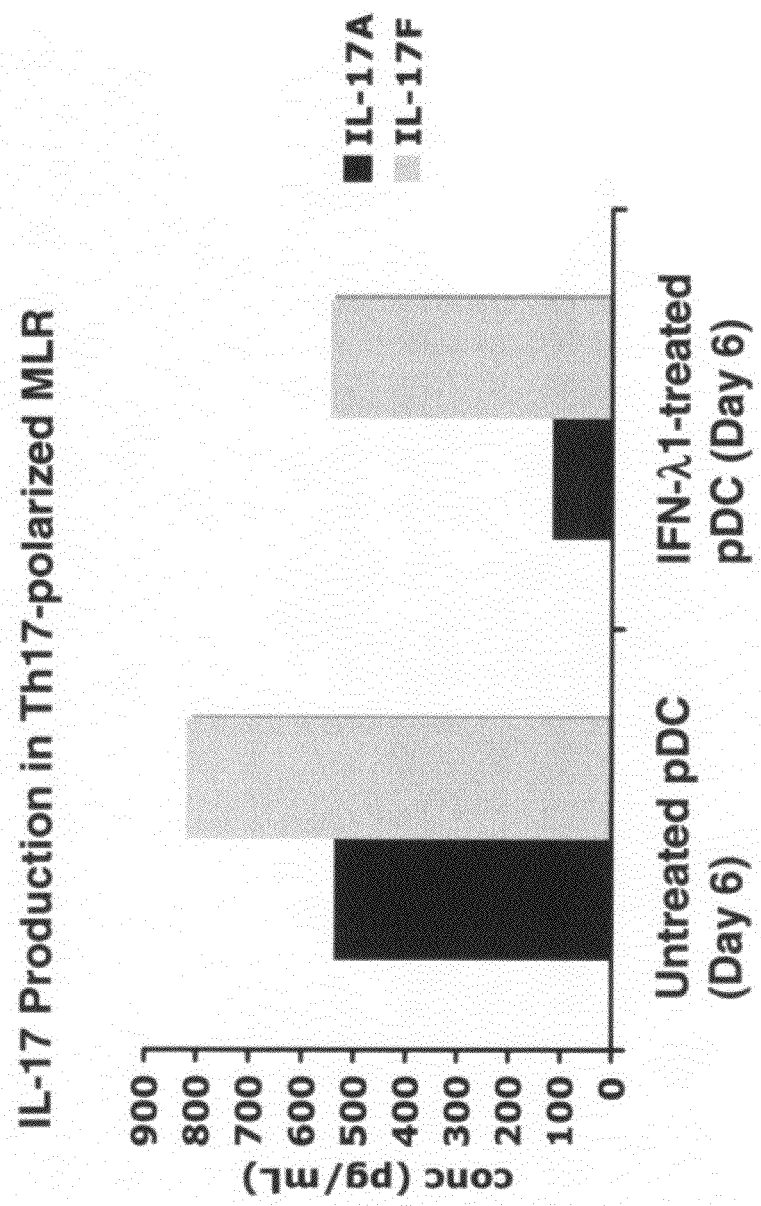

This is an extremely robust effect that occurs even when the MLRs are carried out in the presence of cytokines that drive Th17 polarization, namely IL-6, IL-1b and TGF-β (FIG. 19B). Therefore, not only are IFN-λ1-treated pDC able to diminish IL-17 production by T-cells, but do so within the microenvironment that so effectively drives inflammation. These data highlight the increasingly important activity of IFN-λ1 as an immunomodulator, and represent the first evidence of DC-mediated regulation of IL-17 isoforms.

The Examples are merely illustrative of the invention and are not intended to limit the scope of the invention. One of skill in the art will recognize that various modifications may be made to the embodiments described herein without departing from the spirit and scope of the invention, which is defined by the appended claims. All the references and patents cited in this application are incorporated by reference in their entirety.

---

What is claimed is:

1. A method of ex vivo treatment of plasmacytoid dendritic cells (pDC), comprising the steps of:
   (a) obtaining peripheral blood from a human subject;
   (b) isolating mononuclear cells from said peripheral blood;
   (c) isolating pDC from said isolated mononuclear cells using a negative cell selection;
   (d) exposing said isolated pDC to interferon-lambda (IFN-λ); and
   (e) administering said exposed pDC to said human subject, wherein said IFN-λ is present in an amount sufficient to inhibit pDC-supported cytokine release in a mixed lymphocyte reaction assay, and
   wherein said pDC-supported cytokine is selected from the group consisting of interferon-gamma (IFN-γ), interleukin-13 (IL-13), interleukin-10 (IL-10) and interleukin-17 (IL-17).

2. The method of claim 1, wherein said negative cell selection is performed by (i) exposing said isolated mononuclear cells to a magnetic bead that is coupled with a monoclonal antibody against a cell surface molecule that is present on said mononuclear cells but absent on pDC, and (ii) removing said mononuclear cells that are bound with said magnetic bead.

3. The method of claim 2, wherein said cell surface molecule is selected from the group consisting of CD1a, CD3, CD11c, CD14, CD16, CD19, CD20, CD56, BDCA1, BDCA3, and glycophorin A.

4. The method of claim 1, wherein said IFN-λ is one compound selected from the group consisting of IFN-λ1, IFN-λ2, and IFN-λ3.

5. The method of claim 1, wherein said IFN-λ amount is in the range about 1 ng/mL to about 200 μg/mL.

6. The method of claim 1, wherein said IFN-λ amount is in the range of about 100 ng/mL to about 10 μg/mL.

7. The method of claim 1, wherein said exposing step is performed for about 1 hour to about 24 hours.

8. The method of claim 1, wherein said exposing step is performed for about 6 hours to about 12 hours.

9. The method of claim 1, wherein said IL-17 is IL-17A or IL-17F.

10. The method of claim 1, wherein said human subject is suffering from asthma.

11. The method of claim 10, wherein said asthma is virus-induced or allergen-induced.

12. The method of claim 1, wherein said isolated pDC has a cell purity of greater than 95%.

13. The method of claim 1, wherein said isolated pDC has a cell purity of greater than 97%.

14. The method of claim 1, wherein said exposed pDC are administered to a human subject in the range of about $5 \times 10^4$ cells to about $5 \times 10^6$ cells.

15. The method of claim 1, wherein said exposed pDC are administered to a human subject in the range of about $1 \times 10^6$ cells.

16. The method of claim 1, further comprising the step of: (f) administering a composition comprising IFN-λ to said human subject.

17. The method of claim 16, wherein said IFN-λ composition is administered nasally, intravaneously, or orally.

18. The method of claim 16, wherein said step (f) is performed simultaneously or sequentially with step (e).

* * * * *